United States Patent
Killian et al.

(10) Patent No.: US 11,267,872 B2
(45) Date of Patent: Mar. 8, 2022

(54) POLYCLONAL ANTIBODIES PRODUCED USING HIV-1 TRIMERIC ENVELOPE GLYCOPROTEIN SUBUNITS

(71) Applicant: GNVIE LLC, San Francisco, CA (US)

(72) Inventors: M. Scott Killian, San Francisco, CA (US); Evelin Szakal, San Francisco, CA (US); Girish N. Vyas, San Francisco, CA (US)

(73) Assignee: GNVIE LLC, San Francisco, CA (US)

( * ) Notice: Subject to any disclaimer, the term of this patent is extended or adjusted under 35 U.S.C. 154(b) by 0 days.

(21) Appl. No.: 16/385,455

(22) Filed: Apr. 16, 2019

(65) Prior Publication Data

US 2020/0087382 A1 Mar. 19, 2020

Related U.S. Application Data

(62) Division of application No. 14/771,337, filed as application No. PCT/US2014/019612 on Feb. 28, 2014, now abandoned.

(60) Provisional application No. 61/770,974, filed on Feb. 28, 2013.

(51) Int. Cl.

| | |
|---|---|
| *C07K 16/10* | (2006.01) |
| *C07K 16/00* | (2006.01) |
| *C07K 14/16* | (2006.01) |
| *A61K 39/12* | (2006.01) |
| *A61K 39/21* | (2006.01) |
| *C12N 7/00* | (2006.01) |
| *G01N 33/569* | (2006.01) |
| *C07K 14/005* | (2006.01) |
| *A61K 39/00* | (2006.01) |

(52) U.S. Cl.
CPC .......... *C07K 16/1063* (2013.01); *A61K 39/12* (2013.01); *A61K 39/21* (2013.01); *C07K 14/005* (2013.01); *C07K 14/16* (2013.01); *C07K 16/005* (2013.01); *C12N 7/00* (2013.01); *G01N 33/56983* (2013.01); *G01N 33/56988* (2013.01); *A61K 2039/5258* (2013.01); *C07K 2317/10* (2013.01); *C07K 2317/21* (2013.01); *C07K 2317/24* (2013.01); *C07K 2317/31* (2013.01); *C07K 2317/34* (2013.01); *C07K 2317/622* (2013.01); *C07K 2317/76* (2013.01); *C12N 2740/16051* (2013.01); *C12N 2740/16063* (2013.01); *C12N 2740/16122* (2013.01); *C12N 2740/16134* (2013.01); *C12N 2740/16171* (2013.01)

(58) Field of Classification Search
None
See application file for complete search history.

(56) References Cited

U.S. PATENT DOCUMENTS

| | | | |
|---|---|---|---|
| 5,696,238 | A | 12/1997 | Haigwood et al. |
| 5,852,186 | A | 12/1998 | Sodroski |
| 6,610,542 | B1 | 8/2003 | Bell et al. |
| 2008/0171067 | A1 | 7/2008 | Govindan et al. |
| 2012/0045472 | A1 | 2/2012 | Harrison |
| 2015/0274813 | A1* | 10/2015 | Mouquet ............ C07K 16/1045 424/160.1 |

FOREIGN PATENT DOCUMENTS

WO    WO 2011/108937    9/2011

OTHER PUBLICATIONS

Pfeifer et al., J Acquir Immune Defic Syndr, 2014;67:107-112. (Year: 2014).*
Barre-Sinoussi (1996) "HIV as the Cause of AIDS", The Lancet 348:31-35.
Chen et al., (2015) "Effect of the Cytoplasmic Domain on Antigenic Characteristics of HIV-1 Envelope Glycoprotein", Science 349(6244): 191-195.
Julien et al., (2013) "Asymmetric Recognition of the HIV-1 Trimer by Broadly Neutralizing Antibody PG9", Proceedings of the National Academy of Sciences 110(11): 4351-4356.
Kovacs et al., (2012) "HIV-1 Envelope Trimer Elicits More Potent Neutralizing Antibody Responses than Monomeric gp120", Proceedings of the National Academy of Sciences 109(30): 12111-12116.
McCoy and Weiss (2013) "Neutralizing Antibodies to HIV-1 Induced by Immunization", The Journal of Experimental Medicine 210(2):209-223.
Pancera et al., (2012) "Structural Comparison of Somatically Related PG9 and PG16 in Complex with their Epitope Reveals Differences in Glycan Recognition", Retrovirology 9(2):p. 74.
Polonis et al., (2008) "Recent Advances in the Characterization of HIV-1 Neutralization Assays for Standardized Evaluation of the Antibody Response to Infection and Vaccination", Virology 375: 315-320.
Vyas et al., (2012) "Derivation of Non-Infectious Envelope Proteins from Virions Isolated from Plasma Negative for HIV Antibodies", Biologicals, 40(1): 15-20.
Walker et al., (2009) "Broad and Potent Neutralizing Antibodies from an African Donor Reveal a New HIV-1 Vaccine Target", Science 326:285-289.

(Continued)

*Primary Examiner* — Nicole Kinsey White
(74) *Attorney, Agent, or Firm* — Shweta Chandra; Bozicevic, Field & Francis LLP

(57) ABSTRACT

Polyclonal Antibodies produced using HIV-1 Trimeric Envelope Glycoprotein Subunits (TEGS) are provided. TEGS are comprised of non-infectious complexes comprising a trimeric envelope glycoprotein subunit comprising gp120 bound to membrane-anchored trimeric native gp41. The gp120 and gp41 present in the TEGS are not chemically fixed or cross-linked. Immunization with the TEGS elicits polyclonal antibodies that neutralize diverse viruses in HIV infection assay using peripheral blood mononuclear cells (PBMCs). The present invention relates to a method for reducing the occurrence and/or severity of HIV infections.

11 Claims, 15 Drawing Sheets

Specification includes a Sequence Listing.

(56) References Cited

OTHER PUBLICATIONS

Kovacs et al., (2014) "Stable, Uncleaved HIV-1 Envelope Glycoprotein gp140 Forms a Tightly Folded Trimer with a Native-like Structure", PNAS 111(52):18542-18547.
Sanders et al., (2013) "A Next-Generation Cleaved, Soluble HIV-1 Env Trimer, BG505 SOSIP.664 gp140, Expresses Multiple Epitopes for Broadly Neutralizing but Not Non-Neutralizing Antibodies", PLOS 9(9):e1003618 1-20.
Sanders et al., (2015) "HIV-1 Neutralizing Antibodies Induced by Native-like Envelope Trimers", Science 349(6244):154-164.

* cited by examiner

SEQUENCE LISTING

```
<160> NUMBER OF SEQ ID NOS: 137

<210> SEQ ID NO 1
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Gln Ser Leu Glu Glu Ser Gly Gly Gly Leu Phe Lys Pro Thr Asp Thr
1               5                   10                  15

Leu Thr Leu Thr Cys Thr Val Ser Gly Phe Ser Leu Ser Asn Tyr Gly
            20                  25                  30

Val Val Trp Val Arg Gln Ala Pro Gly Asn Gly Leu Glu Trp Ile Gly
            35                  40                  45

Ile Ile Asp His His Gly Ile Pro Tyr Tyr Ala Thr Trp Ala Lys Ser
        50                  55                  60

Arg Ser Thr Ile Thr Arg Asn Thr Asn Leu Asp Val Thr Leu Lys
65                  70                  75                  80

Met Thr Ser Leu Thr Ala Ala Asp Thr Ala Thr Tyr Phe Cys Ala Arg
            85                  90                  95

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Leu Val Met Thr Gln Thr Glu Ser Pro Val Ser Ala Ala Val Gly
1               5                   10                  15

Ser Thr Val Thr Ile Asn Cys Gln Ala Ser Gln Ser Val Tyr Ser Asn
            20                  25                  30

Asn Asn Leu Ala Trp Phe Gln Lys Lys Pro Gly Gln Pro Pro Lys Arg
            35                  40                  45

Leu Ile His Ser Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Val Phe Ser Gly
            85                  90                  95

Ser Ile Ser Val Phe Gly Gly Gly Thr Glu Val Val Val Lys
            100                 105                 110

<210> SEQ ID NO 3
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Gly Glu Gly Val Arg Gly Gly Leu Leu Lys Pro Thr Asp Thr Leu
1               5                   10                  15

Thr Leu Thr Cys Thr Val Ser Gly Phe Ser Leu Asn Ser Tyr Ala Val
            20                  25                  30

Phe Trp Val Arg Gln Ala Pro Gly Asn Gly Leu Glu Trp Ile Gly Thr
            35                  40                  45

Val Ser Ser Val Gly Asp Thr Tyr Phe Ala Thr Trp Ala Lys Ser Arg
        50                  55                  60

Ser Thr Ile Thr Arg Asn Thr Asn Leu Asn Thr Val Thr Leu Lys Met
65                  70                  75                  80

Thr Ser Leu Thr Ala Ala Asp Thr Ala Thr Tyr Phe Cys Ala
            85                  90
```

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Pro Val Leu Thr Gln Ser Pro Ser Val Ser Ala Ala Leu Gly Ser
1               5                   10                  15

Ser Ala Lys Leu Thr Cys Thr Leu Ser Ser Ala His Lys Thr Tyr Tyr
                20                  25                  30

Ile Glu Trp Tyr Gln Gln Gln Gly Glu Ala Pro Arg Tyr Leu Met
            35                  40                  45

Gln Leu Glu Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Ile Ile Ser
65                  70                  75                  80

Ser Val Gln Ala Glu Asp Glu Ala Asp Tyr Tyr Cys Gly Ala Asp Tyr
                85                  90                  95

Ser Gly Gly Phe Val Phe Gly Gly Gly Thr Gln Leu Thr Val Thr
            100                 105                 110

<210> SEQ ID NO 5
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ser Val Glu Glu Ser Gly Gly Gly Leu Phe Lys Pro Thr Asp Thr
1               5                   10                  15

Leu Thr Leu Thr Cys Thr Val Ser Gly Phe Ser Leu Ser Gly Tyr Gly
                20                  25                  30

Val Ser Trp Val Arg Gln Ala Ala Gly Asn Gly Leu Glu Trp Ile Gly
            35                  40                  45

Ala Ile Ser Ser Gly Gly Ser Ala Tyr Tyr Ala Arg Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Leu Val Met Thr Gln Thr Glu Pro Pro Val Ser Ala Pro Val Gly
1               5                   10                  15

Gly Thr Val Thr Ile Asn Cys Gln Ala Ser Gln Asn Ile Gly Ser Ser
                20                  25                  30

-continued

Tyr Leu Ser Trp Tyr Gln Gln Lys Pro Gly Gln Pro Pro Lys Leu Leu
            35                  40                  45

Ile Tyr Gln Ala Ser Thr Leu Ala Ser Gly Val Pro Ser Arg Phe Lys
 50                  55                  60

Gly Gly Gly Ser Gly Thr Asp Tyr Ser Leu Thr Ile Ser Gly Val Gln
 65                  70                  75                  80

Cys Ala Asp Ala Ala Thr Tyr Tyr Cys Gln Ser Thr Phe Tyr Ser Ser
                85                  90                  95

Gly Thr Gly Tyr Ala Phe Gly Gly Gly Thr Glu Leu Glu Ile Leu
                100                 105                 110

<210> SEQ ID NO 7
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ser Val Lys Glu Ser Glu Gly Gly Leu Phe Lys Pro Thr Asp Thr
1                5                  10                  15

Leu Thr Leu Thr Cys Thr Ala Ser Glu Phe Thr Ile Gly Ser Tyr Ser
                20                  25                  30

Ser Gly Trp Val Arg Gln Ala Pro Gly Lys Glu Leu Glu Trp Ile Gly
            35                  40                  45

Thr Leu Ser Ser Thr Gly Ser Ala His Tyr Ala Asn Trp Ala Lys Gly
 50                  55                  60

Arg Ser Thr Ile Thr Arg Asn Thr Asn Glu Asn Thr Val Thr Leu Lys
65                  70                  75                  80

Met Ala Ser Leu Thr Ala Ala Asp Thr Ala Thr Tyr Phe Cys Ala Arg
                85                  90                  95

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Pro Val Leu Thr Gln Ser Pro Ser Val Ser Ala Ala Leu Gly Ala Ser
1                5                  10                  15

Ala Lys Leu Thr Cys Thr Leu Ser Ser Gly His Lys Thr Tyr Thr Ile
                20                  25                  30

Asp Trp Tyr Gln Gln Gln Gln Gly Glu Ala Pro Arg Tyr Leu Met
            35                  40                  45

Gln Ile Gly Ser Asp Gly Ser Tyr Thr Lys Gly Thr Gly Val Pro Asp
 50                  55                  60

Arg Phe Ser Gly Ser Ser Ser Gly Thr Asp Arg Tyr Leu Ile Ile Ser
65                  70                  75                  80

Ser Val Gln Ala Glu Asp Glu Ala Asp Tyr Tyr Cys Gly Ala Asp Tyr
                85                  90                  95

Ser Gly Gly Phe Val Phe Gly Gly Gly Thr Gln Leu Thr Val Thr
                100                 105                 110

<210> SEQ ID NO 9
<211> LENGTH: 95

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ser Val Glu Glu Ser Gly Gly Gly Leu Phe Lys Pro Thr Asp Thr
1               5                   10                  15

Leu Thr Leu Thr Cys Thr Val Ser Gly Ile Asp Leu Ser Arg Asn Gly
            20                  25                  30

Val Thr Trp Val Arg Gln Ala Pro Gly Ser Gly Leu Glu Trp Ile Gly
        35                  40                  45

Val Ile Asn Ser His Gly Asp Ser Asp Tyr Ala Thr Trp Ala Asn Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala
                85                  90                  95

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Leu Val Met Thr Gln Thr Pro Ser Ser Val Ser Ala Ala Val Gly
1               5                   10                  15

Gly Thr Val Thr Ile Asn Cys Gln Ala Ser Gln Thr Ile Asn Asn Leu
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Gln Phe Ile Leu Thr Ile Ser Gly Met Lys Ala
65                  70                  75                  80

Glu Asp Ala Ala Thr Tyr Tyr Cys Gln Ser Ala Tyr Tyr Asn Ala Gly
                85                  90                  95

Ala Thr Phe Gly Ala Gly Thr Asn Val Glu Ile Lys
            100                 105

<210> SEQ ID NO 11
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ser Leu Glu Glu Ser Gly Gly Gly Leu Phe Lys Pro Thr Asp Thr
1               5                   10                  15

Leu Thr Leu Thr Cys Thr Val Ser Gly Phe Ser Leu Ser Asn Ser Ala
            20                  25                  30

Met Ser Trp Val Arg Gln Ala Pro Gly Asn Gly Leu Glu Trp Ile Gly
        35                  40                  45

Asp Ile Asp Ser Ser Gly Ser Ala Tyr Tyr Ala Ser Trp Ala Lys Ser

```
Arg Ser Thr Ile Thr Arg Asn Thr Asn Leu Asn Thr Val Thr Leu Lys
 65                  70                  75                  80

Met Thr Ser Leu Thr Ala Ala Asp Thr Ala Thr Tyr Phe Cys Ala Arg
                 85                  90                  95
```

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Pro Val Leu Thr Gln Ser Pro Ser Val Ser Ala Ala Leu Gly Ala Ser
  1               5                  10                  15

Ala Lys Phe Thr Cys Thr Leu Ser Ser Gly His Lys Thr Tyr Thr Ile
                 20                  25                  30

Asp Trp Tyr Gln Gln Gln Gln Gly Glu Ala Pro Arg Tyr Leu Met
             35                  40                  45

Gln Ile Gly Ser Asp Gly Ser Tyr Thr Lys Gly Thr Gly Val Pro Asp
     50                  55                  60

Arg Phe Ser Gly Ser Ser Ser Gly Thr Asp Arg Tyr Leu Ile Ile Ser
 65                  70                  75                  80

Ser Val Gln Ala Glu Asp Glu Ala Asp Tyr Ile Cys Gly Val Thr Gly
                 85                  90                  95

Ser Asn Val Tyr Ala Gln Asp Pro Ala Asp Arg His
                100                 105
```

<210> SEQ ID NO 13
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Ser Leu Glu Glu Ser Gly Gly Gly Leu Phe Lys Pro Thr Asp Thr
  1               5                  10                  15

Leu Thr Leu Thr Cys Thr Val Ser Gly Phe Asp Ile Ser Gly Val Tyr
                 20                  25                  30

Met Ser Trp Val Arg Gln Ala Pro Gly Asn Gly Leu Glu Trp Ile Gly
             35                  40                  45

Ala Ile Asp Arg Gly Gly Gly Thr Tyr Tyr Ala Ser Trp Ala Ile Gly
     50                  55                  60

Arg Ser Thr Ile Thr Arg Asn Thr Asn Asp Asn Thr Val Thr Leu Glu
 65                  70                  75                  80

Met Thr Ser Leu Thr Ala Ala Asp Thr Ala Thr Tyr Phe Cys Ala Lys
                 85                  90                  95
```

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Leu Val Met Thr Gln Thr Pro Ser Ser Val Ser Ala Ala Val Gly
1               5                   10                  15

Gly Thr Val Thr Ile Asn Cys Gln Ala Ser Glu Ser Ile Ser Asn Tyr
                20                  25                  30

Leu Ala Trp Tyr Gln Gln Lys Pro Gly Gln Pro Pro Lys Leu Leu Thr
            35                  40                  45

Tyr Asp Ala Ser Asp Leu Ala Ser Gly Val Pro Ser Arg Phe Ser Gly
50                  55                  60

Ser Gly Tyr Gly Thr Glu Phe Thr Leu Thr Ile Ser Gly Val Lys Ala
65                  70                  75                  80

Glu Asp Ala Ala Thr Tyr Tyr Cys Gln Ser Gly Tyr Val Ser Ala Gly
                85                  90                  95

Thr Phe Gly Ala Gly Thr Asn Val Glu Ile Lys
            100                 105

<210> SEQ ID NO 15
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Leu Glu Glu Ser Gly Gly Gly Leu Ile Lys Pro Thr Asp Met
1               5                   10                  15

Leu Thr Leu Thr Cys Thr Val Ser Gly Phe Ser Leu Ser Asn Tyr Gly
                20                  25                  30

Val Met Trp Val Arg Gln Ala Pro Gly Asn Gly Leu Glu Ser Ile Gly
            35                  40                  45

Tyr Ile Gly Ser Gly Gly Asp Thr Ser Tyr Ala Ser Trp Ala Lys Ser
50                  55                  60

Arg Ser Thr Ile Ala Arg Asn Thr Asn Glu Asn Thr Val Ser Leu Leu
65                  70                  75                  80

Met Asn Gly Leu Thr Ala Ala Asp Thr Ala Thr Tyr Phe Cys Ala Arg
                85                  90                  95

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Pro Val Leu Thr Gln Ser Pro Ser Val Ser Ala Ala Leu Gly Ala
1               5                   10                  15

Ser Ala Lys Leu Thr Cys Thr Leu Ser Ser Ala His Lys Thr Tyr Thr
                20                  25                  30

Ile Asp Trp Tyr Gln Gln Gln Gly Glu Ala Pro Arg Tyr Leu Met
            35                  40                  45

His Leu Lys Ser Asp Gly Thr Tyr Thr Lys Gly Thr Gly Val Pro Asp
50                  55                  60

Arg Phe Ser Gly Ser Ser Ser Gly Ala Asp Arg Tyr Leu Ile Ile Pro
65                  70                  75                  80

Ser Val Arg Thr Asp Asp Glu Ala Asp Tyr Tyr Cys Gly Thr Asp Tyr
                85                  90                  95

Ser Gly Gly Tyr Val Phe Gly Gly Thr Gln Leu Thr Val Thr
            100                 105                 110

<210> SEQ ID NO 17
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ser Leu Glu Glu Ser Gly Gly Leu Phe Lys Pro Thr Asp Thr
1               5                   10                  15

Leu Thr Leu Thr Cys Thr Val Ser Gly Phe Ser Leu Ser Ile Tyr Gly
                20                  25                  30

Val Ser Trp Val Arg Gln Ala Pro Gly Asn Gly Leu Glu Trp Val Gly
                35                  40                  45

Ala Ile Gly Ser Gly Gly Ser Ala Tyr Tyr Ala Thr Trp Ala Lys Ser
            50                  55                  60

Arg Ser Thr Ile Thr Arg Asn Thr Asn Leu Asn Thr Val Thr Leu Lys
65              70                  75                  80

Met Ala Ser Leu Thr Ala Ala Asp Thr Ala Thr Tyr Phe Cys Ala Arg
                85                  90                  95

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Pro Val Leu Thr Gln Ser Pro Ser Ala Ser Ala Ala Leu Gly Ser
1               5                   10                  15

Ser Ala Lys Leu Thr Cys Thr Leu Ser Ser Ala His Lys Thr Tyr Tyr
                20                  25                  30

Ile Asp Trp Tyr Gln Gln Gln Gly Glu Ala Pro Arg Tyr Leu Met
                35                  40                  45

Gln Val Lys Ser Asp Gly Ser Tyr Thr Arg Gly Thr Gly Val Pro Asp
            50                  55                  60

Arg Phe Ser Gly Ser Ser Ser Gly Ala Asp Arg Tyr Leu Ile Ile Pro
65              70                  75                  80

Ser Val Gln Ala Asp Asp Glu Ala Asp Tyr Tyr Cys Gly Ser Asp Tyr
                85                  90                  95

Ser Gly Gly Tyr Val Phe Gly Gly Thr Gln Leu Thr Val Thr
            100                 105                 110

<210> SEQ ID NO 19
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ser Val Glu Glu Ser Arg Gly Gly Leu Phe Lys Pro Thr Asp Thr
1               5                   10                  15

```
Leu Thr Leu Thr Cys Thr Val Ser Gly Phe Ser Leu Ser Thr Tyr Asn
            20                  25                  30

Ile Gln Trp Val Arg Gln Ala Pro Gly Asn Gly Leu Glu Tyr Ile Gly
            35                  40                  45

Thr Ile Gly Ser Ser Gly Ser Ala Tyr Tyr Ala Ser Arg Ala Lys Ser
            50                  55                  60

Arg Ser Thr Ile Thr Arg Asn Thr Ala Leu Asn Thr Val Ser Leu Gln
 65                  70                  75                  80

Val Asp Ser Leu Thr Asp Ala Asp Thr Ala Thr Tyr Phe Cys Ala Arg
            85                  90                  95

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Leu Asp Leu Thr Gln Thr Pro Ser Ser Val Ser Ala Ala Val Gly
 1               5                  10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
            35                  40                  45

Tyr Gly Ala Ser Asn Leu Glu Ser Gly Val Pro Ser Arg Phe Arg Gly
            50                  55                  60

Ser Gly Ser Gly Thr Glu Phe Thr Leu Thr Ile Ser Asp Val Val Cys
 65                  70                  75                  80

Asp Asp Ala Ala Thr Tyr Tyr Cys Ala Gly His Lys Ser Ser Ser Thr
            85                  90                  95

Asp Gly Thr Ala Phe Gly Gly Gly Thr Glu Leu Glu Ile Leu
            100                 105                 110

<210> SEQ ID NO 21
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Ser Val Lys Glu Ser Glu Gly Gly Leu Phe Lys Pro Thr Asp Thr
 1               5                  10                  15

Leu Thr Leu Thr Cys Thr Val Ser Gly Phe Thr Val Ser Asn Asn Ala
            20                  25                  30

Ile Ser Trp Val Arg Gln Ala Pro Gly Asn Gly Leu Glu Trp Ile Gly
            35                  40                  45

Ala Ile Ser Tyr Gly Gly Asn Thr Tyr Tyr Ala Asn Trp Pro Lys Ser
            50                  55                  60

Arg Ser Thr Ile Thr Arg Asn Thr Asn Leu Asn Thr Val Thr Leu Lys
 65                  70                  75                  80

Met Thr Ser Leu Thr Ala Ala Asp Thr Ala Thr Tyr Phe Cys Ala Arg
            85                  90                  95

<210> SEQ ID NO 22
<211> LENGTH: 111
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Pro Val Leu Thr Gln Ser Pro Ser Ala Ser Ala Ala Leu Gly Ser
1               5                   10                  15

Ser Ala Lys Leu Thr Cys Thr Leu Ser Ser Ala His Lys Thr Tyr Tyr
                20                  25                  30

Ile Asp Trp Tyr Gln Gln Gln Gly Glu Ala Pro Arg Tyr Leu Met
            35                  40                  45

Gln Val Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ser Asp Tyr
                85                  90                  95

Ser Gly Gly Tyr Val Phe Gly Gly Gly Ala Gln Leu Thr Val Thr
            100                 105                 110

<210> SEQ ID NO 23
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Asn Tyr Gly
                20                  25                  30

Val Ser Trp Val Arg Gln Ala Pro Gly Lys Glu Val Glu Trp Ile Gly
            35                  40                  45

Tyr Ile Asn Ser Gly Gly Ser Thr Asn Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Leu Asp Met Thr Gln Thr Pro Ser Ser Val Ser Ala Ala Val Gly
1               5                   10                  15

Asp Thr Val Thr Ile Asn Cys Gln Ala Ser Gln Ser Val Thr Asn Leu
                20                  25                  30

Leu Ala Trp Tyr Gln Gln Lys Pro Arg Gln Pro Pro Lys Leu Leu Ile
            35                  40                  45

Tyr Asp Ala Ser Asn Leu Glu Ser Gly Val Pro Ser Arg Phe Arg Gly
```

```
                  50                  55                  60
Ser Gly Ser Gly Thr Glu Phe Thr Leu Thr Ile Ser Gly Met Lys Ala
 65                  70                  75                  80

Glu Asp Ala Ala Thr Tyr Tyr Cys Gln Ser Gly Tyr Tyr Ser Ala Gly
                 85                  90                  95

Ala Thr Phe Gly Ala Gly Thr Asn Val Glu Ile Lys
                100                 105
```

<210> SEQ ID NO 25
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Ser Val Lys Glu Ser Glu Gly Gly Leu Phe Lys Pro Met Asp Ser
 1               5                  10                  15

Met Thr Leu Thr Cys Thr Val Ser Gly Phe Ser Leu Ser Ser Tyr Gly
                 20                  25                  30

Val Ser Trp Val Arg Gln Ala Pro Gly Asn Gly Leu Glu Trp Ile Gly
                 35                  40                  45

Ala Ile Ser Ser Gly Gly Ser Ala Tyr Tyr Ala Arg Trp Ala Lys Ser
                 50                  55                  60

Arg Ala Thr Ile Thr Arg Asn Thr Asn Leu Asn Thr Val Thr Leu Lys
 65                  70                  75                  80

Met Ala Ser Leu Thr Ala Ala Asp Thr Ala Thr Tyr Phe Cys Ala Arg
                 85                  90                  95
```

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Glu Leu Val Leu Thr Gln Thr Pro Ser Pro Val Ser Ala Ala Val Gly
 1               5                  10                  15

Gly Thr Val Thr Ile Asn Cys Gln Ser Ser Gln Ser Val Tyr Ser Asn
                 20                  25                  30

Asn Arg Leu Ala Trp Tyr Gln Gln Lys Pro Gly Gln Pro Pro Lys Gln
                 35                  40                  45

Leu Ile Tyr Tyr Ala Ser Thr Leu Ala Ser Gly Val Ser Ser Arg Phe
                 50                  55                  60

Lys Gly Ser Gly Ser Gly Thr Gln Phe Thr Leu Thr Ile Ser Asp Val
 65                  70                  75                  80

Val Cys Asp Asp Ala Ala Thr Tyr Tyr Cys Ala Gly Tyr Lys Asn Ser
                 85                  90                  95

Gly Ile Asp Glu His Ala Phe Gly Gly Gly Thr Glu Leu Glu Ile Leu
                100                 105                 110
```

<210> SEQ ID NO 27
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Gln Ser Leu Glu Glu Ser Gly Gly Gly Leu Phe Lys Pro Thr Asp Thr
1               5                   10                  15
Leu Thr Leu Thr Cys Thr Val Ser Gly Phe Ser Leu Asn Arg Tyr Asp
            20                  25                  30
Met Ser Trp Val Arg Gln Ala Pro Gly Asn Gly Leu Glu Trp Ile Gly
        35                  40                  45
Val Ile Asn Ser Gly Gly Phe Thr Tyr Tyr Ala Ser Trp Ala Lys Ser
    50                  55                  60
Arg Ser Thr Ile Thr Arg Asn Thr Asn Glu Asn Thr Val Thr Leu Lys
65                  70                  75                  80
Met Thr Ser Leu Thr Ala Ala Asp Thr Ala Thr Tyr Phe Cys Ala Arg
                85                  90                  95

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Pro Val Leu Thr Gln Ser Pro Ser Val Ser Ala Ala Leu Gly Ala
1               5                   10                  15
Ser Ala Lys Leu Thr Cys Thr Leu Ser Ser Gly His Lys Thr Tyr Thr
            20                  25                  30
Ile Asp Trp Tyr Gln Gln Gln Gly Glu Ala Pro Arg Tyr Leu Met Gln
        35                  40                  45
Gln Leu Gly Ser Asp Gly Ser Tyr Thr Lys Gln Thr Gly Val Pro Asp
    50                  55                  60
Arg Phe Ser Gly Ser Ser Ser Gly Ala Asp Arg Tyr Leu Ile Ile Ser
65                  70                  75                  80
Ser Val Gln Ala Asp Asp Glu Ala Asp Tyr Tyr Cys Gly Ala Asp Tyr
                85                  90                  95
Ser Gly Gly Phe Val Phe Gly Gly Gly Thr Gln Leu Thr Val Thr
            100                 105                 110

<210> SEQ ID NO 29
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ser Val Lys Glu Ser Glu Gly Gly Leu Phe Lys Pro Thr Asp Thr
1               5                   10                  15
Leu Thr Leu Thr Cys Thr Val Ser Gly Phe Ser Leu Ser Asn Asn Ala
            20                  25                  30
Ile Asn Trp Val Arg Gln Ala Pro Gly Asn Gly Leu Glu Trp Ile Gly
        35                  40                  45
Ala Val Gly Ser Gly Gly Arg Ala Tyr Tyr Ala Gly Trp Ala Lys Ser
    50                  55                  60
Arg Ser Thr Ile Thr Arg Asn Thr Asn Leu Asn Thr Val Thr Leu Lys
65                  70                  75                  80

```
Met Thr Asn Leu Thr Ala Ala Asp Thr Ala Thr Tyr Phe Cys Ala Arg
                85                  90                  95
```

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Leu Val Leu Thr Gln Thr Pro Ser Ser Val Ser Ala Ala Val Gly
1               5                   10                  15

Gly Thr Val Ser Ile Ser Cys Gln Ser Ser Gln Ser Val Tyr Ser Asn
            20                  25                  30

Tyr Leu Ala Trp Tyr Gln Gln Lys Pro Gly Gln Pro Pro Lys Leu Leu
        35                  40                  45

Ile Tyr Tyr Ala Ser Thr Leu Ala Ser Gly Val Ser Ser Arg Phe Lys
    50                  55                  60

Gly Ser Gly Ser Gly Thr Gln Phe Thr Leu Thr Ile Asn Gly Val Gln
65                  70                  75                  80

Cys Asp Asp Ala Ala Thr Tyr Tyr Cys Gln Gly Thr Phe Asp Asp Gly
                85                  90                  95

Leu Tyr Lys Ala Phe Gly Gly Gly Thr Glu Leu Glu Ile Leu
            100                 105                 110
```

<210> SEQ ID NO 31
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Ser Leu Glu Glu Ser Gly Gly Gly Leu Phe Lys Pro Thr Asp Thr
1               5                   10                  15

Leu Thr Leu Thr Cys Thr Val Ser Gly Phe Ser Leu Ser Asn Tyr Gly
            20                  25                  30

Met Gly Trp Val Arg Gln Ala Pro Gly Asn Gly Leu Glu Tyr Ile Gly
        35                  40                  45

Phe Ile Ser Ser Gly Gly Asn Thr Tyr Tyr Ala Ser Trp Ala Lys Ser
    50                  55                  60

Arg Ser Thr Ile Thr Arg Asp Thr Asn Leu Asn Thr Val Thr Leu Lys
65                  70                  75                  80

Met Ser Ser Leu Thr Ala Ala Asp Thr Ala Thr Tyr Phe Cys Ala Arg
                85                  90                  95
```

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Glu Leu Val Met Thr Gln Thr Pro Ser Ser Val Ser Ala Ala Val Gly
1               5                   10                  15
```

```
Gly Thr Val Thr Ile Asn Cys Gln Ala Ser Gln Ser Val Tyr Asn Leu
            20                  25                  30

Leu Ala Trp Tyr Gln Gln Lys Pro Gly Gln Pro Pro Lys Leu Leu Thr
        35                  40                  45

His Gly Thr Ser Asn Leu Glu Ser Gly Val Pro Ser Arg Phe Arg Gly
50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Thr Gly
                85                  90                  95

Ala Thr Phe Gly Ala Gly Thr Asn Val Glu Ile Lys
            100                 105
```

<210> SEQ ID NO 33
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Ser Leu Glu Glu Ser Gly Gly Gly Leu Phe Lys Pro Thr Asp Pro
1               5                   10                  15

Leu Thr Leu Thr Cys Thr Val Ser Gly Phe Ser Ile Asn Asp Tyr Asn
            20                  25                  30

Met Gln Trp Val Arg Gln Ala Pro Gly Ile Gly Leu Glu Trp Ile Gly
        35                  40                  45

Ala Ile Asn Ala Trp Gly Asp Thr Tyr Tyr Thr Ser Trp Ala Lys Ser
50                  55                  60

Arg Ser Thr Ile Thr Arg Asp Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95
```

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Glu Leu Asp Leu Thr Gln Thr Pro Ser Ser Val Ser Ala Ala Val Gly
1               5                   10                  15

Gly Thr Val Thr Ile Asn Cys Gln Ser Ser Gln Ser Val Asp Ser Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Thr Leu Ala Ser Gly Val Pro Ser Arg Phe
50                  55                  60

Ser Gly Ser Gly Ser Gly Thr Gln Phe Thr Leu Thr Ile Ser Glu Val
65                  70                  75                  80

Gln Cys Asp Asp Ala Ala Thr Tyr Tyr Cys Gln Gly Ser Tyr Tyr Ser
                85                  90                  95

Gly Asp Trp Tyr Gly Ala Phe Gly Gly Gly Thr Glu Leu Glu Ile Leu
            100                 105                 110
```

```
<210> SEQ ID NO 35
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ser Leu Glu Glu Ser Gly Gly Gly Leu Phe Lys Pro Thr Asp Thr
1               5                   10                  15

Leu Thr Leu Thr Cys Thr Ala Ser Gly Phe Thr Val Thr Ser Asn Ala
            20                  25                  30

Ile Ser Trp Val Arg Gln Ala Pro Gly Asn Gly Leu Glu Tyr Ile Gly
        35                  40                  45

Phe Ile Gly Ala Ala Gly Asn Ala Asn Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Leu Val Met Thr Gln Thr Pro Ala Ser Val Ser Glu Pro Val Gly
1               5                   10                  15

Gly Thr Val Thr Ile Ser Cys Gln Ala Ser Gln Gly Val Tyr Ser Asp
            20                  25                  30

Arg Leu Ala Trp Tyr Gln Gln Lys Pro Gly Gln Pro Pro Lys Leu Leu
        35                  40                  45

Met Tyr Tyr Ala Ser Asp Leu Ser Ser Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Ser Asn Tyr Gly Ser Leu
                85                  90                  95

Ser Ser Ser Tyr Thr Phe Gly Gly Gly Thr Glu Val Val Val Lys
                100                 105                 110

<210> SEQ ID NO 37
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ser Val Glu Glu Ser Arg Gly Gly Leu Phe Lys Pro Thr Asp Thr
1               5                   10                  15

Leu Thr Leu Thr Cys Thr Val Ser Gly Phe Thr Ile Asp Thr Tyr Gly
            20                  25                  30

Val Thr Trp Val Arg Gln Ala Pro Gly Asn Gly Leu Glu Tyr Ile Gly
```

```
                35                  40                  45
Phe Ile Ser Ser Gly Gly Ala Ala Tyr Tyr Ala Ser Trp Ala Lys Ser
 50                  55                  60

Arg Ser Thr Ile Thr Arg Asn Thr Asn Leu Asn Val Thr Leu Lys
 65                  70                  75              80

Met Thr Ser Leu Thr Ala Ala Asp Thr Ala Thr Tyr Phe Cys Ala Arg
                 85                  90                  95
```

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 38

```
Glu Leu Val Met Thr Gln Thr Pro Pro Ser Leu Ser Ala Ser Val Gly
 1               5                  10                  15

Glu Thr Val Arg Ile Arg Cys Leu Ala Ser Glu Asn Val Tyr Ser Ala
                 20                  25                  30

Val Ala Trp Tyr Gln Gln Lys Pro Gly Lys Pro Pro Thr Leu Leu Ile
             35                  40                  45

Ser Gly Ala Ser Asn Leu Glu Ser Gly Val Pro Pro Arg Phe Ser Gly
 50                  55                  60

Ser Gly Ser Gly Thr Asp Tyr Thr Leu Thr Ile Gly Gly Val Gln Ala
 65                  70                  75              80

Glu Asp Ala Ala Thr Tyr Phe Cys Gln Gly Tyr Ser Ser Tyr Leu Thr
                 85                  90                  95

Phe Gly Ala Gly Thr Asn Val Glu Ile Lys
            100                 105
```

<210> SEQ ID NO 39
<211> LENGTH: 96
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 39

```
Gln Ser Leu Glu Glu Ser Gly Gly Gly Leu Ile Lys Pro Thr Asp Thr
 1               5                  10                  15

Leu Thr Leu Thr Cys Thr Val Ser Gly Phe Ser Leu Ser Ile Tyr Asp
                 20                  25                  30

Ile Ser Trp Val Arg Gln Ala Pro Gly Asn Gly Leu Glu Trp Ile Gly
             35                  40                  45

Ala Ile Gly Ser Gly Asp Thr Thr Tyr Tyr Ala Ser Trp Ala Lys Ser
 50                  55                  60

Arg Ser Thr Ile Thr Arg Asn Thr Tyr Leu Asn Thr Val Thr Leu Lys
 65                  70                  75              80

Met Thr Ser Leu Thr Ala Ala Asp Thr Ala Thr Tyr Phe Cys Ala Arg
                 85                  90                  95
```

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Gln Pro Val Leu Thr Gln Ser Pro Ser Ala Ser Ala Leu Arg Ser
1               5                   10                  15

Ser Ala Lys Leu Thr Cys Thr Leu Ser Ser Ala His Lys Ser Tyr Asp
                20                  25                  30

Ile Asp Trp Tyr Gln Gln Ser Gly Glu Ala Pro Arg Tyr Leu Met
            35                  40                  45

Arg Leu Arg Ser Asp Gly Lys Tyr Thr Lys Gly Thr Gly Val Pro Asp
50                  55                  60

Arg Phe Ser Gly Ser Ser Ser Gly Ala Asp Arg Tyr Leu Ile Ile Pro
65                  70                  75                  80

Ser Val Gln Ala Asp Asp Gly Ala Asp Tyr Tyr Cys Gly Thr Asp Tyr
                85                  90                  95

Ser Gly Gly Tyr Val Phe Gly Gly Gly Thr Gln Leu Thr Val Thr
            100                 105                 110
```

<210> SEQ ID NO 41
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Glu Gln Leu Val Glu Ser Gly Gly Leu Phe Lys Pro Thr Asp Thr
1               5                   10                  15

Leu Thr Leu Thr Cys Thr Val Ser Gly Phe Ser Leu Asn Asn Tyr Gly
                20                  25                  30

Val Thr Trp Val Arg Gln Ala Pro Gly Arg Gly Leu Glu Trp Ile Gly
            35                  40                  45

Ala Val Trp Ser Gly Ala Thr Thr Asp Tyr Ala Ser Trp Ala Lys Ser
50                  55                  60

Arg Ser Thr Ile Thr Arg Asn Thr Asn Glu Asn Thr Val Thr Leu Lys
65                  70                  75                  80

Met Ser Ser Leu Thr Ala Ala Asp Thr Ala Thr Tyr Phe Cys Ala
                85                  90                  95
```

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Glu Leu Val Met Thr Gln Thr Glu Ser Pro Val Ser Ala Ala Val Gly
1               5                   10                  15

Gly Thr Val Thr Ile Asn Cys Gln Ala Ser Gln Ser Ile Ser Ser Trp
                20                  25                  30

Leu Ala Trp Tyr Gln Gln Lys Pro Gly Lys Pro Pro Thr Leu Leu Ile
            35                  40                  45

Ser Gly Ala Ser Asn Leu Glu Ser Gly Val Pro Pro Arg Phe Ser Gly
50                  55                  60

Ser Gly Ser Gly Thr Asp Tyr Thr Leu Thr Ile Gly Gly Val Gln Ala
65                  70                  75                  80
```

```
Glu Asp Ala Ala Thr Tyr Tyr Cys Leu Gly Gly Tyr Ser Tyr Ser Ser
                85                  90                  95

Ile Gly Thr Thr Phe Gly Ala Gly Thr Asn Val Glu Ile Lys
                100                 105                 110

<210> SEQ ID NO 43
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Glu Gln Leu Glu Glu Ser Gly Gly Gly Leu Val Gln Pro Gly Gly
1               5                   10                  15

Ser Leu Lys Leu Ser Cys Lys Ala Ser Gly Phe Asp Phe Ile Asn Tyr
                20                  25                  30

Gly Val Ile Trp Val Arg Gln Ala Pro Gly Lys Gly Leu Glu Trp Ile
            35                  40                  45

Gly Tyr Ile Asp Pro Ile Phe Gly Asn Thr Ile Tyr Ala Ser Trp Val
        50                  55                  60

Asn Asp Arg Phe Thr Ile Ser Ser His Asn Ala Gln Asn Thr Leu Tyr
65                  70                  75                  80

Leu Gln Leu Asn Ser Leu Thr Ala Ala Asp Thr Ala Thr Tyr Phe Cys
                85                  90                  95

Ala Arg

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Leu Val Met Thr Gln Thr Pro Ser Ser Val Ser Ala Ala Val Gly
1               5                   10                  15

Gly Thr Val Thr Ile Asn Cys Gln Ala Ser Gln Ser Val Asn Asn Leu
                20                  25                  30

Leu Ala Trp Tyr Gln Gln Lys Pro Gly Gln Pro Pro Lys Leu Leu Thr
            35                  40                  45

Tyr Gly Thr Ser Asn Leu Glu Ser Gly Val Pro Ser Arg Phe Arg Gly
        50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Ala Gly
                85                  90                  95

Leu Thr Phe Gly Ala Gly Thr Asn Val Glu Ile Lys
                100                 105

<210> SEQ ID NO 45
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 45

Gln Ser Leu Glu Glu Ser Gly Gly Leu Ile Lys Pro Thr Asp Thr
1               5                   10                  15

Leu Thr Leu Thr Cys Thr Val Ser Gly Phe Ser Leu Ser Thr Asn Gly
            20                  25                  30

Val Ser Trp Val Arg Gln Ala Pro Gly Ser Gly Leu Glu Trp Ile Gly
        35                  40                  45

Ala Ile Asp Leu Tyr Gly Ala Thr Tyr Tyr Ala Thr Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Leu Val Leu Thr Gln Thr Pro Ala Ser Val Ser Glu Pro Val Gly
1               5                   10                  15

Gly Thr Val Thr Ile Lys Cys Gln Ala Ser Gln Asn Ile Tyr Ser Gly
            20                  25                  30

Ile Ser Trp Tyr Gln Gln Lys Pro Glu Lys Pro Pro Thr Leu Leu Ile
        35                  40                  45

Ser Gly Ala Ser Asn Leu Glu Pro Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Gly Asp Ala Ala Thr Tyr Tyr Cys Leu Gly Val Tyr Ser Phe Gly Ser
                85                  90                  95

Thr Asp Leu Thr Phe Gly Ala Gly Thr Asn Val Glu Ile Lys
                100                 105                 110

<210> SEQ ID NO 47
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ser Leu Glu Glu Ser Gly Gly Gly Leu Phe Lys Pro Thr Asp Thr
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Asn Gly Leu Glu Trp Ile Gly
        35                  40                  45

Tyr Ile Asn Tyr Asp Gly Ile Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Gly Leu Thr Ala Ala Asp Thr Ala Thr Tyr Phe Cys Ala Arg

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Leu Asp Leu Thr Gln Thr Pro Ser Ser Val Ser Ala Ala Val Gly
1               5                   10                  15

Gly Thr Val Ser Ile Ser Cys Gln Ser Ser Gln Ser Val Tyr Asn Asn
            20                  25                  30

Tyr Leu Ala Trp Tyr Gln Gln Lys Pro Gly Gln Pro Pro Lys Leu Leu
        35                  40                  45

Ile Tyr Tyr Ala Ser Lys Leu Ala Ser Gly Val Pro Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Gln Gly Thr Phe Asp Asn Gly
                85                  90                  95

Leu Tyr Lys Ala Phe Gly Gly Gly Thr Glu Leu Glu Ile Leu
            100                 105                 110

<210> SEQ ID NO 49
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ser Leu Glu Glu Ser Gly Gly Gly Leu Val Gln Pro Gly Gly Ser
1               5                   10                  15

Leu Lys Leu Ser Cys Lys Gly Ser Gly Phe Asp Leu Asp Ser Asn Ala
            20                  25                  30

Met Cys Trp Val Arg Gln Ala Pro Gly Ser Gly Leu Glu Trp Ile Gly
        35                  40                  45

Thr Ile Thr Ser Gly Gly Ser Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 50
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Leu Asp Met Thr Gln Thr Pro Ser Ser Val Ser Ala Ala Val Gly
1               5                   10                  15

Gly Thr Val Thr Ile Asn Cys Gln Ala Ser Glu Ser Ile Ser Asn Leu
            20                  25                  30

Leu Ala Trp Tyr Gln Gln Lys Pro Gly Gln Pro Pro Lys Leu Leu Ile
            35                  40                  45

Tyr Ser Ala Ser Thr Leu Ala Ser Gly Val Pro Ser Arg Phe Arg Gly
        50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Ser Thr Gly
                85                  90                  95

Ala Thr Phe Gly Ala Gly Thr Asn Val Glu Ile Lys
            100                 105

<210> SEQ ID NO 51
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Glu Gln Leu Glu Glu Ser Gly Gly Arg Leu Val Lys Pro Asp Glu
1               5                   10                  15

Thr Leu Thr Leu Thr Cys Thr Val Ser Gly Leu Ser Leu Asn Asn Phe
            20                  25                  30

Gly Val Ser Trp Val Arg Gln Ala Pro Gly Asn Gly Leu Glu Trp Ile
        35                  40                  45

Arg Ala Ile Asp Phe Gly Ser Gly Ser Ala Tyr Tyr Ala Asn Trp Ala
    50                  55                  60

Lys Ser Arg Ser Thr Ile Thr Ser Asn Thr Arg Leu Asn Thr Val Thr
65                  70                  75                  80

Leu Lys Met Ile Ser Leu Thr Ala Ala Asp Thr Ala Thr Tyr Phe Cys
                85                  90                  95

Ser Arg

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Pro Val Leu Thr Gln Ser Pro Ser Val Ser Ala Ala Leu Gly Ala
1               5                   10                  15

Ser Ala Lys Leu Thr Cys Thr Leu Ser Ser Ala His Lys Thr Tyr Thr
            20                  25                  30

Ile Asp Trp Tyr Gln Gln Ser Gly Glu Ala Pro Arg Tyr Leu Met
        35                  40                  45

Gln Leu Lys Ser Asp Gly Asn Tyr Thr Lys Gly Thr Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ser Gly Gly Tyr Val Phe Gly Gly Gly Thr Gln Leu Thr Val Thr
            100                 105                 110

```
<210> SEQ ID NO 53
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Asn Tyr Ala
            20                  25                  30

Ile Asn Trp Val Arg Gln Ala Pro Gly Glu Gly Leu Glu Trp Ile Gly
        35                  40                  45

Tyr Ile Asp Pro Thr Phe Gly Ser Thr Tyr Tyr Ala Ser Trp Val Asn
    50                  55                  60

Asp Arg Phe Thr Ile Ser Ser His Asn Ala Gln Asn Thr Leu Tyr Leu
65                  70                  75                  80

Gln Leu Asn Ser Leu Thr Pro Ala Asp Thr Ala Thr Tyr Phe Cys Ala
                85                  90                  95

Arg

<210> SEQ ID NO 54
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Leu Asp Met Thr Gln Thr Pro Ser Ser Val Ser Ala Ala Val Gly
1               5                   10                  15

Gly Thr Val Thr Ile Ser Cys Gln Ala Ser Gln Ser Val Tyr Asn Asn
            20                  25                  30

Asn Asn Leu Ser Trp Tyr Gln Gln Lys Pro Gly Gln Pro Pro Lys Leu
        35                  40                  45

Leu Ile Tyr Asp Ala Ser Lys Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asn Ala Ala Thr Tyr Phe Cys Gln Gln Gly Tyr Asp Gly
                85                  90                  95

Ser Asp Val Asp Asn Val Phe Gly Gly Gly Thr Glu Val Val Val Lys
                100                 105                 110

<210> SEQ ID NO 55
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Ser Leu Glu Glu Ser Gly Gly Gly Leu Phe Lys Pro Gly Gly Ser
1               5                   10                  15

Leu Thr Leu Thr Cys Thr Val Ser Gly Phe Thr Ile Thr Ser Tyr His
            20                  25                  30
```

```
Met Cys Trp Val Arg Gln Ala Pro Gly Asn Gly Leu Gly Trp Ile Gly
        35                  40                  45

Ala Val Ser Ala Ser Gly His Thr Tyr Tyr Ala Asn Trp Ala Lys Ser
 50                  55                  60

Arg Ser Thr Ile Thr Arg Asp Thr Asn Leu Asn Thr Met Thr Leu Lys
 65                  70                  75                  80

Met Thr Ser Leu Thr Ala Ala Asp Thr Ala Thr Tyr Phe Cys Ala
                 85                  90                  95

<210> SEQ ID NO 56
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Leu Val Leu Thr Gln Thr Pro Pro Ser Leu Ser Ala Ser Val Gly
 1               5                  10                  15

Glu Thr Val Arg Ile Arg Cys Leu Ala Ser Glu Phe Leu Phe Asn Ala
                20                  25                  30

Val Ser Trp Tyr Gln Gln Lys Pro Glu Lys Pro Pro Thr Leu Pro Ile
        35                  40                  45

Tyr Gly Ala Ser Asn Leu Glu Ser Gly Val Pro Pro Arg Phe Ser Gly
 50                  55                  60

Ser Gly Ser Gly Thr Gln Phe Thr Leu Thr Ile Ser Asp Leu Glu Cys
 65                  70                  75                  80

Asp Asp Ala Ala Thr Tyr Tyr Cys Ala Gly Asp Tyr Ser Asp Trp Ile
                 85                  90                  95

Tyr Ala Phe Gly Gly Gly Thr Glu Val Val Lys
                100                 105

<210> SEQ ID NO 57
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ser Leu Glu Glu Ser Gly Gly Leu Phe Lys Pro Thr Asp Thr
 1               5                  10                  15

Leu Thr Leu Thr Cys Thr Val Ser Gly Phe Ser Leu Ser Ser Tyr Gly
                20                  25                  30

Ile Thr Trp Val Arg Gln Ala Pro Gly Asn Gly Leu Glu Trp Ile Gly
        35                  40                  45

Ala Ile Gly Ser Asp Ala Lys Thr Tyr Tyr Ala Ser Trp Ala Lys Gly
 50                  55                  60

Arg Ser Thr Ile Thr Gly Asp Thr Asn Leu Asn Thr Val Thr Leu Arg
 65                  70                  75                  80

Met Thr Ser Leu Thr Ala Ala Asp Thr Ala Thr Tyr Phe Cys Ala Arg
                 85                  90                  95

<210> SEQ ID NO 58
<211> LENGTH: 112
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 58

Glu Leu Val Leu Thr Gln Thr Pro Ser Ser Val Pro Ala Ala Val Gly
1               5                   10                  15

Gly Thr Val Thr Ile Asp Cys Gln Ser Ser Glu Ser Val Tyr Asn Asn
                20                  25                  30

Asn Asn Leu Ala Trp Tyr Gln Gln Lys Pro Gly Gln Pro Pro Lys Leu
            35                  40                  45

Leu Ile Tyr Gly Ala Ser Thr Leu Ala Ser Gly Val Ser Ser Arg Phe
50                  55                  60

Lys Gly Ser Gly Ser Gly Thr Glu Phe Thr Leu Thr Ile Ser Asp Leu
65                  70                  75                  80

Glu Cys Ala Asp Ala Ala Thr Tyr Tyr Cys Gln Gln Gly Tyr Ser Ile
                85                  90                  95

Gly Asn Val Asp Asn Ala Phe Gly Gly Gly Thr Glu Leu Glu Ile Leu
            100                 105                 110

<210> SEQ ID NO 59
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Ser Tyr Gly
                20                  25                  30

Val Ser Trp Val Arg Gln Ala Pro Gly Asn Gly Leu Glu Trp Ile Gly
            35                  40                  45

Ala Ile Ser Ser Gly Gly Asp Ala Tyr Tyr Ala Ser Trp Ala Thr Ser
50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Leu Val Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Lys Ala Ser Thr Leu Ala Ser Gly Val Pro Ser Arg Phe Lys Gly
50                  55                  60

```
Ser Gly Ser Gly Thr Gln Phe Thr Leu Thr Ile Ser Asp Val Val Cys
 65                  70                  75                  80

Asp Asp Ala Ala Thr Tyr Tyr Cys Ala Gly Tyr Lys Gly Gly Ser Ser
                 85                  90                  95

Asp Gly Ser Ala Phe Gly Gly Gly Thr Glu Leu Glu Ile Leu
            100                 105                 110

<210> SEQ ID NO 61
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ser Val Glu Glu Ser Gly Gly Gly Leu Phe Lys Pro Ala Asp Thr
  1               5                  10                  15

Leu Thr Leu Thr Cys Thr Val Ser Gly Phe Ser Leu Ser Tyr Pro Gly
                 20                  25                  30

Val Ser Trp Val Arg Gln Ala Pro Gly Asn Gly Leu Glu Tyr Ile Gly
             35                  40                  45

Phe Ile Asn Ala Asp Gly Asp Ser Tyr Tyr Pro Thr Trp Ala Lys Arg
 50                  55                  60

Arg Ser Thr Ile Thr Arg Asn Thr Asn Leu Asn Thr Val Thr Leu Lys
 65                  70                  75                  80

Met Thr Ser Leu Thr Ala Ala Asp Thr Ala Thr Tyr Phe Cys Ala
                 85                  90                  95

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Pro Val Leu Thr Gln Ser Pro Ser Ala Ser Ala Ala Leu Gly Ser
  1               5                  10                  15

Ser Ala Lys Leu Thr Cys Thr Leu Ser Ser Ala His Lys Thr Tyr Tyr
                 20                  25                  30

Ile Glu Trp Tyr Gln Gln Gln Gly Glu Ala Pro Arg Tyr Leu Met
             35                  40                  45

Gln Val Lys Ser Asp Gly Ser Tyr Thr Lys Gly Thr Gly Val Pro Asp
 50                  55                  60

Arg Phe Ser Gly Ser Ser Ser Gly Ala Asp Arg Tyr Leu Ile Ile Pro
 65                  70                  75                  80

Ser Val Gln Ala Asp Asp Glu Ala Asp Tyr Tyr Cys Gly Ala Asp Tyr
                 85                  90                  95

Ser Gly Gly Tyr Val Leu Gly Gly Gly Thr Gln Leu Thr Val Thr
            100                 105                 110

<210> SEQ ID NO 63
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 63

Gln Ser Leu Glu Glu Ser Gly Gly Leu Phe Lys Pro Ala Asp Thr
1               5                   10                  15

Leu Thr Leu Ala Cys Thr Val Ser Gly Phe Ser Leu Ser Thr Tyr Gly
            20                  25                  30

Val Ile Trp Val Arg Gln Ala Pro Gly Lys Gly Leu Glu Tyr Ile Ala
        35                  40                  45

Tyr Ile Asn Tyr Ser Gly Ser Pro Tyr Tyr Ala Ser Trp Ala Lys Ser
50                  55                  60

Arg Ser Thr Ile Thr Arg Asn Thr Asn Glu Lys Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 64
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Pro Val Leu Thr Gln Ser Pro Ser Ala Ser Ala Ala Leu Gly Ser
1               5                   10                  15

Ser Ala Lys Leu Thr Cys Thr Leu Ser Ser Ala His Lys Thr Tyr Tyr
            20                  25                  30

Ile Asp Trp Tyr Gln Gln Gln Gly Glu Ala Pro Arg Tyr Leu Met
        35                  40                  45

Gln Leu Gly Ser Asp Gly Ser Tyr Thr Lys Gly Thr Gly Val Pro Asp
50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ser Asp Tyr
                85                  90                  95

Ser Gly Gly Tyr Val Phe Gly Gly Gly Thr Gln Leu Thr Val Thr
            100                 105                 110

<210> SEQ ID NO 65
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ser Arg Trp Arg Ser Pro Gly Gly Leu Phe Lys Pro Thr Asp Thr
1               5                   10                  15

Leu Thr Leu Thr Cys Thr Val Ser Gly Phe Ser Leu Ser Gly Tyr Gly
            20                  25                  30

Val Ser Trp Val Arg Gln Ala Pro Gly Asn Gly Leu Glu Trp Ile Gly
        35                  40                  45

Ala Ile Ser Ser Gly Gly Ser Ala Tyr Tyr Ala Arg Trp Ala Lys Ser
50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg

<210> SEQ ID NO 66
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Pro Val Leu Thr Gln Ser Pro Ser Val Ser Ala Ala Leu Gly Ala
1               5                   10                  15

Ser Ala Lys Leu Thr Cys Thr Leu Ser Ser Ala His Lys Thr Tyr Thr
            20                  25                  30

Ile Asp Trp Tyr Gln Gln Gln Gly Glu Ala Pro Arg Tyr Leu Met
        35                  40                  45

Gln Leu Lys Ser Asp Gly Ser Tyr Thr Lys Gly Thr Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ser Gly Gly Tyr Val Phe Gly Gly Gly Thr Gln Leu Thr Val Thr
            100                 105                 110

<210> SEQ ID NO 67
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Asn Tyr Gly
            20                  25                  30

Val Ser Trp Val Arg Gln Ala Pro Gly Asn Gly Leu Glu Tyr Ile Gly
        35                  40                  45

Phe Ile Ser Asn Gly Gly Ala Thr Phe Tyr Ala Thr Trp Ala Arg Ser
    50                  55                  60

Arg Ala Thr Ile Thr Arg Asn Thr Gly Leu Asn Thr Val Ala Leu Thr
65                  70                  75                  80

Met Thr Ser Leu Thr Ala Ala Asp Thr Ala Thr Tyr Phe Cys Val Arg
                85                  90                  95

<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Gly Ser Ala
            20                  25                  30

```
Ile Ser Trp Tyr Gln Gln Lys Pro Gly Lys Pro Pro Thr Leu Leu Ile
            35                  40                  45

Tyr Gly Val Phe Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Ala Ser Asp Ser Ser
                85                  90                  95

Thr Gly Leu Thr Phe Gly Ala Gly Thr Asn Val Glu Ile Lys
            100                 105                 110

<210> SEQ ID NO 69
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Ser Val Lys Glu Ser Glu Gly Gly Leu Phe Lys Pro Thr Asp Thr
1               5                   10                  15

Gln Thr Leu Thr Cys Thr Val Ser Gly Phe Ser Leu Ser Ser Asn Ala
            20                  25                  30

Ile Ser Trp Val Arg Gln Ala Pro Gly Asn Gly Leu Lys Ser Ile Gly
            35                  40                  45

Phe Ile Asn Ser Gly Gly Gly Ala Tyr Tyr Ala Thr Trp Ala Lys Ser
    50                  55                  60

Arg Ser Thr Ile Thr Arg Asn Thr Asn Glu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Pro Val Leu Thr Gln Ser Pro Ser Leu Ser Ala Ser Leu Gly Thr
1               5                   10                  15

Thr Ala Arg Leu Thr Cys Thr Leu Ser Thr Gly Tyr Ser Val Gly Glu
            20                  25                  30

Tyr Pro Leu Val Trp Leu Gln Gln Val Pro Gly Arg Pro Pro Arg Tyr
            35                  40                  45

Leu Leu Ser Phe Thr Ser Asp Glu Asp Lys His His Asp Ser Trp Gly
    50                  55                  60

Pro Thr Arg Phe Ser Gly Ser Lys Asp Thr Ser Glu Asn Thr Phe Ile
65                  70                  75                  80

Leu Ser Ile Ser Gly Leu Gln Pro Glu Asp Glu Ala Asp Tyr Tyr Cys
                85                  90                  95

Ala Thr Ala His Gly Ser Asp Asn Ser Leu His Tyr Val Phe Gly Gly
            100                 105                 110

Arg Thr Gln Leu Thr Val Thr
            115
```

<210> SEQ ID NO 71
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Ser Leu Glu Glu Ser Gly Gly Gly Leu Phe Lys Pro Thr Asp Thr
1               5                   10                  15

Leu Thr Leu Thr Cys Thr Val Ser Gly Phe Ala Leu Asn Asn Tyr Asn
            20                  25                  30

Ile His Trp Val Arg Gln Ala Pro Gly Asn Gly Leu Glu Trp Ile Gly
        35                  40                  45

Ala Ile Gly Ser Ser Gly Ser Ala Tyr Tyr Ala Ser Trp Ala Lys Ser
    50                  55                  60

Arg Ser Thr Ile Thr Arg Asn Thr Asn Leu Asn Thr Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 72
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Pro Val Leu Thr Gln Ser Pro Ser Ala Ser Ala Ala Leu Gly Ser
1               5                   10                  15

Ser Ala Lys Leu Thr Cys Thr Leu Ser Ser Ala His Lys Thr Tyr Tyr
            20                  25                  30

Ile Glu Trp Tyr Gln Gln Gln Gly Glu Ala Pro Arg Tyr Leu Ile
        35                  40                  45

Gln Leu Lys Ser Asp Gly Ser Tyr Thr Lys Gly Thr Gly Val Pro Asp
    50                  55                  60

Arg Phe Ser Gly Ser Ser Ser Gly Thr Asp Arg Tyr Leu Ile Ile Ser
65                  70                  75                  80

Ser Val Gln Ala Glu Asp Glu Ala Asp Tyr Ser Cys Gly Ala Asp Tyr
                85                  90                  95

Ser Gly Gly Phe Val Phe Gly Gly Gly Thr Gln Leu Thr Val Thr
            100                 105                 110

<210> SEQ ID NO 73
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Val Gly Gly Gly Val Gln Gly Gly Gly Leu Val Lys Pro Gly Asp Thr
1               5                   10                  15

Leu Thr Leu Thr Cys Thr Val Ser Gly Phe Pro Leu Ser Ser Tyr Asp
            20                  25                  30

Met Asn Trp Val Arg Gln Ala Pro Gly Glu Gly Leu Glu Trp Ile Gly
            35                  40                  45

Trp Ile Thr Tyr Asp Gly Tyr Asn His Tyr Ala Ser Trp Ala Asn Gly
 50                  55                  60

Arg Ser Thr Ile Thr Arg Asn Thr Asn Glu Asn Ala Val Thr Leu Lys
65                  70                  75                  80

Met Thr Ser Leu Thr Ala Ala Asp Thr Ala Thr Tyr Phe Cys Ala Arg
                85                  90                  95

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Leu Val Leu Thr Gln Thr Pro Pro Ser Leu Ser Ala Ser Val Gly
1               5                   10                  15

Gly Thr Val Thr Ile Asn Cys Leu Ala Ser Glu Asn Val Tyr Ser Ala
            20                  25                  30

Val Ala Trp Tyr Gln Gln Lys Pro Gly Lys Pro Thr Leu Leu Ile
         35                  40                  45

Ser Gly Thr Ser Asn Leu Glu Ala Gly Val Pro Pro Arg Phe Ser Gly
     50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys
            100                 105

<210> SEQ ID NO 75
<211> LENGTH: 804
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
cccagccggc catggctgag ctcgtgatga cccagactga atcgcccgtg tctgcagctg     60
tgggaagcac agtcaccatc aattgccagg ccagtcagag tgtttatagt aacaacaact    120
tagcctggtt tcagaagaaa ccagggcagc ctcccaagcg cctgatccat tctgcatcca    180
ctctggcatc tggggtccca tcgcggttca aaggcagtgg atctgggaca cagttcactc    240
tcaccatcag cgacctggag tgtgacgatg ctgccactta ctactgtcag gcgttttta    300 gtggtagtat tagtgttttc ggcggaggga ccgaggtggt cgtcaaggtg gttcctctag    360
atcttcctcc tctggtggcg gtggctcggg cggtggtggg cagtcgctgg aggagtccgg    420
gggaggtctc ttcaagccaa cggataccct gacactcacc tgcacagtct ctggattctc    480
cctcagtaac tatggagtgg tctgggtccg ccaggctcca gggaacgggc tggaatggat    540
cggaatcatt gatcatcatg gtatcccata ctacgcaacc tgggcgaaaa gccgatccac    600
catcaccaga acaccaacct ggacacggt gactctgaaa atgaccagtc tgacagccgc    660
ggacacggcc acctatttct gtgcgagagc ttacgttaat tttggctggg attatgctct    720

```
taacatctgg ggtccaggca ccctggtcac cgtctcctca gggcaaccta aggctccgtc    780
agtcactagt ggcccgggag gcca                                           804
```

<210> SEQ ID NO 76
<211> LENGTH: 803
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
ccggccatgg ctcagcctgt gctgactcag tcgccctctg tgtctgctgc cctgggatcc    60
tcggccaagc tcacctgcac tctgagcagt gctcacaaga cctactatat tgaatggtat   120
cagcaacaac aaggggaggc ccctcggtac ctgatgcaac ttgagagtga tggaagctac   180
accaagggga ccgggtccc tgatcgcttc tcggctcca gctctggggc tgaccgctac     240
ttgatcatct ccagcgtcca ggctgaggac gaagccgact actattgtgg tgcagattat   300
agtggtgggt ttgtgttcgg cggagggacc cagctgaccg tcacaggtgg tggttcctct   360
agatcttcct cctctggtgg cggtggctcg gcggtggtg gcagtcggt gaaggagtcc     420 ggggaggtct cctcaagcca acggataccc tgacactcac ctgcacagtc tctggattct   480
ccctcaatag ctatgcagta ttctgggtcc gccaggctcc agggaacggg ctggaatgga   540
tcggaaccgt tagtagtgtt ggtgacacat acttcgcgac ctgggcgaaa agccgatcca   600
ccatcaccag aaacaccaac ctgaacacg tgactctgaa atgaccagt ctgacagccg     660 cggacacggc cacctatttt tgtgcgaggg gggttggtgt tagttattat cttgatgctt   720
ttgattcttg gggcccaggc accctggtca ccgtctcctc agggcaacca ggctccatca   780
gtcactagtg gcccgggagg cca                                           803
```

<210> SEQ ID NO 77
<211> LENGTH: 809
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
ccggccatgg ctgagctcgt gatgacccag actgaacccc cgtgtctgc acctgtggga    60 ggcacagtca ccatcaattg ccaggccagt cagaacattg gtagtagcta cttatcctgg   120
tatcagcaga aaccagggca gcctcccaag ctcctgatct accaggcttc cactctggca   180
tctggggtcc catcgcggtt caaaggcggt ggatctggga cagactcag tctcaccatc     240 agcggcgtgc agtgtgccga tgccgccact tattactgtc aaagtacttt ttatagtagt   300
ggtactggtt atgctttcgg cggagggacc gagctggaga tcctggtggt tcctctagat   360
cttcctcctc tggtggcggt ggctcggcg gtggtgggca gtcggtggag gagtccgggg    420
gaggtctctt caagccaacg gataccctga cactcacctg cacagtctct ggattctccc   480
tcagtggcta tgagtgagc tgggtccgcc aggctgcagg gaacgggctg gaatggatcg   540
gagccattag tagtggtggt agcgcatact acgcgagatg ggcgaaaagc cgatccacca   600
tcaccagaaa caccaacctg aacacggtga ctctgaaaat gaccagtctg acagccgcgg   660
acacggccac ctatttctgt gcgagaggtt actatactgc tattggtggt acttatgaca   720 atgctttga tccctgggc ccaggcaccc tggtcaccgt ctcctcaggg caacctaagg     780
```

```
ccatcagtca ctagtggccc gggaggcca                                       809
```

<210> SEQ ID NO 78
<211> LENGTH: 806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (750)..(750)
<223> OTHER INFORMATION: a, c, t, g, unknown or other
<220> FEATURE:
<221> NAME/KEY: modified_base
<222> LOCATION: (763)..(763)
<223> OTHER INFORMATION: a, c, t, g, unknown or other
<220> FEATURE:
<221> NAME/KEY: modified_base
<222> LOCATION: (766)..(766)
<223> OTHER INFORMATION: a, c, t, g, unknown or other
<220> FEATURE:
<221> NAME/KEY: modified_base
<222> LOCATION: (772)..(772)
<223> OTHER INFORMATION: a, c, t, g, unknown or other
<220> FEATURE:
<221> NAME/KEY: modified_base
<222> LOCATION: (774)..(775)
<223> OTHER INFORMATION: a, c, t, g, unknown or other

<400> SEQUENCE: 78

```
gcccagccg gccatggctc agcctgtgct gactcagtcg ccctctgtgt ctgccgccct       60
gggagcctct gccaagctca cctgcaccct gagcagtggc cacaagacct acaccattga    120
ctggtatcag cagcagcagc aaggggaggc ccctcggtac ctgatgcaga ttgggagtga    180
tggaagctac accaagggga ccggggtccc tgatcgcttc tcgggctcca gctctgggac    240
tgaccgctac ttgatcatct ccagcgtcca ggctgaggac gaagccgact actattgtgg    300
tgcagattat agtggtgggt ttgtgttcgg cggagggacc cagctgaccg tcacaggtgg    360
tggttcctct agatcttcct cctctggtgg cggtggctcg ggcggtggtg ggcagtcggt    420
gaaggagtcc gagggaggtc tcttcaagcc aacggatacc ctgacactca cctgcacagc    480
ctccgaattc accatcggta gttatagtag tggctgggtc cgccaggctc agggaaagga    540
gctggagtgg atcggaaccc ttagttctac tggtagcgca cactacgcga actgggcgaa    600
aggccgttcc accatcacca gaaacaccaa cgagaacacg gtgactctga agatggccag    660
tctgacagcc gcggacacgg ccacctattt ctgtgcgaga gctgattatg ggccctgtta    720
ttttgacatc tggggcccag gcaccctggn caccgttttc tcnggnaacc tnannctcca    780
tcagtcacta gtggcccggg aggcca                                         806
```

<210> SEQ ID NO 79
<211> LENGTH: 794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
ccggccatgg ctgagctcgt gatgacccag actccatcct ctgtgtctgc agctgtggga     60
ggcacagtca ccatcaattg ccaggccagt cagactatta caacctctt agcctggtat    120
cagcagaaac cagggcagcc tcccaagctc ctgatttatg gtgcatccac tctggcatct    180
```

-continued

```
ggggtcccat cgcgtttcag cggcagtgga tctgggacac agttcattct caccatcagt     240
ggcatgaagg ctgaagatgc tgccacttat tactgtcaaa gtgcttatta taatgctggt     300 gcgactttg  gagctggcac caatgtggaa atcaaggtgg ttcctctaga tcttcctcct     360
ctggtggcgg tggctcgggc ggtggtgggc agtcggtgga ggagtccggg ggaggtctct     420
tcaagccaac ggatacccctg acactcacct gcacagtctc tggaatcgac ctcagtagaa    480
atggagtgac ctgggtccgc caggctccag ggagcgggct ggaatggatc ggagtcatta    540
atagtcatgg tgacagtgat tacgcgacct gggcgaacag ccgatccacc atcaccagaa    600
acaccaacct gaacacggtg actctgaaaa tgaccagtct gacagccgcg gacacggcca    660
cctatttctg tgcgagtact tatgatagtt attatgatta tgcttggcct aattttggca    720
tctggggccc aggcaccctg gtcaccgtct cctcagggca acctaaggcc agtcactagt    780
ggcccgggag gcca                                                        794
```

<210> SEQ ID NO 80
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
ggcccagccg gccatggctc agcctgtgct gactcagtcg ccctctgtgt ctgccgccct      60
gggagcctct gccaagttca cctgcaccct gagcagtggc cacaagacct acaccattga    120
ctggtatcag cagcagcagc aaggggaggc ccctcggtac ctgatgcaga ttgggagtga    180
tggaagctac accaagggga ccggggtccc tgatcgcttc tcgggctcca gctctgggac    240
tgaccgctac ttgatcatct ccagcgtcca ggctgaggac gaagctgact acatctgtgg    300
tgtaactggt agtaatgttt atgcacagga cccagctgac cgtcacaggt ggtggttcct    360
ctagatcttc ccctggtggc ggtggccggg cggtggtggg cagtcgctgg aggagtccgg    420
gggaggtctc ttcaagccaa cggatacccct gacactcacc tgcacagtct ctggattctc    480
cctcagtaac agtgcaatga ctgggtccg ccaggctcca gggaacgggc tggaatggat     540
cggagacatt gatagtagtg gtagcgcata ctacgcgagc tgggcgaaaa gccgatccac    600
catcaccaga aacaccaacc tgaacacggt gactctgaaa atgaccagtc tgacagccgc    660
ggacacggcc acctatttct gtgcgagagg gggttatggt aatgctggta ctccttacta    720
tggcatggac ctctggggcc cagggaccct cgtcaccgtc tcctcagggc aacctaaggc    780
tccatcagtc actagtggcc cgggaggcca                                      810
```

<210> SEQ ID NO 81
<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (705)..(705)
<223> OTHER INFORMATION: a, c, t, g, unknown or other

<400> SEQUENCE: 81

```
ccggccatgg ctgagctcgt gatgacccag actccatcct ctgtgtctgc agctgtggga     60
ggcacagtca ccatcaattg ccaggccagt gaaagcatta gcaactactt agcctggtat    120
```

| cagcagaaac cagggcagcc tcccaagctc ctgacctatg atgcatctga tctggcatct | 180 |
| gggtcccat cgcggttcag cggcagtgga tatgggacag agttcactct caccattagt | 240 |
| ggcgtgaagg ctgaagatgc tgccacttat tattgtcaaa gtggttatgt tagtgctggg | 300 |
| acttttggag ctggcaccaa tgtggaaatc aaggtggttc ctctagatct tcctcctctg | 360 |
| gtgggcggt ggtgggcagt cgttggagga gtccggggga ggtctcttca agccaacgga | 420 |
| taccctgaca ctcacctgca cagtctctgg attcgacatt agtggcgttt acatgagctg | 480 |
| ggtccgccag ctccaggga acgggctgga gtggatcgga gccattgatc gtggtggtgg | 540 |
| cacttactac gcgagctggg cgataggccg atccaccatc accagaaaca ccaacgacaa | 600 |
| cacggtgact ctggaaatga ccagtctgac agccgcggac acggccacct atttctgtgc | 660 |
| gaaaggatat agtgttcttg atccctgggg cccaggcacc ctggncaccg tctcctcagg | 720 |
| gcaacctaag gctccatcag tcactagtgg cccgggaggc ca | 762 |

<210> SEQ ID NO 82
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

| ggcccagccg gccatggctc agcctgtgct gactcagtcg ccctctgtgt ctgccgccct | 60 |
| gggagcctct gccaagctca cctgcaccct gagcagtgcc cacaagacct acaccattga | 120 |
| ctggtatcag cagcagcaag gggaggcccc tcgatacctg atgcatctta agagtgatgg | 180 |
| aacctacacc aaggggaccg ggtccctga tcgcttctcg ggctccagct ctggggctga | 240 |
| ccgctacttg atcatcccca gcgtccgaac tgatgacgaa gccgactact attgtggtac | 300 |
| agattacagc ggtgggtatg tattcggcg agggacccag ctgaccgtca caggtggtgg | 360 |
| ttcctctaga tcttcctcct ctggtggcgg tggctcgggc ggtggtgggc agtcgctgga | 420 |
| ggagtccggg ggaggcctga tcaagccaac ggatatgttg acactcacct gcacagtctc | 480 |
| tggattctcc ctcagtaact atggagtgat gtgggtccgc caggctccag ggaacggact | 540 |
| ggagtcgatc ggatatattg gtagtggtgg tgacacatcc tacgcgagct gggcgaaaag | 600 |
| ccgatccacc atcgccagaa acaccaacga gaacacggtg tctctgctca tgaatggtct | 660 |
| gacagccgcg gacacggcca cctatttctg tgcgagagat cctggttata gtgctggtag | 720 |
| tgcttttgat ccctggggcc caggcaccct ggtcaccgtc ttctcagggc aacctaaggc | 780 |
| tccatcagtc actagtggcc cgggaggcca | 810 |

<210> SEQ ID NO 83
<211> LENGTH: 820
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

| ggcccagccg gccatggctc agcctgtgct gactcagtcg ccctctgcat ctgctgccct | 60 |
| gggatcctcg gccaagctca cctgcactct gagcagtgct cacaagacct actatattga | 120 |
| ctggtatcag cagcagcaag gggaggcccc tcggtacctg atgcaggtta agagtgatgg | 180 |

```
aagctacacc aggggaccg gggtccctga tcgcttctcg ggctccagct ctggggctga    240
ccgctacttg atcatcccca gcgtccaggc tgatgacgaa gccgactact attgtggttc    300
agattatagc ggtgggtatg tgttcggcgg agggacccag ctgaccgtca caggtggtgg    360
ttcctctaga tcttcctcct ctggtggcgg tggctcgggc ggtggtgggc agtcgttgga    420
ggagtccggg ggaggtctct tcaagccaac ggataccctg acactcacct gcacagtctc    480
tggattctcc ctcagtatct atggagtgag ctgggtccgc caggctccgg ggaatgggct    540
ggaatgggtc ggagccattg gtagtggtgg tagcgcatac tacgcgacct gggcgaaaag    600
ccgatccacc atcaccagaa acaccaacct gaacacggtg actctgaaaa tggccagtct    660
gacagccgcg gacacggcca cctatttctg tgcgagaggt tactatactg ctattggtgg    720
tacttatgac aatgcttttg atccctgggg cccaggcacc ctggtcaccg tctcctcagg    780
gcaacctaag tccatcagtc actagtggcc cgggaggcca                         820

<210> SEQ ID NO 84
<211> LENGTH: 799
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (754)..(754)
<223> OTHER INFORMATION: a, c, t, g, unknown or other
<220> FEATURE:
<221> NAME/KEY: modified_base
<222> LOCATION: (763)..(763)
<223> OTHER INFORMATION: a, c, t, g, unknown or other
<220> FEATURE:
<221> NAME/KEY: modified_base
<222> LOCATION: (767)..(767)
<223> OTHER INFORMATION: a, c, t, g, unknown or other
<220> FEATURE:
<221> NAME/KEY: modified_base
<222> LOCATION: (788)..(788)
<223> OTHER INFORMATION: a, c, t, g, unknown or other

<400> SEQUENCE: 84
ccggccatgg ctgagctcga tctgacccag actccatcct ctgtgtctgc agctgtggga     60
ggcacagtca ccatcaattg ccaggccagt cagagtgtta gcaacctctt agcctggtat    120
cagcagaaac cagggcagcc tcccaagctc ctgatttatg gtgcatccaa tctggaatct    180
ggggtcccat cgcgtttccg tggcagtgga tctgggacag agttcactct caccatcagc    240
gatgtggtgt gtgacgatgc tgccacttac tactgtgcag acataaaaag tagtagtact    300
gatggtactg ctttcggcgg agggaccgag ctggagatcc tggtggttcc tctagatctt    360
cctcctctgg tggcggtggc tcgggcggtg gtggcagtc ggtggaggag tccaggggag    420
gtctcttcaa gccaacggat accctgacac tcacctgtac agtctctgga ttctccctta    480
gtacctacaa catacaatgg gtccgccagg ctccagggaa cgggctggaa tatatcggaa    540
ccattggtag tagtggtagc gcatactacg cgagccgggc gaaaagccga tccaccatca    600
ccagaaacac cgccctgaac acggtgtctc tgcaagtgga cagtctgaca gacgcggaca    660
cggccaccta tttctgtgcg agaggaggga cttggtatac agatggtctt gcttatgttg    720
atgcttttga tctctggggc ccaggcaccc tggncaccgc ctnctcnggc aacctagtca    780
ctagtggncc gggaggcca                                                 799

<210> SEQ ID NO 85
```

<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
ggcccagccg gccatggctc agcctgtgct gactcagtcg ccctctgcat ctgctgccct      60
gggatcctcg gccaagctca cctgcactct gagcagtgct cacaagacct actatattga     120
ctggtatcag cagcagcaag gggaggcccc tcggtatctg atgcaggtta agagtgatgg     180
aagctacacc aaggggaccg gggtccctga tcgcttctcg ggctccagct ctggggctga     240
ccgctacttg atcatcccca gcgtccaggc tgatgacgaa gccgactact attgtggttc     300
agattatagc ggtgggtatg tgttcggcgg aggggcccag ctgaccgtca caggtggtgg     360
ttcctctaga tcttcctcct ctggtggcgg tggctcgggc ggtggtgggc agtcggtgaa     420
ggagtccgag gaggtctctc tcaagccaac ggatacccctg acactcacct gcacagtctc    480
tggattcacc gtcagtaaca atgcaataag ctgggtccgc caggctccag ggaatgggct     540
ggaatggatc ggagccatta gttacggtgg taacacatac tacgcgaact ggccgaaaag     600
ccgatccacc atcaccagaa acaccaacct gaacacggtg actctgaaaa tgaccagtct     660
gacagccgcg gacacggcca cctatttctg tgcgagattc tactatggtg ctggttatgc     720
ctatgacatc tggggcccag gcaccctggt caccgtcttc tcagggcaac ctaaggctcc     780
gtcagtcact agtggcccgg gaggcca                                         807
```

<210> SEQ ID NO 86
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (729)..(729)
<223> OTHER INFORMATION: a, c, t, g, unknown or other
<220> FEATURE:
<221> NAME/KEY: modified_base
<222> LOCATION: (755)..(755)
<223> OTHER INFORMATION: a, c, t, g, unknown or other
<220> FEATURE:
<221> NAME/KEY: modified_base
<222> LOCATION: (762)..(763)
<223> OTHER INFORMATION: a, c, t, g, unknown or other

<400> SEQUENCE: 86

```
ccggccatgg ctgagctcga tatgacccag actccatcct ctgtgtctgc agctgtggga      60
gacacagtca ccatcaattg tcaggccagt cagagtgtta ccaacctctt agcctggtat     120
cagcagaaac caaggcagcc tcccaaactc ctgatttatg atgcatccaa tctagaatct     180
ggagtcccat cgcgtttccg tggcagtgga tctgggacag agttcactct caccatcagt     240
ggcatgaagg ctgaagatgc tgccacttat tactgtcaaa gtggttatta gtgctggt      300
gcgacttttg gagctggcac caatgtggaa atcaaggtgg ttcctctaga tcttcctcct     360
ctggtggcgg tggctcgggc ggtggtgggc agtcggtgaa ggagtccgag gaggtctct     420
tcaagccaac ggatacccctg acactcacct gcacagtctc tggattctcc ctcagtaact    480
atggagtgag ctgggtccgc caggctccag ggaaggaggt ggagtggatc ggatacatta    540
acagtggtgg tagtactaat tacgcgagct gggcgaaaag ccgatccacc atcaccagaa    600
```

```
acaccaattt gaacacggtg actctgaaaa tgaccagcct gacagccgcg gacacggcca    660
cctatttctg tgcgagaggt taccgtggtt ataatgttgg tatggatgct tttgatgtct    720
ggggcccang caatctggtc accgtctcct caggnaacct annctctcag tcactagtgg    780
cccgggaggc ca                                                        792
```

<210> SEQ ID NO 87
<211> LENGTH: 804
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
ccggccatgg ctgagctcgt gctgacccag actccatccc cagtgtctgc ggctgttgga     60
ggcacagtca ccatcaattg ccagtccagt cagagtgttt atagtaacaa ccgcttagcc    120
tggtatcagc agaaaccagg gcagcctccc aagcaactga tctattatgc atccactctg    180
gcatctgggg tctcatcgcg gttcaaaggc agtggatctg gacacagtt cactctcacc     240 atcagcgatg tggtgtgtga cgatgctgcc acttactact gtgcaggata taaaaatagt    300
ggtattgatg aacatgcttt cggcggaggg accgagctgg agatcctggt ggttcctcta    360
gacttctcct ctggtggcgg tggctcgggc ggtggtgggc agtcggtgaa ggagtccgag    420
ggaggtctct tcaagccaat ggatagcatg acactcacct gcacagtctc tggattctcc    480
ctcagtagct atgagtgag ctgggtccgc caggctccag gaacgggct ggaatggatc       540 ggagccatta gtagtggtgg tagcgcatac tacgcgagat gggcgaaaag ccgagccacc    600
atcaccagaa acaccaacct gaacacggtg actctgaaaa tggccagtct gacagccgcg    660
gacacggcca cctatttctg tgcgagaggt tactatactg ctattggtgg tacttatgac    720
aatgcttttg atccctgggg cccaggcacc ctggtcaccg tctcctcagg gcaacctaac    780
agtcactagt ggcccgggag gcca                                           804
```

<210> SEQ ID NO 88
<211> LENGTH: 812
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
ggcccagccg gccatggctc agcctgtgct gactcagtcg ccctctgtgt ctgccgccct     60
gggagcctct gccaagctca cctgcaccct gagcagtggc cacaagacct acaccattga    120
ctggtatcag cagcagcaag ggaggcccc tcggtacctg atgcagcttg ggagtgatgg     180
aagctacacc aagcagaccg gggtccctga tcgcttctcg ggctccagct ctggggctga    240
ccgctacttg atcatctcca gcgtccaggc tgatgacgaa gccgactact attgtggtgc    300
ggattatagt ggtgggtttg tgttcggcgg agggacccag ctgaccgtca caggtggtgg    360
cctctagatc ttcctcctct ggtggcgtg gctcggcgg tggtgggcag tcgttggagg      420
agtccggggg aggtctcttc aagccaacgg ataccctgac actcacctgc acagtctctg    480
gattctccct caacaggtac gacatgagtt gggtccgcca ggctccaggg aacgggctgg    540
aatggatcgg agtcattaat agtggtgggt tcacatacta cgcgagctgg gcgaaaagcc    600
```

| | |
|---|---|
| gatccaccat caccagaaac accaacgaga acacggtgac tctgaaaatg accagtctga | 660 |
| cagccgcgga cacggccacc tatttctgtg cgagaggtta ccgtggttat aatgttggta | 720 |
| tggatgcttt tgatgtctgg ggcccaggca atctggtcac cgtctcctca gggcaaccta | 780 |
| agtccgtcag tcactagtgg cccgggaggc ca | 812 |

<210> SEQ ID NO 89
<211> LENGTH: 818
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

| | |
|---|---|
| ggcccagccg ccatggctg agctcgtgct gacccagact ccatcgtccg tgtctgcagc | 60 |
| tgtgggaggc acagtcagca tcagttgcca gtccagtcag agtgtttata gtaactactt | 120 |
| agcctggtat cagcagaaac cagggcagcc tcccaagctc ctgatctatt atgcatccac | 180 |
| tctggcatct ggggtctcat cgcggttcaa aggcagtgga tctgggacac agttcactct | 240 |
| caccatcaac ggcgtgcagt gtgacgatgc tgccacttac tactgtcaag cacttttga | 300 |
| tgatggtttg tacaaggctt tcggcggagg gaccgagctg gagatcctgg tggttcctct | 360 |
| agatcttcct cctctggtgg cggtggctcg ggcggtgtgg gcagtcggtg aaggagtccg | 420 |
| agggaggtct cttcaagcca acggataccc tgacactcac ctgcacagtc tctggattct | 480 |
| ccctcagtaa caatgcaata aactgggtcc gccaggctcc agggaacggg ctggagtgga | 540 |
| tcggagccgt tggtagtggt ggtagggcat actacgcggg ctgggcgaaa agccgatcca | 600 |
| ccatcaccag aaacaccaac ctgaacacgg tgactctgaa aatgacgaat ctgcagccg | 660 |
| cggacacggc cacctatttc tgtgcgagag tcggatttta ctatggcaat ggtctttctt | 720 |
| atggtattgg cgcttttgat ccctggggcc caggcaccct ggtcaccgtc tcctcagggc | 780 |
| aaccaggctc cgtcagtcac tagtggcccg ggaggcca | 818 |

<210> SEQ ID NO 90
<211> LENGTH: 794
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

| | |
|---|---|
| ccggccatgg ctgagctcgt gatgacccag actccatcct ctgtgtctgc agctgtggga | 60 |
| ggcacagtca ccatcaattg ccaggccagt cagagtgttt acaacctctt agcctggtat | 120 |
| cagcagaaac cagggcagcc tcccaagctc ctgactcatg gtacatccaa tctggaatct | 180 |
| ggggtcccat cgcgtttccg tggcagtgga tctgggacag agttcactct caccatcagt | 240 |
| ggcatgaagg ctgaagatgc tgccacttat tactgtcaaa gtggttatta tagtactggt | 300 |
| gcgactttg gagctggcac caatgtggaa atcaaggtgg ttcctctaga tcttcctcct | 360 |
| ccggtggcgg tggctcgggc ggtggtggc agtcgctgga ggagtccggg ggaggtctct | 420 |
| tcaagccaac ggataccctg acactcacct gcacagtctc tggattctcc ctcagtaact | 480 |
| atggaatggg ctgggtccgc caggctccag ggaacgggct ggaatacatc ggattcatta | 540 |
| gtagtggtgg taatacatac tacgcgagct gggcgaaaag ccgatccacc atcaccagag | 600 |
| acaccaacct gaacacggtg actctgaaaa tgagcagtct gacagccgcg gacacggcca | 660 |

```
cctatttctg tgcgagaggt taccgtggtt ataatgttgg tatggatgct tttgatgtct    720 gggggcccagg caatctggtc accgtctcct cagggcaaca aggctccatc agtcactagt    780
ggcccgggag gcca                                                        794

<210> SEQ ID NO 91
<211> LENGTH: 784
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (686)..(686)
<223> OTHER INFORMATION: a, c, t, g, unknown or other

<400> SEQUENCE: 91
ccggccatgg ctgagctcga tctgacccag actccatcct ccgtgtctgc agctgtggga     60
ggcacagtca ccatcaattg ccagtccagt cagagtgttg atagtaacaa ttacttatcc    120
tggtatcagc agaaaccagg gcagcctccc aagctcctga tctatgatgc atccactctg    180
gcatctgggg tcccatcgcg gttcagcggc agtggatctg ggacacagtt cactctcacc    240
atcagcgaag tacagtgtga cgatgctgcc acttactact gtcaaggcag ttattatagt    300
ggtgattggt atgggcttt cggcggaggg accgagctgg agatcctggt ggttcctcta    360
gatcttcctc ctctggtggc ggtggctcgg gcggtggtgg gcagtcgttg gaggagtccg    420 gggaggtct cttcaagcca acggatcccc tgacactcac ctgcacagtc tctggattct    480
ccatcaatga ctacaacatg caatgggtcc gccaggctcc agggatcggg ctggaatgga    540
tcggagccat taatgcttgg ggtgatacat actatacgag ctgggcgaaa agccgatcca    600
ccatcaccag agacaccaac ctgaacacgg tgactctgaa aatgaccagt ctgacagccg    660
cggacacggc cacctatttc tgtgcnagag gttacagtct tgacatctgg ggcccaggca    720
ccctggtcac cgtctcctca gggcaaccta aggctccgtc agtcactagt ggcccgggag    780
gcca                                                                 784

<210> SEQ ID NO 92
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
cccagccggc catggctgag ctcgtgatga cccagactcc agcctccgtg tctgaacctg     60
tgggaggcac agtcaccatc agttgccagg ccagtcaggg tgtttatagc gaccgcctag    120
cctggtatca acagaaacca gggcagcctc ccaagctcct gatgtattat gcatccgatc    180
tgtcatctgg ggtcccatcg cggttcaaag gcagtggatc tgggacagag ttcactctca    240
ccatcagcga cctggagtgt gccgatgctg ccacttacta ctgtcaaagc aattatggta    300
gtcttagtag tagttatact ttcggcggag ggaccgaggt ggtcgtcaag gtggttcctc    360
tagatcttcc tcctctggtg gcggtggctc gggcggtggt gggcagtcgt tggaggagtc    420 cggggggaggt ctcttcaagc caacggatac cctgacactc acctgcacag cctccggatt    480
caccgtcact agcaacgcaa taagctgggt ccgccaggct ccagggaacg ggctggaata    540
```

| | |
|---|---:|
| tatcggattc attggtgctg ctggtaatgc aaactacgcg agctgggcga aaagccgctc | 600 |
| caccatcacc agaaacacca acctgaacac ggtgactctg aaaatgacca gtctgacagc | 660 |
| cgcggacacg gccacctatt tctgtgcgag agagggtggt tggggtacat tgtttggtgc | 720 |
| ttttgattcc tggggcccag gcaccctggt caccgtctcc tcagggcaac ctaaggctcc | 780 |
| atcagtcact agtggcccgg gaggcca | 807 |

<210> SEQ ID NO 93
<211> LENGTH: 797
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 93

| | |
|---|---:|
| ggcccagccg gccatggctg agctcgtgat gacccagact ccaccctccc tgtctgcatc | 60 |
| tgtgggagaa actgtcagga ttaggtgcct ggcgagtgag aacgtttaca gtgctgtagc | 120 |
| ctggtatcaa cagaagccag ggaaacctcc tacactcctg atctctggtg catccaattt | 180 |
| agaatctggg gtcccaccac ggttcagtgg cagtggatct gggacagatt acaccctcac | 240 |
| catcggcggc gtgcaggctg aagatgctgc cacttacttc tgtcaagggt atagcagtta | 300 |
| cctgactttt ggagctggca ccaatgtgga aatcaaggtg gttcctctag atcttcctcc | 360 |
| tctggtggcg gtggctcggg cggtggtggg cagtcggtgg aggagtccag gggaggtctc | 420 |
| ttcaagccaa cggataccct gacactcacc tgcacagtct ctggatttac catcgataccc | 480 |
| tatggagtga cctgggtccg ccaggctcca gggaacgggc tggaatatat cggattcatt | 540 |
| agtagtggtg gtgccgcata ctacgcgagc tgggcgaaaa gccgatccac catcaccaga | 600 |
| aacaccaatc tgaacacggt gactctgaaa atgaccagtc tgacagccgc ggacacggcc | 660 |
| acctatttct gtgcgagaga tcgtggctat gtttatggtt atggtgatgg tactgacatc | 720 |
| tggggcccag gcaccctggt caccgtctcc tcagggcaac ctaaggctcc atcagtcact | 780 |
| agtggcccgg gaggcca | 797 |

<210> SEQ ID NO 94
<211> LENGTH: 794
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 94

| | |
|---|---:|
| cccagccggc catggctcag cctgtgctga ctcagtcgcc ctctgcgtct gctgccctga | 60 |
| gatcctcggc caagctcacc tgcaccctga gcagtgccca aagagttac gacattgact | 120 |
| ggtatcagca gcagtcaggg gaggcccctc ggtacctaat gcgtcttagg agtgatggaa | 180 |
| agtacaccaa ggggaccggg gtccctgatc gcttctcggg ctccagctct ggggctgacc | 240 |
| gctacttgat catccccagc gtccaggctg atgacggagc cgactattat tgtggtacag | 300 |
| attatagcgg tggatatgtg ttcggcgag ggacccagct gaccgtcaca ggtggtggtt | 360 |
| cctctagatc ttcctcctgg tggcggtggc tcgggcggtg gtgggcagtc gctggaggag | 420 |
| tccggggag gcctgatcaa gccaacggat accctgacac tcacctgcac agtctctgga | 480 |
| ttctcccctca gtatctacga cataagctgg gtccgccagg ctccagggaa cgggctggaa | 540 |
| tggatcggag ccattggtag tggtgatacc acatactacg cgagctgggc gaaaagccga | 600 |

```
tccaccatca ccagaaacac ctacctgaac acggtgactc tgaaaatgac cagtctgaca    660
gccgcggaca cggccaccta tttctgtgcg agagggggt tatcctggtt caacatctgg    720
ggcccaggca ccctggtcac cgtctcctca gggcaaccta aggctccgtc agtcactagt    780
ggcccgggag gcca                                                     794
```

<210> SEQ ID NO 95
<211> LENGTH: 793
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
ccggccatgg ctgagctcgt gatgacccag actgaatccc ccgtgtctgc agctgtggga     60
ggcacagtca ccatcaattg ccaggccagt cagagcatta gcagttggtt ggcctggtat    120
caacagaagc cagggaaacc tcctacactc ctgatctctg gtgcatccaa tttagaatct    180
ggggtcccac cacggttcag tggcagtgga tctgggacag attcaccct caccattggc    240 ggcgtgcagg ctgaagatgc tgccacctac tattgtctag cggttatag ttacagtagt    300 atcggtacga cttttggagc tggcaccaat gtggaaatca aggtggttcc tctagatctt    360
cctcctctgg tggcggtggc tcgggcggtg gtgggcagga gcagctggtg gagtccgagg    420
gaggtctctt caagccaacg gataccctga cactcacctg cacagtgtct ggattctccc    480
tcaataacta tggagtgacc tgggtccgcc aggctccagg gaggggctg gaatggatcg    540 gagccgtttg gagtggtgct accacagact atgcgagctg ggcgaaaagc cgatccacca    600
tcaccagaaa caccaacgag aacacggtga ctctgaaaat gtccagtctg acagccgcgg    660
acacggccac ctatttctgt gcgaattttc ctggttatac ttctggtacc gacatctggg    720
gccctggcac cctggtcacc gtctcctcag ggcaacctaa ggctccgtca gtcactagtg    780
gcccgggagg cca                                                      793
```

<210> SEQ ID NO 96
<211> LENGTH: 799
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
ccggccatgg ctgagctcgt gatgacccag actccatcct ctgtgtctgc agctgtggga     60
ggcacagtca ccatcaattg tcaggccagt cagagtgtta acaacctctt agcctggtat    120
cagcagaaac cagggcagcc tcccaagctc ctgacttatg gtacatccaa tctggaatct    180
ggggtcccat cgcgtttccg tggcagtgga tctgggacag agttcactct caccatcagt    240
ggcatgaagg ctgaagatgc tgccacttat tactgtcaaa gtggttatta gtgctggt     300 ttgacttttg gagctggcac caatgtggaa atcaaggtgg ttcctctaga tcttcctcct    360
ctggtggcgg tggctcgggc ggtggtgggc aggagcagct ggaggagtcc ggggaggcc    420 tggtccagcc tggggatcc ctgaaactct cctgcaaagc ctctggattc gacttcatta    480
actatggagt aatctgggtc cgccaggctc tgggaaggg gctggagtgg atcgatacaa    540
ttgatcctat ttttggtaac acaatctacg cgagctgggt gaatgaccga ttcaccatct    600
```

```
ccagccacaa cgcccagaac acgctgtatc tgcaactgaa cagtctgaca gccgcggaca    660
cggccaccta tttctgtgcg agatgcgggg atagacgtgg ctggggttat ggttttgatc    720
cctggggccc aggcaccctg gtcaccgtct cctcagggca acctaaggct ccgtcagtca    780
ctagtggccc gggaggcca                                                  799
```

<210> SEQ ID NO 97
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (740)..(740)
<223> OTHER INFORMATION: a, c, t, g, unknown or other
<220> FEATURE:
<221> NAME/KEY: modified_base
<222> LOCATION: (749)..(749)
<223> OTHER INFORMATION: a, c, t, g, unknown or other
<220> FEATURE:
<221> NAME/KEY: modified_base
<222> LOCATION: (751)..(753)
<223> OTHER INFORMATION: a, c, t, g, unknown or other

<400> SEQUENCE: 97

```
ccggccatgg ctgagctcgt gctgacccag actccagcct ccgtgtctga acctgtggga    60
ggcacagtca ccatcaagtg ccaggccagt cagaacattt acagtggtat atcctggtac    120
caacagaagc cagagaaacc tcctacactc ctgatctctg gtgcatccaa tttagaacct    180
ggggtcccac cacggttcag tggcagtgga tctgggacag attacaccct caccattggc    240
ggcgtgcagg ctggagatgc tgccacctac tactgtctag cgttttatag tttcggtagt    300
accgatttga cttttggagc tggcaccaat gtggaaatca aggtggttcc tctagatctt    360
cctcctctgg tggcggtggc tcgggcggtg gtgggcagtc gctggaggag tccggggag    420 gcctcatcaa gccaacggat accctgacac tcacctgcac ggtctctgga ttctccctca    480
gtaccaatgg agtgagttgg gtccgccagg ctccagggag cgggctgaa tggatcggag    540 ccattgatct ttatggtgcc acatattacg cgacctgggc gaaaagccga tccaccatca    600
ccagaaacac caacctaaac acggtgactc tgaaaatgac cagtctgaca gccgcggaca    660
cggccaccta tttctgtgcg agagagggat atggttatcc aaacatctgg ggcccaggca    720
ccctggtcac cgtctcctcn ggcaacctna nnntccgtca gtcactagtg gcccgggagg    780
cca                                                                   783
```

<210> SEQ ID NO 98
<211> LENGTH: 806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (725)..(725)
<223> OTHER INFORMATION: a, c, t, g, unknown or other

<400> SEQUENCE: 98

```
ggcccagccg gccatggctg agctcgatct gacccagact ccatcgtccg tgtctgcagc    60
tgtgggaggc acagtcagca tcagttgcca gtccagtcag agtgtttata ataactactt    120
agcctggtat cagcagaaac cagggcagcc tcccaagctc ctgatctatt atgcatccaa    180
```

| | | |
|---|---|---|
| actggcatct ggggtcccat cgcggttcaa aggcagtgga tctgggacac agttcactct | 240 | |
| caccatcagc gacgtgcagt gtgacgatgc tgccacttac tactgtcaag gcacttttga | 300 | |
| taatggtttg tacaaggctt tcggcggagg gaccgagctg agatcctgg tggttcctct | 360 | |
| agatcttcct cctctggtgg cggtggctcg ggcggtggtg ggcagtcgtt ggaggagtcc | 420 | |
| gggggaggtc tcttcaagcc aacggatacc ctgacactca cctgcacagt ctctggattc | 480 | |
| tccctcagta gctatgcaat aagctgggtc cgccaggctc cagggaacgg gctggaatgg | 540 | |
| atcggataca ttaattacga tggtatcgca tactacgcga gctgggcgaa aagccgatcc | 600 | |
| accatcacca gaaacaccaa cctgaacacg gtgactctga aaatgaccgg tctgacagcc | 660 | |
| gcggacacgg ccacctattt ctgtgcgaga gatgactata ctactcctta tggttatcga | 720 | |
| ttggntctct ggggccaggg caccctggtc accgtctcct cagggcaacc taaggctccg | 780 | |
| tcagtcacta gtggcccggg aggcca | 806 | |

<210> SEQ ID NO 99
<211> LENGTH: 797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

| | | |
|---|---|---|
| ggcccagccg gccatggctg agctcgatat gacccagact ccatcctctg tgtctgcagc | 60 | |
| tgtgggaggc acagtcacca tcaattgcca ggccagtgaa agcattagca acctcttagc | 120 | |
| ctggtatcag cagaaaccag ggcagcctcc caagctcctg atctattctg catccactct | 180 | |
| ggcatctggg gtcccatcgc gtttccgtgg cagtggatct gggacagagt tcactctcac | 240 | |
| catcagtggc atgaaggctg aagatgctgc cacttattac tgtcaaagtg gttattatag | 300 | |
| tactggtgca acttttggag ctggcaccaa tgtggaaatc aaggtggttc ctctagatct | 360 | |
| tcctcctctg gtggcggtgg ctcgggcggt ggtgggcagt cgctggagga gtccggagga | 420 | |
| ggcctggtcc agccgggggg atccctgaaa ctctcctgca aaggctctgg gttcgacctc | 480 | |
| gatagcaatg caatgtgctg ggtccgccag gctccaggga gcgggctgga atggatcgga | 540 | |
| accattacta gtggtggtag cgcatactac gcgagctggg cgaaaagccg atccaccatc | 600 | |
| accagaaaca ccaacctaaa cacggtgact ctgaaaatga ccagtctgac agccgcggac | 660 | |
| acggccacct atttctgtgc gagaggacct acttggggaa ttggagatac ttttcatccc | 720 | |
| tggggcccag gcaccctggt caccgtctcc tcggggcaac taaggctcc gtcagtcact | 780 | |
| agtggcccgg gaggcca | 797 | |

<210> SEQ ID NO 100
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

| | | |
|---|---|---|
| ggcccagccg gccatggctc agcctgtgct gactcagtcg ccctctgtgt ctgccgccct | 60 | |
| gggagcctct gccaagctca cctgcaccct gagcagtgcc cacaagacct acaccattga | 120 | |
| ctggtatcaa cagcagtcag gggaggcccc tcgatacctg atgcagctta agagtgatgg | 180 | |

```
aaactacacc aagggggaccg gggtccctga tcgcttctcg ggctccagct ctggggctga     240
ccgctacttg atcatcccca gcgtccaggc tgatgacgaa gccgactact attgtggtgc     300
agattatagc ggtgggtatg tgtttggcgg agggacccag ctgaccgtca caggtggtgg     360
ttcctctaga tcttcctcct ctggtggcgg tggctcgggc ggtggtgggc aggagcagct     420
ggaggagtcc gggggtcgcc tggtcaagcc tgacgaaacc ctgacactca cctgcacagt     480
ctctggactc tccctgaata attttggagt gagctgggtc cgccaggccc caggaaacgg     540
gctggaatgg atcagagcca ttgattttgg tagtggtagc gcatactacg cgaactgggc     600
gaaaagtcgg tccaccatca ccagcaacac tcgcctgaac acggtgactc tgaaaatgat     660
tagtctgaca gccgcggaca cggccaccta ttttttgttcg agaggagaca tctggggccc     720
aggcaccctg gtcaccgtct tctcagggca acctaaggct ccgtcagtca ctagtggccc     780
gggaggcca                                                              789
```

<210> SEQ ID NO 101

<400> SEQUENCE: 101

000

<210> SEQ ID NO 102
<211> LENGTH: 811
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
gcccagccgg ccatggctga gctcgatatg acccagactc catcctccgt gtctgcagct      60
gtgggaggca cagtcaccat cagttgccag gccagtcaga gtgtttataa taacaacaat     120
ttatcctggt atcagcaaaa accagggcag cctcccaagc tcttgatcta cgatgcatcc     180
aaattggcat ctggggtccc atcgcggttc aaaggcagtg gatctgggac acagttcact     240
ctcaccatta gcgacctgga gtgtgacaat gctgccactt acttctgtca acagggttat     300
gatggtagtg atgttgataa tgtttttcggc ggagggaccg aggtggtggt caaggtggtt     360
cctctagatc ttcctcctct ggtggcggtg gctcggcgg tggtgggcag tcggtgaagg     420
agtccgaggg aggtctcttc aagccaacgg atacccctgac actcacctgc acagtctctg     480 gattctcccct cagtaactat gcaataaact gggtccgcca ggctccaggg gaggggctgg     540
agtggatcgg ctatattgat cctacttttg gtagcacgta ctacgcgagc tgggtgaatg     600
accgattcac catctccagc cacaacgccc agaacacgct gtatctgcaa ctgaacagtc     660
tgacacctgc ggacacggcc acctatttct gtgcgagaga tgatattagt attagtggtt     720
attcatttga catctggggc ccaggcaccc tggtcaccgt ctcctcaggg caacctaagg     780
ctccatcagt cactagtggc ccgggaggcc a                                     811
```

<210> SEQ ID NO 103
<211> LENGTH: 797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

| | |
|---|---|
| ggcccagccg gccatggctg agctcgtgct gacccagact ccaccctccc tatctgcatc | 60 |
| tgtgggagaa actgtcagga ttaggtgcct ggccagtgag ttcctttta atgctgtatc | 120 |
| ctggtatcaa cagaagccag agaaacctcc tacactcccg atctatggtg catccaattt | 180 |
| agaatctggg gtcccaccac ggttcagtgg cagtggatct gggacacagt tcactctcac | 240 |
| catcagcgac ctggagtgtg acgatgctgc cacttactac tgtgcaggcg attatagtga | 300 |
| ttggattat gcttttggcg gggggaccga ggtggtggtc aaggtggttc ctctagatct | 360 |
| tcctcctctg gtggcggtgg ctcgggcggt ggtgggcagt cgttggagga gtccggggga | 420 |
| ggtctcttca gcctggagg atccctgaca ctcacctgca cagtctctgg attcaccatc | 480 |
| actagctacc acatgtgctg ggtccgccag gctccaggga cgggctggg atggatcgga | 540 |
| gccgttagtg ctagcggaca cacatattac gcgaactggg cgaaaagccg atccaccatc | 600 |
| accagagaca ccaacttaaa caccatgact ctgaaaatga ccagtctgac agccgcggac | 660 |
| acggccacct atttctgtgc gacaccatat cctggttatg atattgatcc ctttgacatc | 720 |
| tggggcccag gcaccctggt caccgtctcc tcagggcaac taaggctcc gtcagtcact | 780 |
| agtggcccgg gaggcca | 797 |

<210> SEQ ID NO 104
<211> LENGTH: 800
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

| | |
|---|---|
| ggcccagccg gccatggctg agctcgtgct gacccagact ccatcctccg tgcctgcagc | 60 |
| tgtgggaggc acagtcacca tcgattgcca gtccagtgag agtgtttata ataacaacaa | 120 |
| cttagcctgg tatcagcaga aaccaggca gcctcccaag ctcctgatct acggggcatc | 180 |
| cactctggca tctggggtct catcgcggtt caaaggcagt ggatctggga cagagttcac | 240 |
| tctcaccatc agcgacctgg agtgtgccga tgctgccact tactactgtc aacagggtta | 300 |
| tagtattggt aatgtagata tgctttcgg cggagggacc gagctggaga tcctggtggt | 360 |
| tcctctagat cttcctcctc tggtggcggt ggctcgggcg gtggtgggca gtcgctggag | 420 |
| gagtccgggg gaggtctctt caagccaacg atacccctga cactcacctg cacggtctct | 480 |
| ggattctccc tcagtagcta tggaattact tgggtccgcc aggctccagg aacgggctg | 540 |
| gaatggatcg cgccattgg tagtgatgct aaaacatact acgcgagctg ggcgaaaggc | 600 |
| cgatccacca tcaccggaga caccaacctg aacacggtga ctctgagaat gaccagtctg | 660 |
| acagccgcgc acacggccac ctatttctgt gcgagatatt ttgattggtt taatgtggac | 720 |
| atctggggcc caggcaccct ggtcaccgtc tcctcaggc aacctaaggc tccatcagtc | 780 |
| actagtggcc cgggaggcca | 800 |

<210> SEQ ID NO 105
<211> LENGTH: 797
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

| | |
|---|---|
| ggcccagccg gccatggctg agctcgtgat gacccagact ccagcctctg tggaggtagc | 60 |

```
tgtgggaggc actgtcacca tcaagtgcca ggccagtcag agcattagta gctacttagc    120
ctggtatcaa cagaaaccag gcagcctcc caagctcctg atctacaagg cttccactct    180
ggcatctggg gtcccgtcgc ggttcaaagg cagtggatct gggacacagt tcactctcac    240
catcagcgat gtggtgtgtg acgatgctgc cacttactac tgtgcaggat ataaaggtgg    300
tagtagtgat ggtagtgctt tcggcggagg gaccgagctg agatcctgg tggttcctct     360 agatcttcct cctctggtgg cggtggctcg ggcggtggtg ggcagtcggt gaaggagtcc    420
gagggaggtc tcttcaagcc aacggatacc ctgacactca cctgcacagt ctctggattc    480
tccctcagta gctatggagt gagctgggtc cgccaggctc agggaacgg gctggaatgg     540 atcggagcca ttagtagtgg tggtgacgca tactacgcga gctgggcgac agccgatcc    600 accatcacca gaaacaccaa cctgaacacg gtgactctga aaatgaccag tctgacagcc    660
gcggacacgg ccacctattt ctgtgcgaga cattttggtt atggtactgc tgggggcatc    720
tggggcccag gcaccctcgt caccgtctct caggggcaac ctaaggctcc gtcagtcact    780
agtggcccgg gaggcca                                                  797

<210> SEQ ID NO 106
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
ggcccagccg gccatggctc agcctgtgct gactcagtcg ccctctgcat ctgctgccct     60
gggatcctcg gccaagctca cctgcactct gagcagtgct cacaagacct actatattga    120
atggtatcag cagcagcaag gggaggcccc tcggtacctg atgcaggtta agagtgatgg    180
aagctacacc aaggggaccg gggtccctga tcgcttctcg ggctccagct ctggggctga    240
ccgctacttg atcatcccca gcgtccaggc tgatgacgaa gccgactact attgtggtgc    300
agattatagc ggtgggtatg tgctcggcgg agggacccag ctgaccgtca caggtggtgg    360
ttcctctaga tcttcctcct ctggtggctc gggcggtggt gggcagtcgg tggaggagtc    420 cggggggaggt ctcttcaagc cagcggatac cctgacactc acctgcacag tctctggatt    480
tcccctcagt taccctggag tgagctgggt ccgccaggct ccagggaacg gctggaata    540 catcggattc attaatgctg atggtgactc atactacccg acctgggcga acgccgatc    600 caccatcacc agaaacacca acctgaacac ggtgactctg aaaatgacca gtctcacagc    660
cgcggacacg gccacctatt tctgtgcgag agagggtggc tggggtacat tgtttggtgc    720
ttttgattcc tggggcccag gcaccctagt caccgtcttc tcagggcaac ctaaggctcc    780
gtcagtcact agtggcccgg gaggcca                                       807

<210> SEQ ID NO 107
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
ggcccagccg gccatggctc agcctgtgct gactcagtcg ccctctgcat ctgctgccct     60
```

```
gggatcctcg gccaagctca cctgcactct gagcagtgct cacaagacct actatattga    120
ctggtatcag cagcagcaag gggaggcccc tcggtacctg atgcagcttg ggagtgatgg    180
aagttacacc aaggggaccg ggtccctga tcgcttctcg gctccagct ctggggctga     240 ccgctacttg atcatcccca gcgtccaggc tgatgacgaa gccgactact attgtggttc    300
agattatagc ggtgggtatg tgttcggcgg agggacccag ctgaccgtca caggtggtgg    360
ttcctctaga tcttcctcct ctggtggcgg tggctcgggc ggtggtgggc agtcgctgga    420
ggagtccggg ggaggtctct tcaagccagc ggataccctg acactcgcct gcacagtctc    480
tggattctcc ctcagtactt atggagtgat ctgggtccgc caggctccag gaaggggct     540 ggaatacatc gcatacatta attatagtgg tagtccatac tacgcgagct gggcgaaaag    600
ccgatccacc atcaccagaa acaccaacga gaaaacggtg actctgaaaa tgaccagtct    660
gacagccgcg gacacggcca cctatttctg tgcgagggggt gttcctggtt acaatgcgga   720
tatgggggac atctgggggcc caggcaccct ggtcaccgtc ttctcagggc aacctaaggc   780
tccatcagtc actagtggcc cgggaggcca                                    810
```

<210> SEQ ID NO 108
<211> LENGTH: 818
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (766)..(766)
<223> OTHER INFORMATION: a, c, t, g, unknown or other

<400> SEQUENCE: 108

```
ggcccagccg gccatggctc agcctgtgct gactcagtcg ccctctgtgt ctgccgccct    60
gggagcctct gccaagctca cctgcaccct gagcagtgcc cacaagacct acaccattga    120
ttggtatcag cagcagcaag gggaggcccc tcggtacctg atgcagctta agagtgatgg    180
aagctacacc aaggggaccg ggtccctga tcgcttctcg gctccagct ctggggctga     240 ccgctacttg atcatcccca gcgtccaggc tgatgacgaa gccgactact attgtggtgc    300
agattatagc ggtgggtatg tgttcggcgg agggacccag ctgaccgtca caggtggtgg    360
ttcctctaga tcttcctcct ctggtggcgg tggctcgggc ggtggtgggc agtcggtgga    420
ggagtccagg ggaggtctc ttcaagccaa cggataccct gacactcacc tgcacagtct    480
ctggattctc cctcagtggc tatggagtga gctgggtccg ccaggctcca gggaacgggc    540
tggaatggat cggagccatt agtagtggtg gtagcgcata ctacgcgaga tgggcgaaaa    600
gccgctccac catcaccaga aacaccaacc tgaacacggt gactctgaaa atgaccagtc    660
tgacagccgc ggacacggcc acctatttct gtgcgagagg ttactatact gctattggtg    720
gtacttatga caatgctttt gatccctggg gccaggcac cctggncacc gtctcctcag    780
ggcaacctaa ggccagtcac tagtggcccg ggaggcca                           818
```

<210> SEQ ID NO 109
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
ggcccagccg gccatggctg agctcgatat gacccagact ccaccctccc tgtctgcatc    60
tgtgggagaa actgtcagga ttaggtgcct ggccagtgag gacattggca gtgctatatc   120
ctggtaccaa cagaagccag ggaaacctcc tacactcctg atctatggtg tatttaattt   180
agaatctggg gtcccaccac gattcagtgg cagtggatct gggacagatt acaccctcac   240
cattggcggc gtgcaggctg aagatgctgc cacctactac tgtctaggcg gtgctagtga   300
cagtagtacc ggtttgactt ttggagctgg caccaatgtg gaaatcaagg tggttcctct   360
agatcttcct cctctggtgg cggtggctcg ggcggtggtg ggcagtcggt gaaggagtcc   420
gagggaggtc tcttcaagcc aacggatacc ctgacactca cctgcacagt ctctggattc   480
tccctcagta actatggagt gagctgggtc cgccaggctc agggaacggg ctggaatac    540 atcggcttca ttagtaacgg tggtgccaca ttctacgcga cctgggcgag aagccgagcc   600
accatcacca gaaacaccgg cctgaacacg gtggctctga caatgaccag tctgacagcc   660
gcggacacgg ccacctattt ctgtgtgagg gattctgttg ctacttatgc tactgatgtt   720
gctgcttttg atccctgggg cccaggcacc ctggtcaccg tctcctcagg gcaacctaac   780
tccgtcagtc actagtggcc cgggaggcca                                    810

<210> SEQ ID NO 110
<211> LENGTH: 839
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gcccagccgg ccatggctca gcctgtgctg actcagtcgc cctccctgtc tgcgtctctg    60
ggcacaacgg ccagactcac ctgcaccctg agcactggct acagtgttgg cgagtaccct   120
ttagtgtggc tccagcaggt gccagggagg cctcccaggt atctcctgag cttcacctca   180
gatgaagaca acaccatga ctcttggggc cccacccgct tttctggatc caaagacacc    240
tcagagaata cctttatcct gagcatctct gggctgcagc ccgaggacga ggccgactat   300
tactgtgcta cagctcatgg tagtgataac agcctccatt atgtcttcgg cggaaggacc   360
cagctgaccg tcacaggtgg tggttcctct agatcttcct cctctggtgg cggtggctcg   420
ggcggtggtg ggcagtcggt gaaggagtcc gagggaggtc tcttcaagcc aacggatacc   480
cagacactca cctgcacagt ctctggattc tccctcagta gcaatgcaat aagctgggtc   540
cgccaggctc agggaacggg ctgaaaagc atcggattca ttaatagtgg tggtggcgca   600
tattacgcga cctgggcgaa aagccgatcc accatcacca gaaacaccaa cgagaacacg   660
gtgactctga aaatgaccag tctgacagcc gcggatacgg ccacctattt ctgtgcgaga   720 acacccatt attatgatac ttatgatacc tcatttaaca tatggggccc aggcaccctg   780
gtcaccgtct ctcagggca acctaaggct ccgtcagtca ctagtggccc gggaggcca    839

<210> SEQ ID NO 111
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
```

```
ggcccagccg gccatggctc agcctgtgct gactcagtcg ccctctgcat ctgctgccct     60
gggatcctcg gccaagctca cctgcactct gagcagtgct cacaagacct actatattga    120
atggtatcag cagcagcaag gggaggcccc tcggtacctg atacaactta agagtgatgg    180
aagctacacc aaggggaccg gggtccctga tcgcttctcg ggctccagct ctgggactga    240
ccgctacttg atcatctcca gcgtccaggc tgaggacgaa gccgactact cttgtggtgc    300
agattatagt ggtgggtttg tgttcggcgg agggacccag ctgaccgtca caggtggtgg    360
ttcctctaga tcttcctcct ctggtggcgg tggctcgggc ggtggtgggc agtcgctgga    420
ggagtccggg ggaggtctct tcaagccaac ggatacccctg acactcacct gcacagtctc    480
tggattcgcc ctcaataact acaacataca ctgggtccgc caggctccag ggaacgggct    540
ggaatggatc ggagccattg gtagtagtgg tagcgcatac tacgcgagct gggcgaaaag    600
ccgatccacc atcaccagaa acaccaacct gaacacggtg actctgaaaa tgaccagtct    660
gacagccgcg gacacggcca cctatttctg tgcgagaggt tataattctg atgattctta    720
tctctggggc ccaggcaccc tggtcaccgt ctcctcaggg caacctaagg ctccatcagt    780
cactagtggc ccgggaggcc a                                              801

<210> SEQ ID NO 112
<211> LENGTH: 791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
ccggccatgg ctgagctcgt gctgacccag actccaccct ccctgtctgc atctgtggga     60
ggcacagtca ccataaactg tctggcgagt gagaacgtct acagtgctgt agcctggtat    120
caacagaagc cagggaaacc tcctacactc ctgatctctg gtacatccaa tttagaggct    180
ggggtcccac cacggttcag tggcagtgga tctgggacag attacaccct caccatcggc    240
ggcgtgcagg ctgaagatgc tgccacttac ttctgtcaag gtatagcagt taccctttg    300 acttttggag ctggcaccaa tgtggaaatc aaggtggttc ctctagatct tcctcctcgg    360
tggcggtggc tcgggcggtg tgggcagtc ggtggaggag tccaggggggg aggcctggtc    420 aagcctgggg ataccctcac actcacctgc acagtctctg gattcccct cagcagctac    480 gacatgaact gggtccgcca ggctccaggg gaggggctgg aatggatcgg atgattact    540 tatgatggtt acaatcacta cgcgagctgg gcgaatggcc gatccaccat caccagaaac    600
accaacgaga acgcggtgac tctgaaaatg accagtctga cagccgcgga cacggccacc    660
tatttctgtg cgcgagatta ctataatggt gcttatgttt atgcctttaa catctggggc    720
ccaggcaccc tggtcaccgt ctcctcaggg caacctaagg ctccatcagt cactagtggc    780
ccgggaggcc a                                                         791

<210> SEQ ID NO 113
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggtggttcct ctagatcttc ctcctctggt ggcggtggct cggcggtgg tgggcagtcg     60
```
gtggaggagt ccrgg                                                    75

<210> SEQ ID NO 114
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggtggttcct ctagatcttc ctcctctggt ggcggtggct cgggcggtgg tgggcagtcg   60
gtgaaggagt ccgag                                                    75

<210> SEQ ID NO 115
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggtggttcct ctagatcttc ctcctctggt ggcggtggct cgggcggtgg tgggcagtcg   60
ytggaggagt ccggg                                                    75

<210> SEQ ID NO 116
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ggtggttcct ctagatcttc ctcctctggt ggcggtggct cgggcggtgg tgggcagsag   60
cagctggwgg agtcc                                                    75

<210> SEQ ID NO 117
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tggtgttggc ctcccgggcc actagtgact gayggagcct taggttgc                48

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tggtgttggc ctcccgggcc acta                                          24

<210> SEQ ID NO 119
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gggcccagcc ggccatggct gagctcgtgm tgacccagac tcca         44

<210> SEQ ID NO 120
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gggcccagcc ggccatggct gagctcgatm tgacccagac tcca         44

<210> SEQ ID NO 121
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gggcccagcc ggccatggct gagctcgtga tgacccagac tgaa         44

<210> SEQ ID NO 122
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gggcccagcc ggccatggct gagctcgtgc tgactcagtc gccctc       46

<210> SEQ ID NO 123
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gggcccagcc ggccatggct cagcctgtgc tgactcagtc g            41

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tactcagggc ccagccggcc atggctga                          28

<210> SEQ ID NO 125
<211> LENGTH: 41
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 125
ggaagatcta gaggaaccac caggatctcc agctcggtcc c                          41

<210> SEQ ID NO 126
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ggaagatcta gaggaaccac cttgatttcc acattggtgc c                          41

<210> SEQ ID NO 127
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ggaagatcta gaggaaccac cttgacsacc acctcggtcc c                          41

<210> SEQ ID NO 128
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggaagatcta gaggaaccac cacctgtgac ggtcagctgg gtcc                       44

<210> SEQ ID NO 129
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
taagcagaat tcggcccagc cggccgcggt gggaacacta gga                        43

<210> SEQ ID NO 130
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
agcagaattc tggcccagcc ggccgcggtg ggaacactag                            40

<210> SEQ ID NO 131
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
agcagaattc taggcccagc cggccgcggt gggaacacta                              40

<210> SEQ ID NO 132
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ctctagatct ggcctcccgg gccttttat ataccacagc cagtttg                       47

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ctctagatct aggcctcccg ggccttttta tataccacag                              40

<210> SEQ ID NO 134
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ctctagatct atggcctccc gggcctttt atataccaca                               40

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
aacataaaga aaggcccggc                                                   20

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gccttatgca gttgctctcc a                                                 21

<210> SEQ ID NO 137
<211> LENGTH: 2793
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
atggggcacc atgctccttg ggatgttgat gatctgtagt gctgcagata aattgtgggt      60
cacagtctac tatggggtac ctgtgtggaa agaagcaacc accactctat tttgtgcatc     120
agatgctaaa gcatatgata cagaggtaca taatgtttgg gccacgcatg cctgtgtacc     180
cacagacccc aacccacaag aagtagtatt ggaaaatgtg acagaaaatt ttaacatgtg     240
gaaaaatgac atggtagaac aaatgcatga ggatataatc agtttatggg atcaaagcct     300
aaagccatgt gtaaaattaa ccccactctg tgtcacttta aattgcaatg atgtcaataa     360
taatagtact atcaacaatg aactactaa tgccactagt catagtgggg aaaaataga      420
gagaggagaa ataaaaaatt gctctttcaa tgtcaccaca acataaaaa ataagctgca      480
gaaagaatat gcactgtttt ataagcttga tctagtacca acagatgata taattctag     540
atataggttg atacattgta ataccttagt cattacacaa gcctgtccaa aggtatcctt     600
tgagccaatt cccatacatt attgtgcccc ggctggtttt gcgattctaa agtgcaaaga     660
taggaatttc acaggaaaag acaatgtaaa aaatgtcagc acagtacaat gtacacatgg     720
cattaggcca gtagtgtcaa ctcaactgct gttaaatggc agtctagcag aagatggggt     780
agtaattaga tctgccaata tcacagacaa tactaaaacc ataatagtac agttgaagga     840
agctgtagaa attaattgta caagacccaa taacaataca aggaaaagta aactatagg     900
accagggaga gcattttgga caacaggagg aataatagga gatataagac aagcacattg     960
taaccttagt agcacaaaat ggaataacac tttaagacag atagctacaa aattaagaga    1020
acaatttggt aacaaaacaa tagtttttaa tcaatcctca ggaggggacc aagaaattgt    1080
gatgcacact tttaattgtg gaggggaatt tttctactgt agtacaacac aactgtttaa    1140
tagtacttgg attgcaaata agactgggaa tgatactgga ggatcaaatg gaactattac    1200
acttccatgc agaataaaac aaattgtaaa catgtggcag gaagtaggaa aagcaatgta    1260
tgcccctccc atcaaaggac aaattagatg ttcatcaaac attacaggac tgctattatt    1320
aagagatggt ggtaagaata acgggacagg aaacatgaca gaaatcttca gacctggagg    1380
aggagatatg agggacaatt ggagaagtga attatataaa tataaagtag taaaaattga    1440
accattagga gtagcaccca ccaaggcaaa gagaagagtg gtgcagagag aaaaaagagc    1500
ggtgggaaca ctaggagcct tgttccttgg gttcttggga acagcaggaa gcactatggg    1560
cgcagcatca ctaacgctga cggtacaggc cagactatta tgcctggta tagtgcaaca    1620
gcaaaacaat ttgctgagag ctattgaggc gcaacagcat ttgttgcaac tcacagtctg    1680
gggcatcaag cagctccagg caagagtcct ggctatggaa agatacctac aggatcaaca    1740
gctcctaggg atttggggtt gcgctggaaa actcatttgc accacagctg tgccttggaa    1800
tactagttgg agtaataaat ctctggatca gatttggaat aacatgacct ggatgcaatg    1860
ggaaagagaa attgacaatt acacacacac aatatacagc ttaattgaag aatcgcagaa    1920
ccaacaagaa aaaatgaac aagaattatt ggaactagac aagtgggcaa gtttgtggaa    1980
ttggtttgac ataacaaact ggctgtggta tataaaaata ttcataatgg tagtaggagg    2040
cttagtaggt ttaagaatag ttttgctgt actttctata gtaatagag ttaggcaggg     2100
atactcacca ttatcgttgc agacccgatt cccagtccag aggggacccg acaggcccga    2160
aggaatcgaa gaagaggtg gagagagaga cagagacaga tccggtcgat tagtgaccgg    2220
attcttacct cttatctggg acgacctgcg gagcctgtgc ctcttcagct accgccgctt    2280
```

```
gagagactta ctcttgattg cagcgaggat tgtggaactt ctgggacgca gggggtggga    2340
actcctcaaa tattggtgga atctcctaaa atattggagt caggaactaa agaatagtgc    2400
tgtcagcttg tacaacgcca cagctatagc agtagctgag ggaacagata gggttataga    2460
aatagtaaga agaaccttta gagctattat ccacatacct agaagaataa gacagggctt    2520
ggaaagggct ttgctataag atgggtggca agtggtcaaa aagtagtgtg gttggatggc    2580
ctgagataag agaaagaatg agacgaaccg agccacgaac cgagccagca gcagagggg    2640 tgggagcagc atctcgagac ctagaaaaac atggagcaat cacaagtagc aatacagcag    2700
ctactaatgc tgcttgtgcc tggctagaag cacaagaaga agaggaagtg ggttttccag    2760
tcagacctca ggtacccttta agaccaatga cct                                2793
```

POLYCLONAL ANTIBODIES PRODUCED USING HIV-1 TRIMERIC ENVELOPE GLYCOPROTEIN SUBUNITS

CROSS REFERENCE TO RELATED APPLICATIONS

This application is a divisional of U.S. application Ser. No. 14/771,337 filed Aug. 28, 2015, now abandoned, which is a 371 of International Application No. PCT/US14/19612 filed Feb. 28, 2014 which claims the benefit of U.S. Provisional Application No. 61/770,974, filed Feb. 28, 2013. The entire teachings of these applications are incorporated herein by reference for all purposes.

BACKGROUND OF THE INVENTION

Field of the Invention

The present invention relates to novel HIV-1 antigenic compositions that can be used to produce antibodies that neutralize multiple strains of HIV-1, the use of such antigenic compositions to induce an immune response in a subject, and the use of such antibodies in prophylactic and therapeutic methods.

Description of the Related Art

Acquired immune deficiency syndrome (AIDS) is a life-threatening clinical condition caused by infection with the Human Immunodeficiency Virus 1 (HIV-1) (Killian M S, Levy J A, *European Journal of Immunology* 2011, 41: 3401-3411). AIDS was first described in a set of unusual clinical cases the early 1980s and its causative agent was identified shortly thereafter. Since then, major efforts have been made to develop therapies and vaccines for HIV/AIDS. To date, clinically beneficial antiretroviral drugs have been developed that delay the onset of AIDS, but an effective vaccine remains elusive, as do immune-based therapies and a cure for the infection.

Importantly, the current standard treatment of care for HIV-infected individuals has significant limitations (Reust C E, *American Family Physician* 2011, 83: 1443-1451). The clinically approved antiretroviral drugs require daily life-long application; non-adherence is common. They do not cure HIV-1 infection. Drug-resistant HIV-1 strains can emerge in the presence of antiretroviral drugs. Numerous toxicities caused by the long-term usage of antiretroviral drugs have been reported. HIV-1-infected individuals can progress to AIDS while receiving antiretroviral medication. Antiretroviral drugs are expensive and their monitored administration poses a difficult challenge in many parts of the world.

HIV-1 infection creates significant challenges for the development of a vaccine and immune-based therapies (Q Yu et al., *Cellular and Molecular Immunology* 2010, 7: 334-340). Unlike many other viruses that infect humans, HIV permanently integrates its viral nucleic acid genome into host cell chromosomes. Following the initial (acute) infection, HIV-1 spreads throughout the host while its genetic composition mutates at a high rate. Thus, vaccines and other immune-based clinical interventions must be effective against a variety of HIV-1 strains or genetic variants. Therefore, a necessary feature of an effective vaccine for HIV/AIDS is the ability to elicit broadly neutralizing antibodies (BNAb), or antibodies that target genetically distinct HIV-1 strains.

Among the proteins expressed by HIV-1, the envelope (Env) proteins are displayed on the surface of the virus, enable the virus to attach to host cells, and are indispensible for infectivity (Q Yu et al., *Cellular and Molecular Immunology* 2010, 7: 334-340). The HIV-1 genome encodes a single envelope nucleic acid sequence that is transcribed and translated as two glycoproteins: a transmembrane gp41 (~41 kDa) and an external gp120 (~120 kDa). Both proteins assemble as trimeric subunits, with the gp120 subunits being noncovalently attached to the membrane-bound gp41 subunits. Together, these gp41 and gp120 subunits constitute an envelope 'spike'.

Several features of the envelope spike make it particularly challenging for vaccine and antibody development (Q Yu et al., *Cellular and Molecular Immunology* 2010, 7: 334-340). First, the amino acid sequence of the envelope spike is highly variable, due to the high mutation rate of HIV-1. Second, HIV-1 displays a relatively low number of envelope spikes (~10) per virion. Third, its noncovalent assembly renders the envelope spike physically unstable. Fourth, its dual-trimeric assembly creates a complex protein structure. And fifth, the envelope proteins are heavily glycosylated, masking potential antibody binding sites.

A variety of methods are currently being used to generate antibodies specific for HIV. Because it is difficult to produce large amounts of natural HIV-1 in primary cell culture and because the envelope proteins on the virus are "low-abundance" proteins, the field is largely using recombinant proteins, recombinant viruses and/or long-term cell lines to elicit and to screen for anti-HIV-1 proteins. Recombinant proteins are unproven to possess the native conformational determinant(s) that can be targeted by highly effective antibodies or used for effective vaccination. Another approach used in the field is to isolate antibodies directly from the blood of persistently HIV-1-infected individuals. The limitation of such antibodies is implied in the nature of their source. Screening for anti-HIV-1 envelope antibodies is frequently performed using recombinant viruses, virus lysates, and/or recombinant proteins and peptides. These viruses and virus products are unproven to contain the native conformational determinant(s) that can be targeted by highly effective antibodies.

SUMMARY OF THE INVENTION

Embodiments of the present disclosure include methods (and corresponding products) of reducing HIV-1 transmission and disease progression by providing a system for producing a retroviral particle depleted of capsid proteins and RNA, using said retroviral particles to elicit antibodies in a subject, and administering said antibodies and/or said retroviral particles to a subject.

Accordingly one aspect of the invention is a composition of matter including isolated antigen binding proteins (ABPs). The isolated ABPs selectively bind to an epitope on an HIV-1 trimeric envelope glycoprotein subunit (TEGS). In an embodiment, the TEGS is prepared by obtaining infectious HIV-1 virus particles from human CD4+ cell culture grown in serum-free media. In an embodiment, the infectious particles are Fiebig I/II isolates or founder virus. The TEGS is further prepared by contacting the infectious HIV-1 virus particles with agents that selectively remove viral RNA and viral capsid protein while retaining viral envelope protein in a non-denatured conformation, such that the agents do not chemically fix or cross-link the envelope protein. In one embodiment, the agents include cyclodextrin. The TEGS is further prepared by isolating protein from the HIV-1 virus particles such that the isolated protein includes non-infectious complexes comprising TEGS, which includes HIV-1 envelope, gp120, and gp41 proteins that are not chemically fixed or cross-linked and substantially free of HIV-1 capsid protein, reverse transcriptase and RNA.

1. In some embodiments, the ABPs neutralize infectious HIV-1 particles, such as particles from an HIV R5 strain and an HIV X4 strain. In another embodiment, the ABPs compete in binding to TEGS with a reference antibody or antibody fragment comprising a heavy chain CDR selected from the group consisting of SEQ ID NO: 1 SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, and SEQ ID NO: 73, and a light chain CDR selected from the group consisting of SEQ ID NO: 2, SEQ ID NO: 4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, and SEQ ID NO:74.

In another embodiment, the ABPs compete in binding to TEGS with a reference antibody or antibody fragment having a nucleotide sequence selected from the group consisting of: SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO: 103, SEQ ID NO: 104, SEQ ID NO:105, SEQ ID NO: 106, SEQ ID NO: 107, SEQ ID NO: 108, SEQ ID NO: 109, SEQ ID NO: 110, SEQ ID NO:111, and SEQ ID NO: 112.

The reference antibody or ABPs may be recombinant antibodies, chimeric antibodies, humanized antibodies, single-chain antibodies, synthetic antibodies, CF antibodies, polyclonal antibodies, human polyclonal antibodies, bispecific antibodies, or fragments thereof. In a further embodiment, the ABPs are administered to a subject at a therapeutic amount. In yet another embodiment, the ABPs are derived from a phage display.

Another aspect of the invention is an antigenic composition capable of producing neutralizing HIV-1 antibodies including non-infectious complexes. The composition includes a TEGS that comprises HIV-1 envelope, gp120, and gp41 proteins that are not chemically fixed or cross-linked and substantially free of HIV-1 capsid protein, reverse transcriptase and RNA, such that the composition is non-infectious and substantially free of serum proteins. In a further embodiment, the composition is capable of eliciting antibodies that neutralize infectious HIV-1 particles, such as particles from an HIV-1 R5 strain and an HIV-1 X4 strain.

In another embodiment, the composition is administered to a subject such that a neutralizing HIV-1 antibody is produced. The subject can be human or non-human. In a further embodiment, a human subject has a homozygous deletion of 32 base pairs in the gene encoding CCR5 coreceptor for HIV-1. In some embodiments, polyclonal antibodies that neutralize HIV-1 are recovered from the subject.

In an embodiment, a cell line that produces neutralizing HIV-1 antibody is prepared, and the cell line includes splenocytes or B cells isolated from the subject. In some embodiments, the cell line includes immortalized cells or transformed cells. In a further embodiment, the cell line is a hybridoma that is grown in cell culture, and neutralizing HIV-1 antibody is recovered from the cell culture. In a further embodiment, a nucleic acid encoding at least one CDR from a gene encoding a neutralizing HIV-1 antibody is isolated from the hybridoma. Another aspect of the invention is a method of producing ABPs that neutralize HIV-1, by culturing a cell comprising a gene encoding at least part of the ABPs under conditions such that the gene is expressed and the ABPs are recovered.

Another aspect of the invention is an improvement of an immunoassay method for the detection of anti-HIV-1 antibodies. The improvement includes using at least one antigen that is an HIV-1 TEGS isolated from an immunogenic composition as described above. In an embodiment, the antigen is bound to an immunoassay support. In another embodiment, the antigen is in solution. In a further embodiment, the antigen includes a detectable label.

Another aspect of the invention is a method for preparing an immunogenic, inactivated virus composition, by obtaining an infectious virus particle that includes RNA, an envelope protein, a capsid protein, a reverse transcriptase, a gp120 protein, and a gp41 protein. In some embodiments, the virus composition includes TEGS, which includes the envelope, the gp120 protein, and the gp41 protein. In other embodiments, the virus particle is a Fiebig I/II isolate or transmitted founder virus, or the virus particle is obtained from a mammalian subject that lacks antibodies against the virus particle, or the virus particle is an HIV particle, an FIV particle, or an EIAV particle. In some embodiments, the virus particle comprises an HIV-1 or an HIV-2 particle. The method for preparing the immunogenic, inactivated virus composition further involves contacting the infectious virus particle with agents that selectively remove the RNA, the capsid protein and the reverse transcriptase, while retaining the envelope protein in a non-denatured conformation, such that the agents do not chemically fix or cross-link the envelope protein, thus producing an immunogenic, inactivated virus composition. In an embodiment, the agents include cyclodextrin and/or Benzonase.

In one embodiment, the infectious virus particle includes multiple distinct HIV isolates. In a further embodiment, the distinct HIV isolates are distinct HIV types, distinct HIV groups, or distinct HIV clades. In another embodiment, preparation of the TEGS comprises obtaining a DNA sequence of the TEGS, cloning the DNA sequence into an expression vector, and expressing the cloned DNA sequence to obtain TEGS proteins. In another embodiment, a product is produced by one of the above methods, such that the product is capable of eliciting antibodies against the trimeric envelope glycoproteins in a mammalian subject inoculated with the product. In a separate embodiment, the antibodies are virus neutralizing antibodies. In one embodiment, antibodies present in a sample from a subject are quantified by contacting the sample with the product, and determining the specific binding of antibodies in the sample to the product. In another embodiment, an immune response is generated in a subject by administering an immunogenic amount of the product to the subject. In a further embodiment, the subject is genetically resistant to viral infection. In a further embodiment, the subject is receiving antiretroviral therapy. In a further embodiment, the immune response includes a neutralizing response against the infectious virus particle.

In another embodiment, an antibody is generated by administering to a subject an immunogenic amount of the above product, and isolating the antibody, such that the antibody specifically binds to the product. In a separate embodiment, an antibody is generated by administering to a subject an immunogenic amount of the above product, producing a hybridoma using splenocytes or B cells isolated from the immunized subject, such that the hybridoma produces a monoclonal antibody that specifically binds to the product, and isolating the monoclonal antibody. In another embodiment, a monoclonal antibody specifically binds to the above product. In a further embodiment, the antibody is capable of neutralizing in vivo the infectious virus particle. In another embodiment, a polyclonal antibody preparation specifically binds to the above product. In a further embodiment, the antibody preparation is capable of neutralizing in vivo the infectious virus particle.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Definitions

Figure 1:
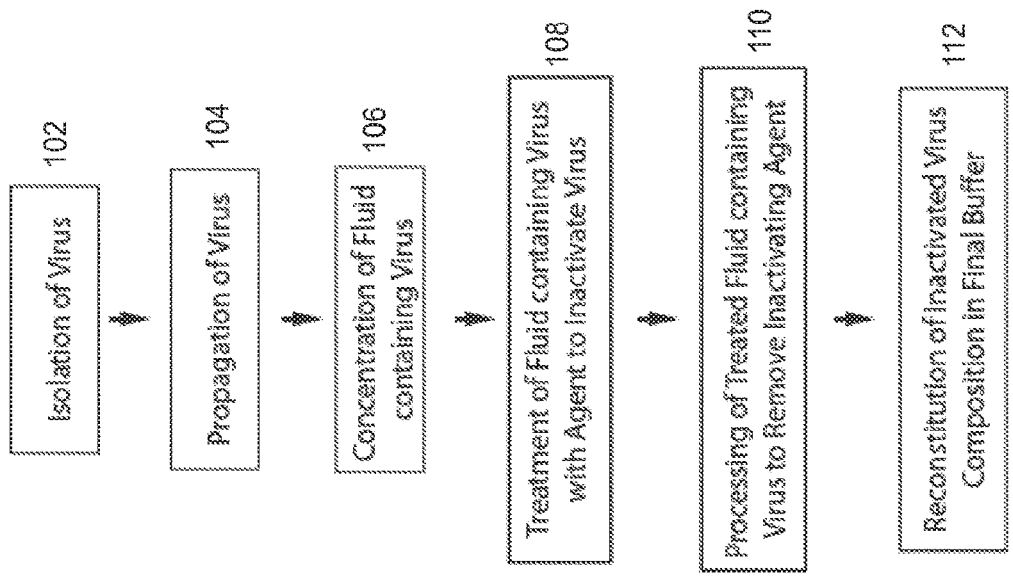
FIG. 1 illustrates a flowchart that summarizes a method for producing TEGS for generating neutralizing antibodies, in accordance with an embodiment of the invention.

Terms used in the claims and specification are defined as set forth below unless otherwise specified.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use. In some embodiments, an isolated protein has undergone post-translational modifications and is glycosylated.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "naturally occurring" as used throughout the specification in connection with biological materials such as polypeptides, nucleic acids, host cells, and the like, refers to materials which are found in nature or a form of the materials that is found in nature.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987); Chothia et al., Nature, 342:878-883 (1989), or International Immunogenetics Information System (IMGT; Lefranc et al., Nucleic Acids Research 2009 37: D1006-D1012; doi:10.1093/nar/gkn838).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition, the IMGT definition, and the contact definition.

The Kabat definition is a standard for numbering the residues in an antibody and is typically used to identify CDR regions. See. e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

IMGT®, the international ImMunoGeneTics information System® (http://www.imgt.org), is a global reference in immunogenetics and immunoinformatics, created in 1989 by Marie-Paule Lefranc (Université Montpellier 2 and CNRS). IMGT® is a high-quality integrated knowledge resource specialized in the immunoglobulins (IG) or antibodies, T cell receptors (TR), major histocompatibility (MH) of human and other vertebrate species, and in the immunoglobulin superfamily (IgSF), MH superfamily (MhSF) and related proteins of the immune system (RPI) of vertebrates and invertebrates. IMGT® provides a common access to sequence, genome and structure Immunogenetics data, based on the concepts of IMGT-ONTOLOGY and on the IMGT Scientific chart rules. IMGT® works in close collaboration with EBI (Europe), DDBJ (Japan) and NCBI (USA). IMGT® consists of sequence databases, genome database, structure database, and monoclonal antibodies database, Web resources and interactive tools.

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

Some species of mammals also produce antibodies having only a single heavy chain.

Each individual immunoglobulin chain is typically composed of several "immunoglobulin domains," each consisting of roughly 90 to 110 amino acids and having a characteristic folding pattern. These domains are the basic units of which antibody polypeptides are composed. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. IgG heavy chains, for example, contain three C region domains known as CH1, CH2 and CH3. The antibodies that are provided can have any of these isotypes and subtypes.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The term "antigen" refers to a molecule or a portion of a molecule capable of being bound by a selective binding agent, such as an antigen binding protein (including, e.g., an antibody or immunological functional fragment thereof). In some embodiments, the antigen is capable of being used in an animal to produce antibodies capable of binding to that antigen.

The term "epitope" includes any determinant capable being bound by an antigen binding protein, such as an antibody or to a T-cell receptor. An epitope is a region of an antigen that is bound by an antigen binding protein that targets that antigen. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

An "antigen binding protein" ("ABP") as used herein means any protein that binds a specified target antigen. "Antigen binding protein" includes but is not limited to antibodies and binding parts thereof, such as immunologically functional fragments. Peptibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')2, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. In some embodiments, antibody fragments are produced by treatment of an immunoglobulin with a protease such as pepsin or papain. The immunoglobulin may be digested before and after a disulfide bond between two H chains in a hinge region. As will be appreciated by one of skill in the art, an antigen binding protein can include nonprotein components.

Certain antigen binding proteins are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. These various antigen binding proteins are further described herein.

An "Fc" region comprises two heavy chain fragments comprising the CH1 and CH2 domains of an antibody. The two heavy chain fragments are held together by two or more disulfide bonds and by hydrophobic interactions of the CH3 domains.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

An "immobilized antibody" is an antibody supported on an insoluble carrier via physical adsorption, chemical bond, or some other method. An immobilized antibody can be used to detect, quantify, separate, or purify an antigen contained in a sample (for example, a body fluid sample such as plasma, a culture supernatant, or a centrifuged supernatant.). In one embodiment, an insoluble carrier used to immobilize the antibody includes a plastic consisting of a polystyrene resin, a polycarbonate resin, a silicon resin, or a nylon resin; a plate consisting of a substance insoluble in water, such as glass; a product having an inner volume, such as a test tube; and either beads, a ball, a filter, or a membrane. In another embodiment, an insoluble carrier used to immobilize the antibody includes insoluble carriers used in affinity chromatography, such as a cellulose carrier, an agarose carrier, a polyacrylamide carrier, a dextran carrier, a polystyrene carrier, a polyvinyl alcohol carrier, a polyamino acid carrier, or a porous silica carrier. An immobilized antibody can be sensitized to an insoluble carrier such as a solid phase carrier, or as a labeled antibody that is labeled with some labeling substance.

The term "labeled antibody" is an antibody that is labeled with a labeling substance. A labeled antibody can be used to detect or quantify an antigen contained in a sample (for example, a body fluid sample such as plasma, a culture supernatant, or a centrifuged supernatant). The labeling substance is not particularly limited, as long as it is able to bind to an antibody via a physical bond, such as a chemical bond. The labeling substance can be an enzyme, a fluorescent substance, a chemoluminescent substance, biotin, avidin, or a radioisotope, for example. More specifically, the labeling substance can be an enzyme such as peroxidase, alkaline phosphatase, β-D-galactosidase, glucose oxidase, glucose-6-phosphate dehydrogenase, alcohol dehydrogenase, malate dehydrogenase, penicillinase, catalase, apoglucose oxidase, urease, luciferase or acetylcholine esterase; a fluorescent substance such as fluorescein isothiocyanate, phycobiliprotein, rare earth metal chelate, dansyl chloride or tetramethylrhodamine isothiocyanate; a radioisotope such as 3H, 14C, 125I or 131I; or biotin, avidin or chemoluminescent substances. Methods for binding a labeling substance to an antibody include a glutaraldehyde method, a maleimide method, a pyridyl disulfide method or a periodic acid method.

A labeling substance such as a radioisotope or a fluorescent substance generates detectable signals on its own. Other labeling substances such as enzymes, chemoluminescent substances, biotin, and avidin are not able to generate detectable signals on their own, but generate detectable signals by reacting with one or more types of other substances via a colorimetric method, a fluorescence method, a bioluminescence method, or a chemoluminescence method, for example. In an embodiment, biotin is used as a labeling substance, and reacts with at least avidin or enzyme-modified avidin.

An antigen binding protein is "selective" when it binds to one target more tightly than it binds to a second target. Methods of determining ABP selectivity or binding specificity are well-known in the art.

The term "recombinant antibody" refers to an antibody engineered by recombinant DNA technology in a cell line, without involving the use of animals. The term "complement-fixing (CF) antibody" refers to an antibody that is combined with an antigen, leading to opsonization or cell lysis.

The term "neutralizing antigen binding protein" or "neutralizing antibody" refers to an antigen binding protein or antibody, respectively, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding protein that prevents the protein to which it is bound from performing a biological function. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99%/o or more (as measured in an in vitro competitive binding assay). In some embodiments, the neutralizing ability is characterized and/or described via a competition assay. In some embodiments, the neutralizing ability is described in terms of an IC50 or EC50 value. The term "broadly neutralizing HIV-1 antibody" refers to a neutralizing antibody that neutralizes more than one HIV-1 strain.

Preferably, the neutralizing antigen binding proteins or neutralizing antibodies of the present invention neutralize infectivity; i.e., the antigen binding protein or antibody reduces or eliminates viral infectivity. Infectivity neutralization can be tested in a standard assay, for example, by incubating the antibody or ABP of interest with viral isolates and susceptible human cells, and then measuring viral levels in a RT-PCR assay. Such an assay is described in Example 8 (below).

In an embodiment, neutralizing antibodies to an HIV-1 virus particle product are generated by immunizing a subject with a concentrated HIV-1 virus particle product, such as TEGS. In a preferred embodiment, the concentrated HIV-1 virus particle product was produced by propagating the virus in serum-free medium, concentrating the virus, and treating the virus with agents to inactivate the virus. In some embodiments, the concentration step involves using molecular weight cutoff (MWCO) filters. In other embodiments, the agents for inactivating the virus can include a cyclodextrin or Benzonase.

The term "target" refers to a molecule or a portion of a molecule capable of being bound by an antigen binding protein. In certain embodiments, a target is an antigen. The use of "antigen" in the phrase "antigen binding protein" simply denotes that the moiety that comprises the antigen can be bound by an antibody.

The term "compete" when used in the context of antigen binding proteins (e.g., neutralizing antigen binding proteins or neutralizing antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen. Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see. e.g., Harlow and Lane, 1988. Antibodies, A Laboratory Manual. Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%/o, 90-95%, 95-97%, or 97% or more.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "virus" refers to a small infectious agent that only replicates inside the cell of another organism. A virus particle consists of genetic material made from either DNA or RNA, a protein coat, and optionally a lipid envelope. The term "retrovirus" refers to a virus that uses RNA as its genetic component.

The term "expansion" refers to propagation of the virus and or cells in vitro.

The term "trimeric envelope glycoprotein subunit" or "TEGS" refers to protein complexes of trimeric gp120 bound to the membrane-anchored trimeric gp41. Monomeric gp120 and gp41 are HIV envelope proteins having masses of 120 and 41 kilodaltons (kDa) respectively. Thus, TEGS are predicted to have a mass of several hundred kDa. TEGS function in the attachment and entry of HIV into the cell. Proposed is that TEGS contain a highly conserved protein shape or 'conformational determinant' that is required for HIV attachment and entry. Antibodies that bind and obscure the 'conformational determinant' can be broadly neutralizing antibodies. Non-neutralizing antibodies that bind to TEGS can also help to reduce infectious virus particles and therefore can also be clinically beneficial.

The term "non-infectious" refers to the infectivity state of all components of the fluids harvested from cultures containing virus-infected cells. Non-infectious material, when used in standard infectivity assays with blood cells, permissive cell lines, and/or animal models, produces no detectable virus replication.

The term "fluid" refers to cell culture conditioned medium. In addition to the input cell culture medium, a "fluid" can contain modifications to the constituents of the input cell culture medium, cells, cellular debris, products secreted by cells, products of cellular breakdown, intact viruses, partial viruses, virus proteins, and contaminants.

The term "agent" is used herein to denote a chemical compound, a mixture of chemical compounds, a biological macromolecule, or an extract made from biological materials.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, scrum, urine, cells, organs, tissues, bone, bone marrow, lymph nodes, and skin.

The term "prevent" does not require the 100% elimination of the possibility of an event. Rather, it denotes that the likelihood of the occurrence of the event has been reduced in the presence of the compound or method.

The term "enhancing antibody" refers to an antibody that can promote the replication of a virus, virus subset, or molecular virus construct. This phenomenon facilitates antibody-dependent enhancement (ADE) of infection and can involve complexes of microorganisms and antibodies, interactions of antibodies with Fc receptors (FcR), complement proteins, and complement receptors (CR).

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Methods of the Invention

Viruses and virus derivatives, natural or synthetic, when used for immunization are appreciated for their abilities to elicit protective immune responses. The resulting protection can be attributed to the production of antibodies that are specific for components of the immunogen. Thus, the use of viruses or virus products can enable the production of virus-specific antibodies. The viruses and virus derivatives can be useful in the form of an immunogen or vaccine. The resulting antibodies can also be used for research and clinical benefit. The present virus particle product can be used to elicit virus-particle-specific antibodies. The present invention relates to: producing trimeric envelope glycoproteins derived from HIV, using these glycoproteins for use in clinical and research assays for immunization purposes, and producing antigen-binding proteins (ABPs) (for example, antibodies) that have a neutralizing activity on a wide range of HIV strains. The present invention is not limited to any known variant of HIV and it can include future strains that can arise from recombination of present circulating forms.

Practices of the method of the present invention include extracting cholesterol from a virus membrane and depleting capsid proteins and RNA, and creating a virus particle product. In some examples, the virus is an infectious retroviral particle that comprises RNA, an envelope protein, a capsid protein, a gp120 protein, and a gp41 protein. In one embodiment, the virus particle product is prepared from HIV-1 cultured in primary human cells. The HIV stocks can be prepared from HIV isolated from individuals undergoing acute HIV infection (such that the individuals' blood is HIV RNA positive and HIV antibody negative). In a further embodiment, the primary human cells are CD4+ blood cells cultured in a serum-free medium.

In an embodiment, the virus particle product is processed to render the HIV-1 non-infectious. In one embodiment, the virus particle product is not exposed to chemical compounds, such as formaldehyde, ethyleimine, or beta-propiolactone that can modify or disrupt the natural envelope protein structure. The virus particle product retains TEGS (trimeric envelope glycoprotein subunit) in its natural state as evidenced by its ability to bind both anti-gp120 and anti-gp41l antibodies (Vyas G N et al., *Biologicals,* 2012 40: 15-20). One method of preparing the virus particle product includes contacting an infectious retroviral particle with an agent (for example, a cyclodextrin) that selectively removes RNA, reverse transcriptase and capsid protein while retaining the envelope protein in a non-denatured conformation, wherein said agent does not chemically fix or cross-link said envelope protein, thereby producing an immunogenic, inactivated retroviral composition. Any residual DNA/RNA is degraded by hydrolysis with protease-free Benzonase®. Thus, the immunogenic, inactivated retroviral composition comprises a trimeric envelope glycoprotein subunit, said subunit comprising said envelope, said gp120, and said gp41 proteins. The native HIV-1 envelope structure is retained, and said gp120 subunits are noncovalently attached to said gp41 proteins. In another embodiment, supernatant from the serum-free cell culture of HIV-infected CD4+ cells is concentrated and treated with beta-cyclodextrin and with or without Benzonase to render the HIV non-infectious.

The virus particle product can be derived from HIV obtained from HIV-infected by seronegative subjects, or further derived from a plurality of HIV types, including HIV-1, HIV-2, groups, and clades. The virus particle product can also be obtained from a mammalian subject that lacks antibodies against said infectious retroviral particle, or from animal lentiviruses such as Feline Immunodeficiency Virus (FIV) or Equine Infectious Anemia (EIAV). The virus particle product can also be a Fiebig VII isolate or founder virus.

The virus particle product is capable of eliciting neutralizing antibodies or enhancing antibodies in a mammalian subject inoculated with said product. For example, an immunogenic amount of the virus particle product can be administered to a subject to generate an anti-virus particle product antibody (for example, a TEGS-specific antibody), after which antibody can then be isolated. In some cases, said subject is a camelid subject. In a preferred embodiment, the anti-virus particle product antibody has neutralizing activity against at least one HIV strain, and more preferably has neutralizing activity against a broad range of HIV strains, including the R5 strain and the X4 strain.

In an embodiment, virus-particle-specific antibodies are elicited in animals. For example, to elicit antibodies, animals (e.g., mice, rabbits, camelids) can be immunized with TEGS or iTEGS. During the antibody production protocol (e.g., 8+ weeks), animals receive multiple (e.g., 3-5) immunizations. The resulting animal serum can contain virus-particle-specific antibodies. Compounds such as Freund's Adjuvant, aluminum salts, CpG, and other adjuvants can be administered along with the immunization to enhances the production of antibodies.

In the case of FIG. 6, a diagram (ptbi-env11) is shown that demonstrates the ability to genetically engineer components of natural viruses for the production of virus particle products. In this case, the envelope gene was PCR amplified from primary cells infected with a founder/transmitted HIV-1 isolate (HIV-$1_{ITB\text{-}11}$, or TBI01280) and then cloned into a plasmid. The insert was confirmed by sequence analysis to be a full-length HIV-1 envelope gene.

In some cases, the anti-virus particle product antibodies are quantified by contacting a sample from a subject with the virus particle product, and determining the specific binding of antibodies in said sample to the virus particle product. One example includes a method of generating an immune response in a subject by administering an immunogenic amount of the virus particle product to said subject. The subject may be genetically resistant to viral infection, or the subject may be receiving anti-retroviral therapy. In some cases, the immune response includes a neutralizing response against the virus particle product.

Monoclonal antibodies can be generated from lymphocytes (for example, B lymphocytes) that have been isolated from the blood, bone marrow, or spleen of an immunized animal or human and immortalized using hybridoma and/or transformation procedures. By culturing the obtained cell derivatives, monoclonal antibodies can be obtained from the cells. In one embodiment, the antibodies are purified by methods such as DEAE anion exchange chromatography, affinity chromatography, ammonium sulfate fractionation, PEG fractionation, or ethanol fractionation. Some of the monoclonal antibodies of the present invention comprise VH and VL amino acid sequences as listed in Table 1. An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%/0, 93%, 94%, 95%, 96%, 97%, 98% or 99% identical to a portion of at least one of the amino acid sequences of Table 1, preferably to achieve maximal levels of sequence identity. Some of the monoclonal antibodies of the present invention comprise VH, VL and linker nucleic acid sequences as listed in Table 2. An oligonucleotide is within the scope of the invention if it has a nucleic acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%/o or 99% identical to a portion of at least one of the nucleic acid sequences of Table 2, preferably to achieve maximal levels of sequence identity.

In an embodiment, monoclonal antibodies are generated when an immunogenic amount of the virus particle product is administered to a subject, and a hybridoma is produced using a splenocyte isolated from said immunized subject. The hybridoma produces a monoclonal antibody that specifically binds to the virus particle product, and the monoclonal antibody is isolated. In an embodiment, said antibody is capable of neutralizing in vivo the virus particle product. Furthermore, a polyclonal antibody can be prepared that specifically binds to the virus particle product, where the antibody is capable of neutralizing in vivo the virus particle product. Immunotherapeutic methods are possible which involve administering a therapeutic amount of the aforementioned monoclonal antibody or polyclonal antibody to a subject.

Enhancing antibodies are reported for a variety of viruses and infections, including HIV, hepatitis C virus, and Ebola (Fust G. *Parasitology* 1997, 115: S127-140) (Meyer K et al., *PloS one* 2011, 6:e23699). These enhancing antibodies can be elicited in subjects and/or measured using the embodied procedures. A preferred application of the elicited or otherwise obtained enhancing antibodies is for clinical use in exposing reservoirs of HIV, where virus replication levels are too low to be detected and/or targeted by natural immune responses or clinical interventions. Another preferred application is the use of enhancing antibodies in clinical and laboratory settings where elevated levels of virus infectivity and/or replication are desired, such as for gene therapy, gene delivery using viral vectors, or maximizing the production of virus particle products.

To generate an enhancing antibody, an immunogenic amount of the virus particle product is administered to a subject. In an embodiment, said antibody is capable of activating replication in vivo of said infectious retroviral particle. Immunotherapeutic methods are possible which involve administering a therapeutic amount of the enhancing antibody to a subject. Also, a protein or protein fragment that binds to the enhancing antibody can be produced, and immunotherapeutic methods are possible which involve administering a therapeutic amount of said protein or protein fragment to a subject.

In one embodiment, an anti-virus particle product antibody is a bispecific antibody having two different antigen binding sites. The bispecific antibody binds two different epitopes. In a further embodiment, the bispecific antibody that selectively recognizes TEGS, has functional properties that differ from either of the corresponding monospecific antibodies. Further disclosure for producing bispecific antibodies is found in Rouet R and Christ D, *Nature Biotechnology* 2014, 32: 136-137; and Kontermann R, *Landes Biosciences* 2012, 4: 182-197.

A genetic sequence encoding an anti-virus particle product antibody can be obtained by producing a cDNA library using mRNA derived from immunized animals that produce TEGS-specific monoclonal antibodies as described above, and isolating a plasmid containing cDNA encoding a monoclonal antibody. In an embodiment, the mRNA from a specimen containing B cells is prepared by dissolving the cells in a guanidinium isothiocyanate solution, followed by mRNA extraction. The cDNA is produced using the extracted mRNA as a template, and the cDNA, or PCR amplified cDNA, is incorporated into vectors to produce a cDNA library. A gene encoding an anti-virus particle product monoclonal antibody is obtained using the cDNA library. Amino acid sequences of TEGS-specific antibody regions are in Table 1, and nucleic acid sequences of TEGS-specific antibody regions are in Table 2. The PCR primers used for this purpose are in Table 3.

TABLE 1

TEGS-specific antibody region amino acid sequences

| SEQ ID NO | Antibody Region and Clone Number | Amino Acid Sequence |
|---|---|---|
| SEQ ID NO: 1 | VH TBIfabT203 | QSLEESGGGLFKPTDTLTLTCTVSGFSLSNYGVVWVRQAPGNGLEW IGIIDHHGIPYYATWAKSRSTITRNTNLDTVTLKMTSLTAADTATY FCAR |
| SEQ ID NO: 2 | VL TBIfabT203 | ELVMTQTESPVSAAVGSTVTINCQASQSVYSNNNLAWFQKKPGQPP KRLIHSASTLASGVPSRFKGSGSGTQFTLTISDLECDDAATYYCAG VFSGSISVFGGGTEVVVK |
| SEQ ID NO: 3 | VH TBIfabT205 | VGEGVRGGLLKPTDTLTLTCTVSGFSLNSYAVFWVRQAPGNGLEWI GTVSSVDDTYFATWAKSRSTITRNTNLNTVTLKMTSLTAADTATYF CA |
| SEQ ID NO: 4 | VL TBFfabT205 | QPVLTQSPSVSAALGSSAKLTCTLSSAHKTYYIEWYQQQQGEAPRY LMQLESDGSYTKGTGVPDRFSGSSSGADRYLIISSVQAEDEADYYC GADYSGGFVFGGGTQLTVT |
| SEQ ID NO: 5 | VH TBIfabT206 | QSVEESGGGLFKPTDTLTLTCTVSGFSLSGYGVSWVRQAAGNGLEW IGAISSGGSAYYARWAKSRSTITRNTNLVTVTLKMTSLTAADTATY FCAR |
| SEQ ID NO: 6 | VL TBIfabT206 | ELVMTQTEPPVSAPVGGTVTINCQASQNIGSSYLSWYQQKPGQPPK LLIYQASTLASGVPSRFKGGGSGTDYSLTISGVQCADAATYYCQST FYSSGTGYAFGGGTELEIL |
| SEQ ID NO: 7 | VH TBIfabT208 | QSVKESEGGLFKPTDTLTLTCTASEFTIGSYSSGWVRQAPGKELEW IGTLSSTGSAHYANWAKGRSTITRNTNENTVTLKMASLTAADTATY FCAR |
| SEQ ID NO: 8 | VL TBIfabT208 | PVLTQSPSVSAALGASAKLTCTLSSGHKTYTIDWYQQQQGEAPRY LMQIGSDGSYTKGTGVPDRFSGSSSGTDTYLIISSVQAEDEADYYC GADYSGGFVFGGGTQLTVT |
| SEQ ID NO: 9 | VH TBIfabT209 | QSVEESGGGLFKPTDTLTLTCTVSGIDLSRNGVTWVRQAPGSGLEW IGVINSHGDSDYATWANSRSTITRNTNLNTVTLKMTSLTAADTATY FCA |
| SEQ ID NO: 10 | VL TBIfabT209 | ELVMTQTPSSVSAAVGGTVTINCQASQTINNLLAWYQQKPGQPPKL LIYGASTLASGVPSRFSGSGSGTQFILTISGMKAEDAATYYCQSAY YNAGATFGAGTNVEIK |
| SEQ ID NO: 11 | VH TBIfabT210 | QSLEESGGGLFKPTDTLTLTCTVSGFSLSNSAMSWVRQAPGNGLEW IGDIDSSGSAYYASWAKSRSTITRNTNLNTVTLKMTSLTAADTATY FCAR |
| SEQ ID NO: 12 | VL TBIfabT210 | PVLTQSPSVSAALGASAKFTCTLSSGHKTYTIDWYQQQQGEAPRY LMQIGSDGSYTKGTGVPDRFSGSSSGTDRYLIISSVQAEDEADYIC GVTGSNVYAQDPADRH |

TABLE 1-continued

TEGS-specific antibody region amino acid sequences

| SEQ ID NO | Antibody Region and Clone Number | Amino Acid Sequence |
|---|---|---|
| SEQ ID NO: 13 | VH TBIfabT216 | QSLEESGGGLFKPTDTLTLTCTVSGFDISGVYMSWVRQAPGNGLEW IGAIDRGGTYYASWAIGRSTITRNTNDNTVTLEMTSLTAADTATY FCAK |
| SEQ ID NO: 14 | VL TBIfabT216 | ELVMTQTPSSVSAAVGGTVTINCQASESISNYLAWYQQKPGQPPKL LTYDASDLASGVPSRFSGSGYGTEFTLTISGVKAEDAATYYCQSGY VSAGTFGAGTNVEIK |
| SEQ ID NO: 15 | VH TBIfabT222 | QSLEESGGGLIKPTDMLTLTCTVSGFSLSNYGVMWVRQAPGNGLES IGYIGSGGDTSYASWAKSRSTIARNTNENTVSLLMNGLTAADTATY FCAR |
| SEQ ID NO: 16 | VL TBIfabT222 | QPVLTQSPSVSAALGASAKLTCTLSSAHKTYTIDWYQQQGEAPRY LMHLKSDGTYTKGTGVPDRFSGSSSGADRYLIIPSVRTDDEADYYC GTDYSGGYVFGGGTQLTVT |
| SEQ ID NO: 17 | VH TBIfabT226 | QSLEESGGGLFKPTDTLTLTCTVSGFSLSIYGVSWVRQAPGNGLEW VGAIGSGGSAYYATWAKSRSTITRNTNLNTVTLKMASLTAADTATY FCAR |
| SEQ ID NO: 18 | VL TBIfabT226 | QPVLTQSPSASAALGSSAKLTCTLSSAHKTYYIDWYQQQGEAPRY LMQVKSDGSYTRGTGVPDRFSGSSSGADRYLIIPSVQADDEADYYC GSDYSGGYVFGGGTQLTVT |
| SEQ ID NO: 19 | VH TBIfabT229 | QSVEESRGGLFKPTDTLTLTCTVSGFSLSTYNIQWVRQAPGNGLEY IGTIGSSGSAYYARRAKSRSTITRNTALNTVSLQVDSLTDADTATY FCAR |
| SEQ ID NO: 20 | VL TBIfabT229 | ELDLTQTPSSVSAAVGGTVTINCQASQSVSNLLAWYQQKPGQPPKL LIYGASNLESGVPSRFRGSGSGTEFTLTISDVVCDDAATYYCAGHK SSSTDGTAFGGGTELEIL |
| SEQ ID NO: 21 | VH TBIfabT232 | QSVKESEGGLFKPTDTLTLTCTVSGFTVSNNAISWVRQAPGNGLEW IGAISYGGNTYYANWPKSRSTITRNTNLNTVTLKMTSLTAADTATY FCAR |
| SEQ ID NO: 22 | VL TBIfabT232 | QPVLTQSPSASAALGSSAKLTCTLSSAHKTYYIDWYQQQGEAPRY LMQVKSDGSYTKGTGVPDRFSGSSSGAGDRYLIIPSVQADDEADYY CGSDYSGGYVFGGGAQLTVT |
| SEQ ID NO: 23 | VH TBIfabT234 | QSVKESEGGLFKPTDTLTLTCTVSGFSLSNYGVSWVRQAPGKEVEW IGYINSGGSTNYASWAKSRSTITRNTNLNTVTLKMTSLTAADTATY FCAR |
| SEQ ID NO: 24 | VL TBIfabT234 | ELDMTQTPSSVSAAVDGTVTINCQASQSVTNLLAWYQQKPRQPPKL LIYDASNLESGVPSRFRGSGSGTEFTLTISGMKAEDAATYYCQSGY YSAGATFGAGTNVEIK |
| SEQ ID NO: 25 | VH TBIfabT236 | QSVKESEGGLFKPMDSMTLTCTVSGFSLSSYGVSWVRQAPGNGLEW IGAISSGGSAYYARWAKSRATITRNTNLNTVTLKMASLTAADTATY FCAR |
| SEQ ID NO: 26 | VL TBIfabT236 | ELVLTQTPSPVSAAVGGTVTINCQSSQSVYSNNRLAWYQQKPGQPP KQLIYYASTLASGVSSRFKGSGSGTQFTLTISDVVCDDAATYYCAG YKNSGIDEHAFGGGTELEIL |
| SEQ ID NO: 27 | VH TBIfabT239 | QSLEESGGGLFKPTDTLTLTCTVSGFSLNRYDMSWVRQAPGNGLEW IGVINSGGFTYYASWAKSRSTITRNTNENTVTLKMTSLTAADTATY FCAR |
| SEQ ID NO: 28 | VL TBIfabT239 | QPVLTQSPSVSAALGASAKLTCTLSSGHKTYTIDWYQQQGEAPRY LMQLGSDGSYTKQTGVPDRFSGSSSGADRYLIISSVQADDEADYYC GADYSGGFVFGGGTQLTVT |
| SEQ ID NO: 29 | VH TBIfabT240 | QSVKESEGGLFKPTDTLTLTCTVSGFSLSNNAINWVRQAPGNGLEW IGAVGSGGRAYYAGWAKSRSTITRNTNLNTVTLKMTNLTAADTATY FCAR |
| SEQ ID NO: 30 | VL TBIfabT240 | ELVLTQTPSSVSAAVGGTVSISCQSSQSVYSNYLAWYQQKPGQPPK KKIYYASTLASGVSSRFKGSGSGTQFTLTINGVQCDDAATYYCQGT FDDGLYKAFGGGTELEIL |

TABLE 1-continued

TEGS-specific antibody region amino acid sequences

| SEQ ID NO | Antibody Region and Clone Number | Amino Acid Sequence |
|---|---|---|
| SEQ ID NO: 31 | VH TBIfabT241 | QSLEESGGGLFKPTDTLTLTCTVSGFSLSNYGMGWVRQAPGNGLEYIGFISSGGNTYYASWAKSRSTITRDTNLNTVTLKMSSLTAADTATYFCAR |
| SEQ ID NO: 32 | VL TBIfabT241 | ELVMTQTPSSVSAAVGGTVTINCQASQSVYNLLAWYQQKPGQPPKLLTHGTSNLESGVPSRFRGSGSGTEFTLTISGMKAEDAATYYCQSGYYSTGATFGAGTNVEIK |
| SEQ ID NO: 33 | VH TBIfabT247 | QSLEESGGGLFKPTDPLTLTCTVSGFSINDYNMQWVRQAPGIGLEWIGAINAWGDTYYTSWAKSRSTITRDTNLNTVTLKMTSLTAADTATYFCAR |
| SEQ ID NO: 34 | VL TBIfabT247 | ELDLTQTPSSVSAAVGGTVTINCQSSQSVDSNNYLSWYQQKPGQPPKLLIYDASTLASGVPSRFSGSGSGTQFTLTISEVQCDDAATYYCQGSYYSGDWYGAFGGGTELEIL |
| SEQ ID NO: 35 | VH TBIfabT249 | QSLEESGGGLFKPTDTLTLTCTASGFTVTSNAISWVRQAPGNGLEYIGFIGAAGNANYASWAKSRSTITRNTNLNTVTLKMSSLTAADTATYFCAR |
| SEQ ID NO: 36 | VL TBIfabT249 | ELVMTQTPASVSEPVGGTVTISCQASQGVYSDRLAWYQQKPGQPPKLLMYYASDLSSGVPSRFKGSGSGTEFTLTISDLECADAATYYCQSNYGSLSSSYTFGGGTEVVVK |
| SEQ ID NO: 37 | VH TBIfabP202 | QSVEESRGGLFKPTDTLTLTCTVSGFTIDTYGVTWVRQAPGNGLEYIGFISSGGAAYYASWAKSRSTITRNTNLNTVTLKMTSLTAADTATYFCAR |
| SEQ ID NO: 38 | VL TBIfabP202 | ELVMTQTPPSLSASVGETVRIRCLASENVYSAVAWYQQKPGKPPTLLISGASNLESGVPPRFSGSGSGTDYTLTIGGVQAEDAATYFCQGYSSYLTFGAGTNVEIK |
| SEQ ID NO: 39 | VH TBIfabP210 | QSLEESGGGLIKPTDTLTLTCTVSGFSLSIYDISWVRQAPGNGLEWIGAIGSGDTTYYASWAKSRSTITRNTYLNTVTLKMTSLTAADTATYFCAR |
| SEQ ID NO: 40 | VL TBIfabP210 | QPVLTQSPSASAALRSSAKLTCTLSSAHKSYDIDWYQQQSGEAPRYLMRLRSDGKYTKGTGVPDRFSGSSSGADRYLIIPSVQADDGADYYCGTDYSGGYVFGGGTQLTVT |
| SEQ ID NO: 41 | VH TBIfabP214 | EQLVESEGGLFKPTDTLTLTCTVSGFSLNNYGVTWVRQAPGRGLEWIGAVWSGATTDYASWAKSRSTITRNTNENTVTLKMSSLTAADTATYFCA |
| SEQ ID NO: 42 | VL TBIfabP214 | ELVMTQTESPVSAAVGGTVTINCQASQSISSWLAWYQGKPGKPPTLLISGASNLESGVPPRFSGSGSGTDYTLTIGGVQAEDAATYYCLGGYSYSSIGTTFGAGTNVEIK |
| SEQ ID NO: 43 | VH TBIfabP217 | QEQLEESGGGLVQPGGSLKLSCKASGFDFINYGVIWVRQAPGKGLEWIGYIDPIFGNTIYASWVDNRFTISSHNAQNTLYLQLNSLTAADTATYFCAR |
| SEQ ID NO: 44 | VL TBIfabP217 | ELVMTQTPSSVSAAVGGTVTINCQASQSVNNLLAWYQQKPGQPPKLLTYGTSNLESGVPSRFRGSGSGTEFTLTISGMKAEDAATYYCQSGYYSAGLTFGAGTNVEIK |
| SEQ ID NO: 45 | VH TBIfabP219 | QSLEESGGGLIKPTDTLTLTCTVSGFSLSTNGVSWVRQAPGSGLEWIGAIDLYGATYYATWAKSRSTITRNTNLNTVTLKMTSLTAADTATYFCAR |
| SEQ ID NO: 46 | VL TBIfabP219 | ELVLTQTPASVSEPVGGTVTIKCQASQNIYSGISWYQQKPEKPPTLLISGASNLEPGVPPRFSGSGSGTDYTLTIGGVQAGDAATYYCLGVYSFGSTDLTFGAGTNVEIK |
| SEQ ID NO: 47 | VH TBIfabP220 | QSLEESGGGLFKPTDTLTLTCTVSGFSLSSYAISWVRQAPGNGLEWIGYINYDGIAYYASWAKSRSTITRNTNLNTVTLKMTGLTAADTATYFCAR |
| SEQ ID NO: 48 | VL TBIfabP220 | ELDLTQTPSSVSAAVGGTVSISVQSSQSVYNNYLAWYQQKPGQPPKLLIYYASKLASGVPSRFKGSGSGTQFTLTISDVQCDDAATYYCQGTFDNGLYKAFGGGTELEIL |

TABLE 1-continued

TEGS-specific antibody region amino acid sequences

| SEQ ID NO | Antibody Region and Clone Number | Amino Acid Sequence |
|---|---|---|
| SEQ ID NO: 49 | VH TBIfabP221 | QSLEESGGGLVQPGGSLKLSCKGSGFDLDSNAMCWVRQAPGSGLEW IGTITSDDSAYYASWAKSRSTITRNTNLNTVTLKMTSLTAADTATY FCAR |
| SEQ ID NO: 50 | VL TBIfabP221 | ELDMTQTPSSVSAAVGGTVTINCQASESINLLAWYQQKPGQPPKLL IYSASTLASGVPSRFRGSGSGTEFTLTISGMKAEDAATYYCQSGYY STGATFGAGTNVEIK |
| SEQ ID NO: 51 | VH TBIfabT7 | QEQLEESGGRLVKPDETLTLTCTVSGLSLNNFGVSWVRQAPGNGLE WIRAIDFGSGSAYYANWAKSRSTITSNTRLNTVTLKMISLTAADTA TYFCSR |
| SEQ ID NO: 52 | VL TBIfabT7 | QPVLTQSPSVSAALGASAKLTCTLSSAHKTYTIDWYQQQSGEAPRY LMQLKSDGNYTKGTGVPDRFSGSSSGADTYLIIPSVQADDEADYYC GADYSGGYVFGGGTQLTVT |
| SEQ ID NO: 53 | VH TBIfabT14 | QSVKESEGGLFKPTDTLTLTCTVSGFSLSNYAINWVRQAPGEGLEW IGYIDPTFGSTYYASWVDNRFTISSHNAQNTLYLQLNSLTPADTAT YFCAR |
| SEQ ID NO: 54 | VL TBIfabT14 | ELDMTQTPSSVSAAVGGTVTISCQASQSVYNNNNLSWYQQKPGQPP KLLIYDASKLASGVPSRFKGSGSGTQFTLTISDLECDNAATYYCQQ GYDGSDVDNVFGGGTEVVVK |
| SEQ ID NO: 55 | VH TBIfabP9 | QSLEESGGGLFKPGGSLTLTCTVSGFTITSYHMCWVRQAPGNGLGW IGAVSASGHTYYANWAKSRSTITRDTNLNTMTLKMTSLTAADTATY FCA |
| SEQ ID NO: 56 | VL TBIfabP9 | ELVLTQTPPSLSASVGETVRIRCLASEFLFNASVSWYQQKPEKPPT LPIYGASNLESGVPPRFSGSGSGTQFTLTISDLECDDAATYYCAGD YSDWIYAFGGGTEVVVK |
| SEQ ID NO: 57 | VH TIBfabP12 | QSLEESGGGLFKPTDTLTLTCTVSGFSLSSYGITWVRQAPGNGLEW IGAIGSDAKTYYASWAKGRSTITGDTNLNTVTLRMTSLTAADTATY FCAR |
| SEQ ID NO: 58 | VL TBIfabP12 | ELVLTQTPSSVPAAVGGTVTIDCQSSESVYNNNNLAWYQQKPGQPP KLLIYGASTLASGVSSRFKGSGSGTEFTLTISDLECADAATYYCQQ GYSIGNVDNAFGGGTELEIL |
| SEQ ID NO: 59 | VH TBIfabP18 | QSVKESEGGLFKPTDTLTLTCTVSGFSLSSYGVSWVRQAPGNGLEW IGAISSGGDAYYASWATSRSTITRNTNLNTVTLKMTSLTAADTATY FCAR |
| SEQ ID NO: 60 | VL TBIfabP18 | ELVMTQTPASVEVAVGGTVTIKCQASQSISSYLAWYQQKPGQPPKL LIYKASTLASGVPSRFKGSGSGTQFTLTISDVVCDDAATYYCAGYK GGSSDGSAFGGGTELEIL |
| SEQ ID NO: 61 | VH TBIfabP19 | QSVEESGGGLFKPADTLTLTCTVSGFSLSYPGVSWVRQAPGNGLEY IGFINADGDSYYPTWAKRRSTITRNTNLNTVTLKMTSLTAADTATY FCA |
| SEQ ID NO: 62 | VL TBIfabP19 | QPVLTQSPSASAALGSSAKLTCTLSSAHKTYYIEWYQQQQGEAPRY LMQVKSDGSYTKGTGVPDRFSGSSSGADRYLIIPSVQADDEADYYC GADYSGGYVLGGGTQLTVT |
| SEQ ID NO: 63 | VH TBIfabT114 | QSLEESGGGLFKPADTLTLACTVSGFSLSTYGVIWVRQAPGKGLEY IAYINYSGSPYYASWAKSRSTITRNTNEKTVTLKMTSLTAADTATY FCAR |
| SEQ ID NO: 64 | VL TBIfabT114 | QPVLTQSPSASAALGSSAKLTCTLSSAHKTYYIDWYQQQQGEAPRY LMQLGSDGSYTKGTGVPDRFSGSSSGADRYLIIPSVQADDESDYYC GSDYSGGYVFGGGTQLTVT |
| SEQ ID NO: 65 | VH TBIfabT116 | SRWRSPGGGLFKPTDTLTLTCTVSGFSLSGYGVSWVRQAPGNGLEW IGAISSGGSAYYARWAKSRSTITRNTNLNTVTLKMTSLTAADTATY FCAR |
| SEQ ID NO: 66 | VL TBIfabT116 | QPVLTQSPSVSAALGASAKLTCTLSSAHKTYTIDWYQQQGEAPRY LMQLKSDGSYTKGTGVPDRFSGSSSGADRYLIIPSVQADDEADYYC GADYSGGYVFGGGTQLTVT |

TABLE 1-continued

TEGS-specific antibody region amino acid sequences

| SEQ ID NO | Antibody Region and Clone Number | Amino Acid Sequence |
|---|---|---|
| SEQ ID NO: 67 | VH TBIfabT124 | QSVKESEGGLFKPTDTLTLTCTVSGFSLSNYGVSWVRQAPGNGLEY IGFISNGGATFYATWARSRATITRNTGLNTVALTMTSLTAADTATY FCVR |
| SEQ ID NO: 68 | VL TBIfabT124 | ELDMTQTPPSLSASVGETVRIRCLASEDIGSAISWYQQKPGKPPTL LIYGVFNLESGVPPRFSGSGSGTDYTLTIGGVQAEDAATYYCLGGA SDSSTGLTFGAGTNVEIK |
| SEQ ID NO: 69 | VH TBIfabT129 | QSVKESEGGLFKPTDTQTLTCTVSGFSLSSNAISWVRQAPGNGLKS IGFINSGGGAYYATWAKSRSTITRNTNENTVTLKMTSLTAADTATY FCAR |
| SEQ ID NO: 70 | VL TBIfabT129 | QPVLTQSPSLSASLGTTARLTCTLSTGYSVGEYPLVWLQQVPGRPP RYLLSFTSDEDKHHDSWGPTRFSGSKDTSENTFILSISGLQPEDEA DYYCATAHGSDNSLHYVFGGRTQLTVT |
| SEQ ID NO: 71 | V5 TBIfabT134 | QSLEESGGGLFKPTDTLTLTCTVSGFALNNYNIHWVRQAPGNGLEW IGAIGSSGSAYYASWAKSRSTITRNTNLNTVTLKMTSLTAADTATY FCAR |
| SEQ ID NO: 72 | VL TBIfabT134 | QPVLTQSPSASAALGSSAKLTCTLSSAHKTYYIEWYQQQGEAPRY LIQLKSDGSYTKGTGVPDRFSGSSSGTDRYLIISSVQAEDEADYSC GADYSGGFVFGGGTQLTVT |
| SEQ ID NO: 73 | VH TBIfabP212 | VGGGVQGGGLVKPGDTLTLTCTVSGFPLSSYDMNWVRQAPGEGLEW IGWITYDGYNHYASWANGRSTITRNTNENAVTLKMTSLTAADTATY FCAR |
| SEQ ID NO: 74 | VL TBIfabP212 | ELVLTQTPPSLSASVGGTVTINCLASENVYSAVAWYQQKPGKPPTL LISGTSNLEAGVPPRFSGSGSGTDYTLTIGGVQAEDAATYFCQGYS SYPLTLFAGTNVEIK |

TABLE 2

TEGS-specific antibody region nucleic acid sequences

| SEQ ID NO | Clone Number | Nucleic Acid Sequence (VL-linker-VH; linker underlined) |
|---|---|---|
| SEQ ID NO: 75 | TBIfabT203 | CCCAGCCGGCCATGGCTGAGCTCGTGATGACCCAGACTGAATCGCCCGTGTCTG CAGCTGTGGGAAGCACAGTCACCATCAATTGCCAGGCCAGTCAGAGTGTTTATA GTAACAACAACTTAGCCTGGTTTCAGAAGAAACAGGGCAGCCTCCCAAGCGCC TGATCCATTCTGCATCCACTCTGGCATCTGGGGTCCCATCGCGGTTCAAAGGCA GTGGATCTGGGACACAGTTCACTCTCACCATCAGCGACCTGGAGTGTGACGATG CTGCCACTTACTACTGTGCAGGCGTTTTTAGTGGTAGTATTAGTGTTTTCGGCG GAGGGACCGAGGTGGTCGTCAAGGTGGTTCCTCTAGATCTTCCTCCTCTGGTGG CGGTGGCTCGGGCGGTGGTGGGCAGTCGCTGGAGGAGTCCGGGGGAGGTCTCTT CAAGCCAACGGATACCCTGACACTCACCTGCACAGTCTCTGGATTCTCCCTCAG TAACTATGGAGTGGTCTGGGTCCGCCAGGCTCCAGGGAACGGGCTGGAATGGAT CGGAATCATTGATCATCATGGTATCCCATACTACGCAACCTGGGCGAAAAGCCG ATCCACCATCACCAGAAACACCAACCTGGACACGGTGACTCTGAAAATGACCAG TCTGACAGCCGCGGACACGGCCACCTATTTCTGTGCGAGAGCTTACGTTAATTT TGGCTGGGATTATGCTCTTAACATCTGGGGTCCAGGCACCCTGGTCACCGTCTC CTCAGGGCAACCTAAGGCTCCGTCAGTCACTAGTGGCCCCGGGAGGCCA |
| SEQ ID NO: 76 | TBIfabT205 | CCGGCCATGGCTCAGCCTGTGCTGACTCAGTCGCCCTCTGTGTCTGCTGCCCTG GGATCCTCGGCCAAGCTCACCTGCACTCTGAGCAGTGCTCACAAGACCTACTAT ATTGAATGGTATCAGCAACAACAAGGGGAGGCCCCTCGGTACCTGATGCAACTT GAGAGTGATGGAAGCTACACCAAGGGGACCGGGGTCCCTGATCGCTTCTCGGGC TCCAGCTCTGGGGCTGACCGCTACTTGATCATCTCCAGCGTCCAGGCTGAGGAC GAAGCCGACTACTATTGTGGTGCAGATTATAGTGGTGGGTTTGTGTTCGGCGGA GGGACCCAGCTGACCGTCACAGGTGGTGTTCCTCTAGATCTTCCTCCTCTGGT GGCGGTGGCTCGGGCGGTGGTGGGCAGTCGGTGAAGGAGTCCGGGGAGGTCTCC TCAAGCCAACGGATACCCTGACACTCACCTGCACAGTCTCTGGATTCTCCCTCA ATAGCTATGCAGTATTCTGGGTCCGCCAGGCTCCAGGGAACGGGCTGGAATGGA TCGGAACCGTTAGTAGTGTTGGTGACACATACTTCGCACCTGGGCGAAAGCC GATCCACCATCACCAGAAACACCAACCTGAACACGGTGACTCTGAAAATGACCA GTCTGACAGCCGCGGACACGGCCACCTATTTTTGTGCGAGGGGGGTTGGTGTTA GTTATTATCTTGATGCTTTTGATTCTTGGGGCCCAGGCACCCTGGTCACCGTCT CCTCAGGGCAACCAGGCTCCATCAGTCACTAGTGGCCCGGGAGGCCA |

TABLE 2-continued

TEGS-specific antibody region nucleic acid sequences

| SEQ ID NO | Clone Number | Nucleic Acid Sequence (VL-linker-VH; linker underlined) |
|---|---|---|
| SEQ ID NO: 77 | TBTfabT206 | CCGGCCATGGCTGAGCTCGTGATGACCCAGACTGAACCCCCCGTGTCTGCACCT GTGGGAGGCACAGTCACCATCAATTGCCAGGCCAGTCAGAACATTGGTAGTAGC TACTTATCCTGGTATCAGCAGAAACCAGGGCAGCCTCCCAAGCTCCTGATCTAC CAGGCTTCCACTCTGGCATCTGGGGTCCCATCGCGGTTCAAAGGCGGTGGATCT GGGACAGACTACAGTCTCACCATCAGCGGCGTGCAGTGTGCCGATGCCGCCACT TATTACTGTCAAAGTACTTTTTATAGTAGTGGTACTGGTTATGCTTTCGGCGGA GGGACCGAGCTGGAGATCCT<u>GGTGGTTCCTCTAGATCTTCCTCCTCTGGTGGCG GTGGCTCGGGCGGTGGTGGG</u>CAGTCGGTGGAGGAGTCCGGGGGAGGTCTCTTCA AGCCAACGGATACCCTGACACTCACCTGCACAGTCTCTGGATTCTCCCTCAGTG GCTATGGAGTGAGCTGGGTCCGCCAGGCTGCAGGGAACGGGCTGGAATGGATCG GAGCCATTAGTAGTGGTGGTAGCGCATACTACGCGAGATGGGCGAAAAGCCGAT CCACCATCACCAGAAACACCAACCTGAACACGGTGACTCTGAAAATGACCAGTC TGACAGCCGCGGACACGGCCACCTATTTCTGTGCGAGAGGTTACTATACTGCTA TTGGTGGTACTTATGACAATGCTTTTGATCCCTGGGGCCCAGGCACCCTGGTCA CCGTCTCCTCAGGGCAACCTAAGGCCATCAGTCACTAGTGGCCCGGGAGGCCA |
| SEQ ID NO: 78 | TBIfabT208 | GGCCCAGCCGGCCATGGCTCAGCCTGTGCTGACTCAGTCGCCCTCTGTGTCTGC CGCCCTGGGAGCCTCTGCCAAGCTCACCTGCACCCTGAGCAGTGGCCACAAGAC CTACACCATTGACTGGTATCAGCAGCAGCAGCAAGGGGAGGCCCCTCGGTACCT GATGCAGATTGGGAGTGATGGAAGCTACACCAAGGGGACCGGGGTCCCTGATCG CTTCTCGGGCTCCAGCTCTGGGACTGACCGCTACTTGATCATCTCCAGCGTCCA GGCTGAGGACGAAGCCGACTACTATTGTGGTGCAGATTATAGTGGTGGGTTTGT GTTCGGCGGAGGGACCCAGCTGACCGTCACAGGT<u>GGTGGTTCCTCTAGATCTTC CTCCTCTGGTGGCGGTGGCTCGGGCGGTGGTGGG</u>CAGTCGGTGAAGGAGTCCGA GGGAGGTCTCTTCAAGCCAACGGATACCCTGACACTCACCTGCACAGCCTCCGA ATTCACCATCGGTAGTTATAGTAGTGGCTGGGTCCGCCAGGCTCCAGGGAAGGA GCTGGAGTGGATCGGAACCCTTAGTTCTACTGGTAGCGCACACTACGCGAACTG GGCGAAAGGCCGTTCCACCATCACCAGAAACACCAACGAGAACACGGTGACTCT GAAGATGGCCAGTCTGACAGCCGCGGACACGGCCACCTATTTCTGTGCGAGAGC TGATTATGGGCCCTGTTATTTTGACATCTGGGGCCCAGGCACCCTGGNCACCGT TTTCTCNGGNAACCTNANNCTCCATCAGTCACTAGTGGCCCGGGAGGCCA |
| SEQ ID NO: 79 | TBIfabT209 | CCGGCCATGGCTGAGCTCGTGATGACCCAGACTCCATCCTCTGTGTCTGCAGCT GTGGGAGGCACAGTCACCATCAATTGCCAGGCCAGTCAGACTATTAACAACCTC TTAGCCTGGTATCAGCAGAAACCAGGGCAGCCTCCCAAGCTCCTGATTTATGGT GCATCCACTCTGGCATCTGGGGTCCCATCGCGTTTCAGCGGCAGTGGATCTGGG ACACAGTTCATTCTCACCATCAGTGGCATGAAGGCTGAAGATGCTGCCACTTAT TACTGTCAAAGTGCTTATTATAATGCTGGTGCGACTTTTGGAGCTGGCACCAAT GTGGAAATCAAG<u>GTGGTTCCTCTAGATCTTCCTCCTCTGGTGGCGGTGGCTCGG GCGGTGGTGGG</u>CAGTCGGTGGAGGAGTCCGGGGGAGGTCTCTTCAAGCCAACGG ATACCCTGACACTCACCTGCACAGTCTCTGGAATCGACCTCAGTAGAAATGGAG TGACCTGGGTCCGCCAGGCTCCAGGGAGCGGGCTGGAATGGATCGGAGTCATTA ATAGTCATGGTGACAGTGATTACGCGACCTGGGCGAACAGCCGATCCACCATCA CCAGAAACACCAACCTGAACACGGTGACTCTGAAAATGACCAGTCTGACAGCCG CGGACACGGCCACCTATTTCTGTGCGAGTACTTATGATAGTTATTATGATTATG CTTGGCCTAATTTTGGCATCTGGGGCCCAGGCACCCTGGTCACCGTCTCCTCAG GGCAACCTAAGGCCAGTCACTAGTGGCCCGGGAGGCCA |
| SEQ ID NO: 80 | TBIfabT210 | GGCCCAGCCGGCCATGGCTCAGCCTGTGCTGACTCAGTCGCCCTCTGTGTCTGC CGCCCTGGGAGCCTCTGCCAAGTTCACCTGCACCCTGAGCAGTGGCCACAAGAC CTACACCATTGACTGGTATCAGCAGCAGCAGCAAGGGGAGGCCCCTCGGTACCT GATGCAGATTGGGAGTGATGGAAGCTACACCAAGGGGACCGGGGTCCCTGATCG CTTCTCGGGCTCCAGCTCTGGGACTGACCGCTACTTGATCATCTCCAGCGTCCA GGCTGAGGACGAAGCTGACTACATCTGTGGTGTAACTGGTAGTAATGTTTATGC ACAGGACCCAGCTGACCGTCACAGGT<u>GGTGGTTCCTCTAGATCTTCCCCTGGTG GCGGTGGCCGGGCGGTGGTGGG</u>CAGTCGCTGGAGGAGTCCGGGGGAGGTCTCTT CAAGCCAACGGATACCCTGACACTCACCTGCACAGTCTCTGGATTCTCCCTCAG TAACAGTGCAATGAGCTGGGTCCGCCAGGCTCCAGGGAACGGGCTGGAATGGAT CGGAGACATTGATAGTAGTGGTAGCGCATACTACGCGAGCTGGGCGAAAAGCCG ATCCACCATCACCAGAAACACCAACCTGAACACGGTGACTCTGAAAATGACCAG TCTGACAGCCGCGGACACGGCCACCTATTTCTGTGCGAGAGGGGGTTATGGTAA AATGCTGGTACTCCTTACTATGGCATGACCTCTGGGGCCCAGGGACCCTCGTC ACCGTCTCCTCAGGGCAACCTAAGGCTCCATCAGTCACTAGTGGCCCGGGAGGC CA |
| SEQ ID NO: 81 | TBIfabT216 | CCGGCCATGGCTGAGCTCGTGATGACCCAGACTCCATCCTCTGTGTCTGCAGCT GTGGGAGGCACAGTCACCATCAATTGCCAGGCCAGTGAAAGCATTAGCAACTAC TTAGCCTGGTATCAGCAGAAACCAGGGCAGCCTCCCAAGCTCCTGACCTATGAT GCATCTGATCTGGCATCTGGGGTCCCATCGCGGTTCAGCGGCAGTGGATATGGG ACAGAGTTCACTCTCACCATTAGTGGCGTGAAGGCTGAAGATGCTGCCACTTAT TATTGTCAAAGTGGTTATGTTAGTGCTGGGACTTTTGGAGCTGGCACCAATGTG GAAATCAAG<u>GTGGTTCCTCTAGATCTTCCTCCTCTGGTGGGCGGTGGTGGGCA GTCGTTGGAGGAGTCCGGGGGAGGTCTCTTCAAGCCAACGGATACCCTGACACT CACCTGCACAGTCTCTGGATTCGACATTAGTGGCGTTTACATGAGCTGGGTCCG CCAGGCTCCAGGGAACGGGCTGGAGTGGATCGGAGCCATTGATCGTGGTGGTGG |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | CACTTACTACGCGAGCTGGGCGATAGGCCGATCCACCATCACCAGAAACACCAA<br>CGACAACACGGTGACTCTGGAAATGACCAGTCTGACAGCCGCGGACACGGCCAC<br>CTATTTCTGTGCGAAAGGATATAGTGTTCTTGATCCCTGGGGCCCAGGCACCCT<br>GGNCACCGTCTCCTCAGGGCAACCTAAGGCTCCATCAGTCACTAGTGGCCCGGG<br>AGGCCA |
| SEQ ID NO: 82 | TBIfabT222 | GGCCCAGCCGGCCATGGCTCAGCCTGTGCTGACTCAGTCGCCCTCTGTGTCTGC<br>CGCCCTGGGAGCCTCTGCCAAGCTCACCTGCACCCTGAGCAGTGCCCACAAGAC<br>CTACACCATTGACTGGTATCAGCAGCAGCAAGGGGAGGCCCCTCGATACCTGAT<br>GCATCTTAAGAGTGATGGAACCTACACCAAGGGGACCGGGGTCCCTGATCGCTT<br>CTCGGGCTCCAGCTCTGGGGCTGACCGCTACTTGATCATCCCCAGCGTCCGAAC<br>TGATGACGAAGCCGACTACTATTGTGTACAGATTACAGCGGTGGGTATGTATT<br>CGGCGGAGGGACCCAGCTGACCGTCACAGGT<u>GGTGGTTCCTCTAGATCTTCCTC<br>CTCTGGTGGCGGTGGCTCGGGCGGTGGTGGG</u>CAGTCGCTGGAGGAGTCCGGGGG<br>AGGCCTGATCAAGCCAACGGATATGTTGACACTCACCTGCACAGTCTCTGGATT<br>CTCCCTCAGTAACTATGGAGTGATGTGGGTCCGCCAGGCTCCAGGGAACGGACT<br>GGAGTCGATCGGATATATTGGTAGTGGTGGTGACACATCCTACGCGAGCTGGGC<br>GAAAAGCCGATCCACCATCGCCAGAAACACCAACGAGAACACGGTGTCTCTGCT<br>CATGAATGGTCTGACAGCCGCGGACACGGCCACCTATTTCTGTGCGAGAGATCC<br>TGGTTATAGTGCTGGTAGTGCTTTTGATCCCTGGGGCCCAGGCACCCTGGTCAC<br>CGTCTTCTCAGGGCAACCTAAGGCTCCATCAGTCACTAGTGGCCCGGGAGGCCA |
| SEQ ID NO: 83 | TBIfabT226 | GGCCCAGCCGGCCATGGCTCAGCCTGTGCTGACTCAGTCGCCCTCTGCATCTGC<br>TGCCCTGGGATCCTCGGCCAAGCTCACCTGCACTCTGAGCAGTGCTCACAAGAC<br>CTACTATATTGACTGGTATCAGCAGCAGCAAGGGGAGGCCCCTCGGTACCTGAT<br>GCAGGTTAAGAGTGATGGAAGCTACACCAGGGGGACCGGGGTCCCTGATCGCTT<br>CTCGGGCTCCAGCTCTGGGGCTGACCGCTACTTGATCATCCCCAGCGTCCAGGC<br>TGATGACGAAGCCGACTACTATTGTGTTCAGATTATAGCGGTGGGTATGTGTT<br>CGGCGGAGGGACCCAGCTGACCGTCACAGGT<u>GGTGGTTCCTCTAGATCTTCCTC<br>CTCTGGTGGCGGTGGCTCGGGCGGTGGTGGG</u>CAGTCGTTGGAGGAGTCCGGGGG<br>AGGTCTCTTCAAGCCAACGGATACCCTGACACTCACCTGCACAGTCTCTGGATT<br>CTCCCTCAGTATCTATGGAGTGAGCTGGGTCCGCCAGGCTCCGGGGAATGGGCT<br>GGAATGGGTCGGAGCCATTGGTAGTGGTGGTAGCGCATACTACGCGACCTGGGC<br>GAAAAGCCGATCCACCATCACCAGAAACACCAACCTGAACACGGTGACTCTGAA<br>AATGGCCAGTCTGACAGCCGCGGACACGGCCACCTATTTCTGTGCGAGAGGTTA<br>CTATACTGCTATTGGTGGTACTTATGACAATGCTTTTGATCCCTGGGGCCCAGG<br>CACCCTGGTCACCGTCTCCTCAGGGCAACCTAAGTCCATCAGTCACTAGTGGCC<br>CGGGAGGCCA |
| SEQ ID NO: 84 | TBIfabT229 | CCGGCCATGGCTGAGCTCGATCTGACCCAGACTCCATCCTCTGTGTCTGCAGCT<br>GTGGGAGGCACAGTCACCATCAATTGCCAGGCCAGTCAGAGTGTTAGCAACCTC<br>TTAGCCTGGTATCAGCAGAAACCAGGGCAGCCTCCCAAGCTCCTGATTTATGGT<br>GCATCCAATCTGGAATCTGGGGTCCCATCGCGTTTCCGTGGCAGTGGATCTGGG<br>ACAGAGTTCACTCTCACCATCAGCGATGTGGTGTGTGACGATGCTGCCACTTAC<br>TACTGTGCAGGACATAAAAGTAGTAGTACTGATGGTACTGCTTTCGGCGGAGGG<br>ACCGAGCTGGAGATCCT<u>GGTGGTTCCTCTAGATCTTCCTCCTCTGGTGGCGGTG<br>GCTCGGGCGGTGGTGGG</u>CAGTCGGTGGAGGAGTCCAGGGGAGGTCTCTTCAAGC<br>CAACGGATACCCTGACACTCACCTGTACAGTCTCTGGATTCTCCCTTAGTACCT<br>ACAACATACAATGGGTCCGCCAGGCTCCAGGGAACGGGCTGGAATATATCGGAA<br>CCATTGGTAGTAGTGGTAGCGCATACTACGCGAGCCGGGCGAAAAGCCGATCCA<br>CCATCACCAGAAACACCGCCCTGAACACGGTGTCTCTGCAAGTGGACAGTCTGA<br>CAGACGCGGACACGGCCACCTATTTCTGTGCGAGAGGAGGGACTTGGTATACAG<br>ATGGTCTTGCTTATGTTGATGCTTTTGATCTCTGGGGCCCAGGCACCCTGGNCA<br>CCGCCTNCTCNGGCAACCTAGTCACTAGTGGNCCGGGAGGCCA |
| SEQ ID NO: 85 | TBIfabT232 | GGCCCAGCCGGCCATGGCTCAGCCTGTGCTGACTCAGTCGCCCTCTGCATCTGC<br>TGCCCTGGGATCCTCGGCCAAGCTCACCTGCACTCTGAGCAGTGCTCACAAGAC<br>CTACTATATTGACTGGTATCAGCAGCAGCAAGGGGAGGCCCCTCGGTATCTGAT<br>GCAGGTTAAGAGTGATGGAAGCTACACCAAGGGGACCGGGGTCCCTGATCGCTT<br>CTCGGGCTCCAGCTCTGGGGCTGACCGCTACTTGATCATCCCCAGCGTCCAGGC<br>TGATGACGAAGCCGACTACTATTGTGTTCAGATTATAGCGGTGGGTATGTGTT<br>CGGCGGAGGGGCCCAGCTGACCGTCACAGGT<u>GGTGGTTCCTCTAGATCTTCCTC<br>CTCTGGTGGCGGTGGCTCGGGCGGTGGTGGG</u>CAGTCGGTGAAGGAGTCCGAGGG<br>AGGTCTCTTCAAGCCAACGGATACCCTGACACTCACCTGCACAGTCTCTGGATT<br>CACCGTCAGTAACAATGCAATAAGCTGGGTCCGCCAGGCTCCAGGGAATGGGCT<br>GGAATGGATCGGAGCCATTAGTTACGGTGGTAACACATACTACGCGAACTGGCC<br>GAAAAGCCGATCCACCATCACCAGAAACACCAACCTGAACACGGTGACTCTGAA<br>AATGACCAGTCTGACAGCCGCGGACACGGCCACCTATTTCTGTGCGAGATTCTA<br>CTATGGTGCTGGTTATGCCTATGACATCTGGGGCCCAGGCACCCTGGTCACCGT<br>CTTCTCAGGGCAACCTAAGGCTCCGTCAGTCACTAGTGGCCCGGGAGGCCA |
| SEQ ID NO: 86 | TBIfabT234 | CCGGCCATGGCTGAGCTCGATATGACCCAGACTCCATCCTCTGTGTCTGCAGCT<br>GTGGGAGACACAGTCACCATCAATTGTCAGGCCAGTCAGAGTGTTACCAACCTC<br>TTAGCCTGGTATCAGCAGAAACCAAGGCAGCCTCCCAAACTCCTGATTTATGAT<br>GCATCCAATCTAGAATCTGGAGTCCCATCGCGTTTCCGTGGCAGTGGATCTGGG |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | ACAGAGTTCACTCTCACCATCAGTGGCATGAAGGCTGAAGATGCTGCCACTTAT<br>TACTGTCAAAGTGGTTATTATAGTGCTGGTGCGACTTTTGGAGCTGGCACCAAT<br>GTGGAAATCAAG<u>GTGGTTCCTCTAGATCTTCCTCCTCTGGTGGCGGTGGCTCGG</u><br><u>GCGGTGGTGGG</u>CAGTCGGTGAAGGAGTCCGAGGGAGGTCTCTTCAAGCCAACGG<br>ATACCCTGACACTCACCTGCACAGTCTCTGGATTCTCCCTCAGTAACTATGGAG<br>TGAGCTGGGTCCGCCAGGCTCCAGGGAAGGAGGTGGAGTGGATCGGATACATTA<br>ACAGTGGTGGTAGTACTAATTACGCGAGCTGGGCGAAAAGCCGATCCACCATCA<br>CCAGAAACACCAATTTGAACACGGTGACTCTGAAAATGACCAGCCTGACAGCCG<br>CGGACACGGCCACCTATTTCTGTGCGAGAGGTTACCGTGGTTATAATGTTGGTA<br>TGGATGCTTTTGATGTCTGGGGCCCANGCAATCTGGTCACCGTCTCCTCAGGNA<br>ACCTANNCTCTCAGTCACTAGTGGCCCGGGAGGCCA |
| SEQ ID NO: 87 | TBIfabT236 | CCGGCCATGGCTGAGCTCGTGCTGACCCAGACTCCATCCCCAGTGTCTGCGGCT<br>GTTGGAGGCACAGTCACCATCAATTGCCAGTCCAGTCAGAGTGTTTATAGTAAC<br>AACCGCTTAGCCTGGTATCAGCAGAAACCAGGGCAGCCTCCCAAGCAACTGATC<br>TATTATGCATCCACTCTGGCATCTGGGGTCTCATCGCGGTTCAAAGGCAGTGGA<br>TCTGGGACACAGTTCACTCTCACCATCAGCGATGGTGTGTGACGATGCTGCC<br>ACTTACTACTGTGCAGGATATAAAAATAGTGGTATTGATGAACATGCTTTCGGC<br>GGAGGGACCGAGCTGGAGATCCT<u>GGTGGTTCCTCTAGACTTCTCCTCTGGTGGC</u><br><u>GGTGGCTCGGGCGGTGGTGGG</u>CAGTCGGTGAAGGAGTCCGAGGGAGGTCTCTTC<br>AAGCCAATGGATAGCATGACACTCACCTGCACAGTCTCTGGATTCTCCCTCAGT<br>AGCTATGGAGTGAGCTGGGTCCGCCAGGCTCCAGGGAACGGGCTGGAATGGATC<br>GGAGCCATTAGTAGTGGTGGTAGCGCATACTACGCGAGATGGGCGAAAAGCCGA<br>GCCACCATCACCAGAAACACCAACCTGAACACGGTGACTCTGAAAATGGCCAGT<br>CTGACAGCCGCGGACACGGCCACCTATTTCTGTGCGAGAGGTTACTATACTGCT<br>ATTGGTGGTACTTATGACAATGCTTTTGATCCCTGGGGCCCAGGCACCCTGGTC<br>ACCGTCTCCTCAGGGCAACCTAACAGTCACTAGTGGCCCGGGAGGCCA |
| SEQ ID NO: 88 | TBIfabT239 | GGCCCAGCCGGCCATGGCTCAGCCTGTGCTGACTCAGTCGCCCTCTGTGTCTGC<br>CGCCCTGGGAGCCTCTGCCAAGCTCACCTGCACCCTGAGCAGTGGCCACAAGAC<br>CTACACCATTGACTGGTATCAGCAGCAGCAAGGGGAGGCCCCTCGGTACCTGAT<br>GCAGCTTGGGAGTGATGGAAGCTACACCAAGCAGACCGGGGTCCCTGATCGCTT<br>CTCGGGCTCCAGCTCTGGGGCTGACCGCTACTTGATCATCTCCAGCGTCCAGGC<br>TGATGACGAAGCCGACTACTATTGTGGTGCGGATTATAGTGGTGGGTTTGTGTT<br>CGGCGGAGGGACCCAGCTGACCGTCACAGGT<u>GGTGGCCTCTAGATCTTCCTCCT</u><br><u>CTGGTGGCGGTGGCTCGGGCGGTGGTGGG</u>CAGTCGTTGGAGGAGTCCGGGGGAG<br>GTCTCTTCAAGCCAACGGATACCCTGACACTCACCTGCACAGTCTCTGGATTCT<br>CCCTCAACAGGTACGACATGAGTTGGGTCCGCCAGGCTCCAGGGAACGGGCTGG<br>AATGGATCGGAGTCATTAATAGTGGTGGGTTCACATACTACGCGAGCTGGGCGA<br>AAAGCCGATCCACCATCACCAGAAACACCAACGAGAACACGGTGACTCTGAAAA<br>TGACCAGTCTGACAGCCGCGGACACGGCCACCTATTTCTGTGCGAGAGGTTACC<br>GTGGTTATAATGTTGGTATGGATGCTTTTGATGTCTGGGGCCCAGGCAATCTGG<br>TCACCGTCTCCTCAGGGCAACCTAAGTCCGTCAGTCACTAGTGGCCCGGGAGGC<br>CA |
| SEQ ID NO: 89 | TBIfabT240 | GGCCCAGCCGGCCATGGCTGAGCTCGTGCTGACCCAGACTCCATCGTCCGTGTC<br>TGCAGCTGTGGGAGGCACAGTCAGCATCAGTTGCCAGTCCAGTCAGAGTGTTTA<br>TAGTAACTACTTAGCCTGGTATCAGCAGAAACCAGGGCAGCCTCCCAAGCTCCT<br>GATCTATTATGCATCCACTCTGGCATCTGGGGTCTCATCGCGGTTCAAAGGCAG<br>TGGATCTGGGACACAGTTCACTCTCACCATCAACGGCGTGCAGTGTGACGATGC<br>TGCCACTTACTACTGTCAAGGCACTTTTGATGATGGTTTGTACAAGGCTTTCGG<br>CGGAGGGACCGAGCTGGAGATCC<u>TGGTGGTTCCTCTAGATCTTCCTCCTCTGGT</u><br><u>GGCGGTGGCTCGGGCGGTGGTGGG</u>CAGTCGGTGAAGGAGTCCGAGGGAGGTCTCTT<br>TCAAGCCAACGGATACCCTGACACTCACCTGCACAGTCTCTGGATTCTCCCTCA<br>GTAACAATGCAATAAACTGGGTCCGCCAGGCTCCAGGGAACGGGCTGGAGTGGA<br>TCGGAGCCGTTGGTAGTGGTGGTAGGGCATACTACGCGGGCTGGGCGAAAAGCC<br>GATCCACCATCACCAGAAACACCAACCTGAACACGGTGACTCTGAAAATGACGA<br>ATCTGACAGCCGCGGACACGGCCACCTATTTCTGTGCGAGAGTCGGATTTTACT<br>ATGGCAATGGTCTTTCTTATGGTATTGGCGCTTTTGATCCCTGGGGCCCAGGCA<br>CCCTGGTCACCGTCTCCTCAGGGCAACCAGGCTCCGTCAGTCACTAGTGGCCCG<br>GGAGGCCA |
| SEQ ID NO: 90 | TBIfabT241 | CCGGCCATGGCTGAGCTCGTGATGACCCAGACTCCATCCTCTGTGTCTGCAGCT<br>GTGGGAGGCACAGTCACCATCAATTGCCAGGCCAGTCAGAGTGTTTACAACCTC<br>TTAGCCTGGTATCAGCAGAAACCAGGGCAGCCTCCCAAGCTCCTGACTCATGGT<br>ACATCCAATCTGGAATCTGGGGTCCCATCGCGTTTCCGTGGCAGTGGATCTGGG<br>ACAGAGTTCACTCTCACCATCAGTGGCATGAAGGCTGAAGATGCTGCCACTTAT<br>TACTGTCAAAGTGGTTATTATAGTACTGGTGCGACTTTTGGAGCTGGCACCAAT<br>GTGGAAATCAAG<u>GTGGTTCCTCTAGATCTTCCTCCTCCGGTGGCGGTGGCTCGG</u><br><u>GCGGTGGTGGG</u>CAGTCGCTGGAGGAGTCCGGGGGAGGTCTCTTCAAGCCAACGG<br>ATACCCTGACACTCACCTGCACAGTCTCTGGATTCTCCCTCAGTAACTATGGAA<br>TGGGCTGGGTCCGCCAGGCTCCAGGGAACGGGCTGGAATACATCGGATTCATTA<br>GTAGTGGTGGTAATACATACTACGCGAGCTGGGCGAAAAGCCGATCCACCATCA<br>CCAGAGACACCAACCTGAACACGGTGACTCTGAAAATGAGCAGTCTGACAGCCG<br>CGGACACGGCCACCTATTTCTGTGCGAGAGGTTACCGTGGTTATAATGTTGGTA |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | TATGGATGCTTTTGATGTCTGGGGCCCAGGCAATCTGGTCACCGTCTCCTCAGG<br>GCAACAAGGCTCCATCAGTCACTAGTGGCCCGGGAGGCCA |
| SEQ ID NO: 91 | TBIfabT247 | CCGGCCATGGCTGAGCTCGATCTGACCCAGACTCCATCCTCCGTGTCTGCAGCT<br>GTGGGAGGCACAGTCACCATCAATTGCCAGTCCAGTCAGAGTGTTGATAGTAAC<br>AATTACTTATCCTGGTATCAGCAGAAACCAGGGCAGCCTCCCAAGCTCCTGATC<br>TATGATGCATCCACTCTGGCATCTGGGGTCCCATCGCGGTTCAGCGGCAGTGGA<br>TCTGGGACACAGTTCACTCTCACCATCAGCGAAGTACAGTGTGACGATGCTGCC<br>ACTTACTACTGTCAAGGCAGTTATTATAGTGGTGATTGGTATGGGGCTTTCGGC<br>GGAGGGACCGAGCTGGAGATCCT<u>GGTGGTTCCTCTAGATCTTCCTCCTCTGGTG</u><br><u>GCGGTGGCTCGGGCGGTGGTGGG</u>CAGTCGTTGGAGGAGTCCGGGGGAGGTCTCT<br>TCAAGCCAACGGATCCCCTGACACTCACCTGCACAGTCTCTGGATTCTCCATCA<br>ATGACTACAACATGCAATGGGTCCGCCAGGCTCCAGGGATCGGGCTGGAATGGA<br>TCGGAGCCATTAATGCTTGGGGTGATACATACTATACGAGCTGGGCGAAAAGCC<br>GATCCACCATCACCAGAGACACCAACCTGAACACGGTGACTCTGAAAATGACCA<br>GTCTGACAGCCGCGGACACGGCCACCTATTTCTGTGCNAGAGGTTACAGTCTTG<br>ACATCTGGGGCCCAGGCACCCTGGTCACCGTCTCCTCAGGGCAACCTAAGGCTC<br>CGTCAGTCACTAGTGGCCCGGGAGGCCA |
| SEQ ID NO: 92 | TBIfabT249 | CCCAGCCGGCCATGGCTGAGCTCGTGATGACCCAGACTCCAGCCTCCGTGTCTG<br>AACCTGTGGGAGGCACAGTCACCATCAGTTGCCAGGCCAGTCAGGGTGTTTATA<br>GCGACCGCCTAGCCTGGTATCAACAGAAACCAGGGCAGCCTCCCAAGCTCCTGA<br>TGTATTATGCATCCGATCTGTCATCTGGGGTCCCATCGCGGTTCAAAGGCAGTG<br>GATCTGGGACAGAGTTCACTCTCACCATCAGCGACCTGGAGTGTGCCGATGCTG<br>CCACTTACTACTGTCAAAGCAATTATGGTAGTCTTAGTAGTAGTTATACTTTCG<br>GCGGAGGGACCGAGGTGGTCGTCAAGGTGGTTCCTCTAGATCTTCCTCCTCTGG<br><u>TGGCGGTGGCTCGGGCGGTGGTGGG</u>CAGTCGTTGGAGGAGTCCGGGGGAGGTCT<br>CTTCAAGCCAACGGATACCCTGACACTCACCTGCACAGCCTCCGGATTCACCGT<br>CACTAGCAACGCAATAAGCTGGGTCCGCCAGGCTCCAGGGAACGGGCTGGAATA<br>TATCGGATTCATTGGTGCTGCTGGTAATGCAAACTACGCGAGCTGGGCGAAAAG<br>CCGCTCCACCATCACCAGAAACACCAACCTGAACACGGTGACTCTGAAAATGAC<br>CAGTCTGACAGCCGCGGACACGGCCACCTATTTCTGTGCGAGAGAGGGTGGTTG<br>GGGTACATTGTTTGGTGCTTTTGATTCCTGGGGCCCAGGCACCCTGGTCACCGT<br>CTCCTCAGGGCAACCTAAGGCTCCATCAGTCACTAGTGGCCCGGGAGGCCA |
| SEQ ID NO: 93 | TBIfabP202 | GGCCCAGCCGGCCATGGCTGAGCTCGTGATGACCCAGACTCCACCCTCCCTGTC<br>TGCATCTGTGGGAGAAACTGTCAGGATTAGGTGCCTGGCGAGTGAGAACGTTTA<br>CAGTGCTGTAGCCTGGTATCAACAGAAGCCAGGGAAACCTCCTACACTCCTGAT<br>CTCTGGTGCATCCAATTTAGAATCTGGGGTCCCACCACGGTTCAGTGGCAGTGG<br>ATCTGGGACAGATTACACCCTCACCATCGGCGGCGTGCAGGCTGAAGATGCTGC<br>CACTTACTTCTGTCAAGGGTATAGCAGTTACCTGACTTTTGGAGCTGGCACCAA<br>TGTGGAAATCAA<u>GGTGGTTCCTCTAGATCTTCCTCCTCTGGTGGCGGTGGCTCG</u><br><u>GGCGGTGGTGGG</u>CAGTCGTTGGAGGAGTCCAGGGGAGGTCTCTTCAAGCCAACG<br>GATACCCTGACACTCACCTGCACAGTCTCTGGATTTACCATCGATACCTATGGA<br>GTGACCTGGGTCCGCCAGGCTCCAGGGAACGGGCTGGAATATATCGGATTCATT<br>AGTAGTGGTGGTGCCGCATACTACGCGAGCTGGGCGAAAAGCCGATCCACCATC<br>ACCAGAAACACCAATCTGAACACGGTGACTCTGAAAATGACCAGTCTGACAGCC<br>GCGGACACGGCCACCTATTTCTGTGCGAGAGATCGTGGCTATGTTTATGGTTAT<br>GGTGATGGTACTGACATCTGGGGCCCAGGCACCCTGGTCACCGTCTCCTCAGGG<br>CAACCTAAGGCTCCATCAGTCACTAGTGGCCCGGGAGGCCA |
| SEQ ID NO: 94 | TBIfabP210 | CCCAGCCGGCCATGGCTCAGCCTGTGCTGACTCAGTCGCCCTCTGCGTCTGCTG<br>CCCTGAGATCCTCGGCCAAGCTCACCTGCACCCTGAGCAGTGCCCACAAGAGTT<br>ACGACATTGACTGGTATCAGCAGCAGTCAGGGGAGGCCCCTCGGTACCTAATGC<br>GTCTTAGGAGTGATGGAAAGTACACCAAGGGGACCGGGGTCCCTGATCGCTTCT<br>CGGGCTCCAGCTCTGGGGCTGACCGCTACTTGATCATCCCCAGCGTCCAGGCTG<br>ATGACGGAGCCGACTATTATTGTGGTACAGATTATAGCGGTGGATATGTGTTCG<br>GCGGAGGGACCCAGCTGACCGTCACAGG<u>TGGTGGTTCCTCTAGATCTTCCTCCT</u><br><u>GGTGGCGGTGGCTCGGGCGGTGGTGGG</u>CAGTCGCTGGAGGAGTCCGGGGGAGGC<br>CTGATCAAGCCAACGGATACCCTGACACTCACCTGCACAGTCTCTGGATTCTCC<br>CTCAGTATCTACGACATAAGCTGGGTCCGCCAGGCTCCAGGGAACGGGCTGGAA<br>TGGATCGGAGCCATTGGTAGTGGTGATACCACATACTACGCGAGCTGGGCGAAA<br>AGCCGATCCACCATCACCAGAAACACCTACCTGAACACGGTGACTCTGAAAATG<br>ACCAGTCTGACAGCCGCGGACACGGCCACCTATTTCTGTGCGAGAGGGGGTTA<br>TCCTGGTTCAACATCTGGGGCCCAGGCACCCTGGTCACCGTCTCCTCAGGGCAA<br>CCTAAGGCTCCGTCAGTCACTAGTGGCCCGGGAGGCCA |
| SEQ ID NO: 95 | TBIfabP214 | CCGGCCATGGCTGAGCTCGTGATGACCCAGACTGAATCCCCCGTGTCTGCAGCT<br>GTGGGAGGCACAGTCACCATCAATTGCCAGGCCAGTCAGAGCATTAGCAGTTGG<br>TTGGCCTGGTATCAACAGAAGCCAGGGAAACCTCCTACACTCCTGATCTCTGGT<br>GCATCCAATTTAGAATCTGGGGTCCCACCACGGTTCAGTGGCAGTGGATCTGGG<br>ACAGATTACACCCTCACCATTGGCGGCGTGCAGGCTGAAGATGCTGCCACCTAC<br>TATTGTCTAGGCGGTTATAGTTACAGTAGTATCGGTACGACTTTTGGAGCTGGC<br>ACCAATGTGGAAATCAA<u>GGTGGTTCCTCTAGATCTTCCTCCTCTGGTGGCGGTG</u><br><u>GCTCGGGCGGTGGTGGG</u>CAGGAGCAGCTGGTGGAGTCCGAGGGAGGTCTCTTCA |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | AGCCAACGGATACCCTGACACTCACCTGCACAGTGTCTGGATTCTCCCTCAATA<br>ACTATGGAGTGACCTGGGTCCGCCAGGCTCCAGGGAGGGGCTGGAATGGATCG<br>GAGCCGTTTGGAGTGGTGCTACCACAGACTATGCGAGCTGGGCGAAAAGCCGAT<br>CCACCATCACCAGAAACACCAACGAGAACACGGTGACTCTGAAAATGTCCAGTC<br>TGACAGCCGCGGACACGGCCACCTATTTCTGTGCGAATTTTCCTGGTTATACTT<br>CTGGTACCGACATCTGGGGCCCTGGCACCCTGGTCACCGTCTCCTCAGGGCAAC<br>CTAAGGCTCCGTCAGTCACTAGTGGCCCGGGAGGCCA |
| SEQ ID NO: 96 | TBIfabP217 | CCGGCCATGGCTGAGCTCGTGATGACCCAGACTCCATCCTCTGTGTCTGCAGCT<br>GTGGGAGGCACAGTCACCATCAATTGTCAGGCCAGTCAGAGTGTTAACAACCTC<br>TTAGCCTGGTATCAGCAGAAACCAGGGCAGCCTCCCAAGCTCCTGACTTATGGT<br>ACATCCAATCTGGAATCTGGGGTCCCATCGCGTTTCCGTGGCAGTGGATCTGGG<br>ACAGAGTTCACTCTCACCATCAGTGGCATGAAGGCTGAAGATGCTGCCACTTAT<br>TACTGTCAAAGTGGTTATTATAGTGCTGGTTTGACTTTTGGAGCTGGCACCAAT<br>GTGGAAATCAA<u>GGTGGTTCCTCTAGATCTTCCTCCTCTGGTGGCGGTGGCTCGG<br>GCGGTGGTGGG</u>CAGGAGCAGCTGGAGGAGTCCGGGGGAGGCCTGGTCCAGCCTG<br>GGGGATCCCTGAAACTCTCCTGCAAAGCCTCTGGATTCGACTTCATTAACTATG<br>GAGTAATCTGGGTCCGCCAGGCTCCTGGGAAGGGGCTGGAGTGGATCGGATACA<br>TTGATCCTATTTTTGGTAACACAATCTACGCGAGCTGGGTGAATGACCGATTCA<br>CCATCTCCAGCCACAACGCCCAGAACACGCTGTATCTGCAACTGAACAGTCTGA<br>CAGCCGCGGACACGGCCACCTATTTCTGTGCGAGATGCGGGGATAGACGTGGCT<br>GGGGTTATGGTTTTGATCCCTGGGGCCCAGGCACCCTGGTCACCGTCTCCTCAG<br>GCAACCTAAGGCTCCGTCAGTCACTAGTGGCCCGGGAGGCCA |
| SEQ ID NO: 97 | TBIfabP219 | CCGGCCATGGCTGAGCTCGTGCTGACCCAGACTCCAGCCTCCGTGTCTGAACCT<br>GTGGGAGGCACAGTCACCATCAAGTGCCAGGCCAGTCAGAACATTTACAGTGGT<br>ATATCCTGGTACCAACAGAAGCCAGAGAAACCTCCTACACTCCTGATCTCTGGT<br>GCATCCAATTTAGAACCTGGGGTCCCACCACGGTTCAGTGGCAGTGGATCTGGG<br>ACAGATTACACCCTCACCATTGGCGGCGTGCAGGCTGGAGATGCTGCCACCTAC<br>TACTGTCTAGGCGTTTATAGTTTCGGTAGTACCGATTTGACTTTTGGAGCTGGC<br>ACCAATGTGGAAATCAA<u>GGTGGTTCCTCTAGATCTTCCTCCTCTGGTGGCGGTG<br>GCTCGGGCGGTGGTGGG</u>CAGTCGCTGGAGGAGTCCGGGGGAGGCCTCATCAAGC<br>CAACGGATACCCTGACACTCACCTGCACGGTCTCTGGATTCTCCCTCAGTACCA<br>ATGGAGTGAGTTGGGTCCGCCAGGCTCCAGGGAGCGGGCTGGAATGGATCGGAG<br>CCATTGATCTTTATGGTGCCACATATTACGCGACCTGGGCGAAAAGCCGATCCA<br>CCATCACCAGAAACACCAACCTAAACACGGTGACTCTGAAAATGACCAGTCTGA<br>CAGCCGCGGACACGGCCACCTATTTCTGTGCGAGAGAGGGATATGGTTATCCAA<br>ACATCTGGGGCCCAGGCACCCTGGTCACCGTCTCCTCNGGCAACCTNANNNTCC<br>GTCAGTCACTAGTGGCCCGGGAGGCCA |
| SEQ ID NO: 98 | TBIfabP220 | GGCCCAGCCGGCCATGGCTGAGCTCGATCTGACCCAGACTCCATCGTCCGTGTC<br>TGCAGCTGTGGGAGGCACAGTCAGCATCAGTTGCCAGTCCAGTCAGAGTGTTTA<br>TAATAACTACTTAGCCTGGTATCAGCAGAAACCAGGGCAGCCTCCCAAGCTCCT<br>GATCTATTATGCATCCAAACTGGCATCTGGGGTCCCATCGCGGTTCAAAGGCAG<br>TGGATCTGGGACACAGTTCACTCTCACCATCAGCGACGTGCAGTGTGACGATGC<br>TGCCACTTACTACTGTCAAGGCACTTTTGATAATGGTTTGTACAAGGCTTTCGG<br>CGGAGGGACCGAGCTGGAGATCCT<u>GGTGGTTCCTCTAGATCTTCCTCCTCTGGT<br>GGCGGTGGCTCGGGCGGTGGTGGG</u>CAGTCGTTGGAGGAGTCCGGGGGAGGTCTC<br>TTCAAGCCAACGGATACCCTGACACTCACCTGCACAGTCTCTGGATTCTCCCTC<br>AGTAGCTATGCAATAAGCTGGGTCCGCCAGGCTCCAGGGAACGGGCTGGAATGG<br>ATCGGATACATTAATTACGATGGTATCGCATACTACGCGAGCTGGGCGAAAAGC<br>CGATCCACCATCACCAGAAACACCAACCTGAACACGGTGACTCTGAAAATGACC<br>GGTCTGACAGCCGCGGACACGGCCACCTATTTCTGTGCGAGAGATGACTATACT<br>ACTCCTTATGGTTATCGATTGGNTCTCTGGGGCCAGGGCACCCTGGTCACCGTC<br>TCCTCAGGGCAACCTAAGGCTCCGTCAGTCACTAGTGGCCCGGGAGGCCA |
| SEQ ID NO: 99 | TBIfabP221 | GGCCCAGCCGGCCATGGCTGAGCTCGATATGACCCAGACTCCATCCTCTGTGTC<br>TGCAGCTGTGGGAGGCACAGTCACCATCAATTGCCAGGCCAGTGAAAGCATTAG<br>CAACCTCTTAGCCTGGTATCAGCAGAAACCAGGGCAGCCTCCCAAGCTCCTGAT<br>CTATTCTGCATCCACTCTGGCATCTGGGGTCCCATCGCGTTTCCGTGGCAGTGG<br>ATCTGGGACAGAGTTCACTCTCACCATCAGTGGCATGAAGGCTGAAGATGCTGC<br>CACTTATTACTGTCAAAGTGGTTATTATAGTACTGGTGCGACTTTTGGAGCTGG<br>CACCAATGTGGAAATCAA<u>GGTGGTTCCTCTAGATCTTCCTCCTCTGGTGGCGGT<br>GGCTCGGGCGGTGGTGGG</u>CAGTCGCTGGAGGAGTCCGAGGAGGCCTGGTCCAGC<br>CTGGGGGGATCCCTGAAACTCTCCTGCAAAGGCTCTGGGTTCGACTCGATAGC<br>AATGCAATGTGCTGGGTCCGCCAGGCTCCAGGGAGCGGGCTGGAATGGATCGGA<br>ACCATTACTAGTGGTGGTAGCGCATACTACGCGAGCTGGGCGAAAAGCCGATCC<br>ACCATCACCAGAAACACCAACCTAAACACGGTGACTCTGAAAATGACCAGTCTG<br>ACAGCCGCGGACACGGCCACCTATTTCTGTGCGAGAGGACCTACTTGGGGAATT<br>GGAGATACTTTTCATCCCTGGGGCCCAGGCACCCTGGTCACCGTCTCCTCGGGG<br>CAACCTAAGGCTCCGTCAGTCACTAGTGGCCCGGGAGGCCA |
| SEQ ID NO: 100 | TBIfabT7 | GGCCCAGCCGGCCATGGCTCAGCCTGTGCTGACTCAGTCGCCCTCTGTGTCTGC<br>CGCCCTGGGAGCCTCTGCCAAGCTCACCTGCACCCTGAGCAGTGCCCACAAGAC<br>CTACACCATTGACTGGTATCAACAGCAGTCAGGGGAGGCCCCTCGATACCTGAT |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | GCAGCTTAAGAGTGATGGAAACTACACCAAGGGGACCGGGGTCCCTGATCGCTT<br>CTCGGGCTCCAGCTCTGGGGCTGACCGCTACTTGATCATCCCCAGCGTCCAGGC<br>TGATGACGAAGCGCTGACTACTATTGTGGTGCAGATTATAGCGGTGGGTATGTGTT<br>TGGCGGAGGGACCCAGCTGACCGTCACAGGT<u>GGTGGTTCCTCTAGATCTTCCTC</u><br><u>CTCTGGTGGCGGTGGCTCGGGCGGTGGTGGG</u>CAGGAGCAGCTGGAGGAGTCCGG<br>GGGTCGCCTGGTCAAGCCTGACGAAACCCTGACACTCACCTGCACAGTCTCTGG<br>ACTCTCCCTGAATAATTTTGGAGTGAGCTGGGTCCGCCAGGCCCCAGGAAACGG<br>GCTGGAATGGATCAGAGCCATTGATTTTGGTAGTGGTAGCGCATACTACGCGAA<br>CTGGGCGAAAAGTCGGTCCACCATCACCAGCAACACTCGCCTGAACACGGTGAC<br>TCTGAAAATGATTAGTCTGACAGCCGCGGACACGGCCACCTATTTTTGTTCGAG<br>AGGAGACATCTGGGGCCCAGGCACCCTGGTCACCGTCTTCTCAGGGCAACCTAA<br>GGCTCCGTCAGTCACTAGTGGCCCGGGAGGCCA |
| SEQ ID NO: 102 | TBIfabT14 | GCCCAGCCGGCCATGGCTGAGCTCGATATGACCCAGACTCCATCCTCCGTGTCT<br>GCAGCTGTGGGAGGCACAGTCACCATCAGTTGCCAGGCCAGTCAGAGTGTTTAT<br>AATAACAACAATTTATCCTGGTATCAGCAAAAACCAGGGCAGCCTCCCAAGCTC<br>TTGATCTACGATGCATCCAAATTGGCATCTGGGGTCCCATCGCGGTTCAAAGGC<br>AGTGGATCTGGGACACAGTTCACTCTCACCATTAGCGACCTGGAGTGTGACAAT<br>GCTGCCACTTACTTCTGTCAACAGGGTTATGATGGTAGTGATGTTGATAATGTT<br>TTCGGCGGAGGGACCGAGGTGGTGGTCAAG<u>GTGGTTCCTCTAGATCTTCCTCCT</u><br><u>CTGGTGGCGGTGGCTCGGGCGGTGGTGGG</u>CAGTCGGTGAAGGAGTCCGAGGGAG<br>GTCTCTTCAAGCCAACGGATACCCTGACACTCACCTGCACAGTCTCTGGATTCT<br>CCCTCAGTAACTATGCAATAAACTGGGTCCGCCAGGCTCCAGGGGAGGGGCTGG<br>AGTGGATCGGCTATATTCCTACTTTTGGTAGCACGTACTACGCGAGCTGGG<br>TGAATGACCGATTCACCATCTCCAGCCACAACGCCCAGAACACGCTGTATCTGC<br>AACTGAACAGTCTGACACCTGCGGACACGGCCACCTATTTCTGTGCGAGAGATG<br>ATATTAGTATTAGTGGTTATTCATTTGACATCTGGGGCCCAGGCACCCTGGTCA<br>CCGTCTCCTCAGGGCAACCTAAGGCTCCATCAGTCACTAGTGGCCCGGGAGGCC<br>A |
| SEQ ID NO: 103 | TBIfabP9 | GGCCCAGCCGGCCATGGCTGAGCTCGTGCTGACCCAGACTCCACCCTCCCTATC<br>TGCATCTGTGGGAGAAACTGTCAGGATTAGGTGCCTGGCCAGTGAGTTCCTTTT<br>TAATGCTGTATCCTGGTATCAACAGAAGCCAGAGAAACCTCCTACACTCCCGAT<br>CTATGGTGCATCCAATTTAGAATCTGGGGTCCCACCACGGTTCAGTGGCAGTGG<br>ATCTGGGACACAGTTCACTCTCACCATCAGCGACCTGGAGTGTGACGATGCTGC<br>CACTTACTACTGTGCAGGCGATTATAGTGATTGGATTTATGCTTTTGGCGGGGG<br>GACCGAGGTGGTGGTCAAG<u>GTGGTTCCTCTAGATCTTCCTCCTCTGGTGGCGGT</u><br><u>GGCTCGGGCGGTGGTGGG</u>CAGTCGGTTGGAGGAGTCCGGGGGAGGTCTCTTCAAG<br>CCTGGAGGATCCCTGACACTCACCTGCACAGTCTCTGGATTCACCATCACTAGC<br>TACCACATGTGCTGGGTCCGCCAGGCTCCAGGGAACGGGCTGGGATGGATCGGA<br>GCCGTTAGTGCTAGCGGACACACATATTACGCGAACTGGGCGAAAAGCCGATCC<br>ACCATCACCAGAGACACCAACTTAAACACCATGACTCTGAAAATGACCAGTCTG<br>ACAGCCGCGGACACGGCCACCTATTTCTGTGCGACACCATATCCTGGTTATGAT<br>ATTGATCCCTTTGACATCTGGGGCCCAGGCACCCTGGTCACCGTCTCCTCAGGG<br>CAACCTAAGGCTCCGTCAGTCACTAGTGGCCCGGGAGGCCA |
| SEQ ID NO: 104 | TBIfabP12 | GGCCCAGCCGGCCATGGCTGAGCTCGTGCTGACCCAGACTCCATCCTCCGTGCC<br>TGCAGCTGTGGGAGGCACAGTCACCATCGATTGCCAGTCCAGTGAGAGTGTTTA<br>TAATAACAACAACTTAGCCTGGTATCAGCAGAAACCAGGGCAGCCTCCCAAGCT<br>CCTGATCTACGGGGCATCCACTCTGGCATCTGGGGTCTCATCGCGGTTCAAAGG<br>CAGTGGATCTGGGACAGAGTTCACTCTCACCATCAGCGACCTGGAGTGTGCCGA<br>TGCTGCCACTTACTACTGTCAACAGGGTTATAGTATTGGTAATGTAGATAATGC<br>TTTCGGCGGAGGGACCGAGCTGGAGATCCTGGTGGTTCCTCTAGATCTTCCTCC<br><u>TCTGGTGGCGGTGGCTCGGGCGGTGGTGGG</u>CAGTCGCTGGAGGAGTCCGGGGGA<br>GGTCTCTTCAAGCCAACGGATACCCTGACACTCACCTGCACGGTCTCTGGATTC<br>TCCCTCAGTAGCTATGGAATTACTTGGGTCCGCCAGGCTCCAGGGAACGGGCTG<br>GAATGGATCGGCGCCATTGGTAGTGATGCTAAAACATACTACGCGAGCTGGGCG<br>AAAGGCCGATCCACCATCACCGGAGACACCAACCTGAACACGGTGACTCTGAGA<br>ATGACCAGTCTGACAGCCGCGGACACGGCCACCTATTTCTGTGCGAGATATTTT<br>GATTGGTTTAATGTGGACATCTGGGGCCCAGGCACCCTGGTCACCGTCTCCTCA<br>GGGCAACCTAAGGCTCCATCAGTCACTAGTGGCCCGGGAGGCCA |
| SEQ ID NO: 105 | TBIfabP18 | GGCCCAGCCGGCCATGGCTGAGCTCGTGATGACCCAGACTCCAGCCTCTGTGGA<br>GGTAGCTGTGGGAGGCACTGTCACCATCAAGTGCCAGGCCAGTCAGAGCATTAG<br>TAGCTACTTAGCCTGGTATCAACAGAAACCAGGGCAGCCTCCCAAGCTCCTGAT<br>CTACAAGGCTTCCACTCTGGCATCTGGGGTCCCGTCGCGGTTCAAAGGCAGTGG<br>ATCTGGGACACAGTTCACTCTCACCATCAGCGATGTGGTGTGTGACGATGCTGC<br>CACTTACTACTGTCAGGATATAAAGGTGGTAGTAGTGATGGTAGTGCTTTCGG<br>CGGAGGGACCGAGCTGGAGATCCT<u>GGTGGTTCCTCTAGATCTTCCTCCTCTGGT</u><br><u>GGCGGTGGCTCGGGCGGTGGTGGG</u>CAGTCGGTGAAGGAGTCCGAGGGAGGTCTC<br>TTCAAGCCAACGGATACCCTGACACTCACCTGCACAGTCTCTGGATTCTCCCTC<br>AGTAGCTATGAGTGAGCTGGGTCCGCCAGGCTCCAGGGAACGGGCTGGAATGG<br>ATCGGAGCCATTAGTAGTGGTGGTGACGCATACTACGCGAGCTGGGCGACCAGC<br>CGATCCACCATCACCAGAAACACCAACCTGAACACGGTGACTCTGAAAATGACC<br>AGTCTGACAGCCGCGGACACGGCCACCTATTTCTGTGCGAGACATTTTGGTTAT |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | GGTACTGCTGGGGGCATCTGGGGCCCAGGCACCCTCGTCACCGTCTCTTCAGGG<br>CAACCTAAGGCTCCGTCAGTCACTAGTGGCCCGGGAGGCCA |
| SEQ ID NO: 106 | TBIfabP19 | GGCCCAGCCGGCCATGGCTCAGCCTGTGCTGACTCAGTCGCCCTCTGCATCTGC<br>TGCCCTGGGATCCTCGGCCAAGCTCACCTGCACTCTGAGCAGTGCTCACAAGAC<br>CTACTATATTGAATGGTATCAGCAGCAGCAAGGGGAGGCCCCTCGGTACCTGAT<br>GCAGGTTAAGAGTGATGGAAGCTACACCAAGGGGACCGGGGTCCCTGATCGCTT<br>CTCGGGCTCCAGCTCTGGGGCTGACCGCTACTTGATCATCCCCAGCGTCCAGGC<br>TGATGACGAAGCCGACTACTATTGTGGTGCAGATTATAGCGGTGGGTATGTGCT<br>CGGCGGAGGGACCCAGCTGACCGTCACAGGT<u>GGTGGTTCCTCTAGATCTTCCTC</u><br><u>CTCTGGTGGCTCGGGCGGTGGTGGGCAGTCGGTGGAGGAGTCCGGGGGAGGTCT</u><br>CTTCAAGCCAGCGGATACCCTGACACTCACCTGCACAGTCTCTGGATTTTCCCT<br>CAGTTACCCTGGAGTGAGCTGGGTCCGCCAGGCTCCAGGGAACGGGCTGGAATA<br>CATCGGATTCATTAATGCTGATGGTGACTCATACTACCCGACCTGGGCGAAACG<br>CCGATCCACCATCACCAGAAACACCAACCTGAACACGGTGACTCTGAAAATGAC<br>CAGTCTCACAGCCGCGGACACGGCCACCTATTTCTGTGCGAGAGAGGGTGGCTG<br>GGGTACATTGTTTGGTGCTTTTGATTCCTGGGGCCCAGGCACCCTAGTCACCGT<br>CTTCTCAGGGCAACCTAAGGCTCCGTCAGTCACTAGTGGCCCGGGAGGCCA |
| SEQ ID NO: 107 | TBIfabT114 | GGCCCAGCCGGCCATGGCTCAGCCTGTGCTGACTCAGTCGCCCTCTGCATCTGC<br>TGCCCTGGGATCCTCGGCCAAGCTCACCTGCACTCTGAGCAGTGCTCACAAGAC<br>CTACTATATTGACTGGTATCAGCAGCAGCAAGGGGAGGCCCCTCGGTACCTGAT<br>GCAGCTTGGGAGTGATGGAAGTTACACCAAGGGGACCGGGGTCCCTGATCGCTT<br>CTCGGGCTCCAGCTCTGGGGCTGACCGCTACTTGATCATCCCCAGCGTCCAGGC<br>TGATGACGAAGCCGACTACTATTGTGGTTCAGATTATAGCGGTGGGTATGTGTT<br>CGGCGGAGGGACCCAGCTGACCGTCACAGGT<u>GGTGGTTCCTCTAGATCTTCCTC</u><br><u>CTCTGGTGGCGGTGGCTCGGGCGGTGGTGGGCAGTCGCTGGAGGAGTCCGGGGG</u><br>AGGTCTCTTCAAGCCAGCGGATACCCTGACACTCGCCTGCACAGTCTCTGGATT<br>CTCCCTCAGTACTTATGGAGTGATCTGGGTCCGCCAGGCTCCAGGGAAGGGGCT<br>GGAATACATCGCATACATTAATTATAGTGGTAGTCCATACTACGCGAGCTGGGC<br>GAAAAGCCGATCCACCATCACCAGAAACACCAACGAGAAAACGGTGACTCTGAA<br>AATGACCAGTCTGACAGCCGCGGACACGGCCACCTATTTCTGTGCGAGGGGTGT<br>TCCTGGTTACAATGCGGATATGGGGGACATCTGGGGCCCAGGCACCCTGGTCAC<br>CGTCTTCTCAGGGCAACCTAAGGCTCCATCAGTCACTAGTGGCCCGGGAGGCCA |
| SEQ ID NO: 108 | TBIfabT116 | GGCCCAGCCGGCCATGGCTCAGCCTGTGCTGACTCAGTCGCCCTCTGTGTCTGC<br>CGCCCTGGGAGCCTCTGCCAAGCTCACCTGCACCCTGAGCAGTGCCCACAAGAC<br>CTACACCATTGATTGGTATCAGCAGCAGCAAGGGGAGGCCCCTCGGTACCTGAT<br>GCAGCTTAAGAGTGATGGAAGCTACACCAAGGGGACCGGGGTCCCTGATCGCTT<br>CTCGGGCTCCAGCTCTGGGGCTGACCGCTACTTGATCATCCCCAGCGTCCAGGC<br>TGATGACGAAGCCGACTACTATTGTGGTGCAGATTATAGCGGTGGGTATGTGTT<br>CGGCGGAGGGACCCAGCTGACCGTCACAGGT<u>GGTGGTTCCTCTAGATCTTCCTC</u><br><u>CTCTGGTGGCGGTGGCTCGGGCGGTGGTGGGCAGTCGGTGGAGGAGTCCAGGGG</u><br>GAGGTCTCTTCAAGCCAACGGATACCCTGACACTCACCTGCACAGTCTCTGGAT<br>TCTCCCTCAGTGGCTATGGAGTGAGCTGGGTCCGCCAGGCTCCAGGGAACGGGC<br>TGGAATGGATCGGAGCCATTAGTAGTGGTGGTAGCGCATACTACGCGAGATGGG<br>CGAAAAGCCGCTCCACCATCACCAGAAACACCAACCTGAACACGGTGACTCTGA<br>AAATGACCAGTCTGACAGCCGCGGACACGGCCACCTATTTCTGTGCGAGAGGTT<br>ACTATACTGCTATTGGTGGTACTTATGACAATGCTTTTGATCCCTGGGGCCCAG<br>GCACCCTGGNCACCGTCTCCTCAGGGCAACCTAAGGCCAGTCACTAGTGGCCCG<br>GGAGGCCA |
| SEQ ID NO: 109 | TBIfabT124 | GGCCCAGCCGGCCATGGCTGAGCTCGATATGACCCAGACTCCACCCTCCCTGTC<br>TGCATCTGTGGGAGAAACTGTCAGGATTAGGTGCCTGGCCAGTGAGGACATTGG<br>CAGTGCTATATCCTGGTACCAACAGAAGCCAGGGAAACCTCCTACACTCCTGAT<br>CTATGGTGTATTTAATTTAGAATCTGGGGTCCCACCACGATTCAGTGGCAGTGG<br>ATCTGGGACAGATTACACCCTCACCATTGGCGGCGTGCAGGCTGAAGATGCTGC<br>CACCTACTACTGTCTAGGCGGTGCTAGTGACAGTAGTACCGGTTTGACTTTTGG<br>AGCTGGCACCAATGTGGAAATCAAG<u>GTGGTTCCTCTAGATCTTCCTCCTCTGGT</u><br><u>GGCGGTGGCTCGGGCGGTGGTGGG</u>CAGTCGGTGAAGGAGTCCGAGGGAGGTCTC<br>TTCAAGCCAACGGATACCCTGACACTCACCTGCACAGTCTCTGGATTCTCCCTC<br>AGTAACTATGGAGTGAGCTGGGTCCGCCAGGCTCCAGGGAACGGGCTGGAATAC<br>ATCGGCTTCATTAGTAACGGTGGTGCCACATTCTACGCGACCTGGGCGAGAAGC<br>CGAGCCACCATCACCAGAAACACCGGCCTGAACACGGTGGCTCTGACAATGACC<br>AGTCTGACAGCCGCGGACACGGCCACCTATTTCTGTGTGAGGGATTCTGTTGCT<br>ACTTATGCTACTGATGTTGCTGCTTTTGATCCCTGGGGCCCAGGCACCCTGGTC<br>ACCGTCTCCTCAGGGCAACCTAACTCCGTCAGTCACTAGTGGCCCGGGAGGCCA |
| SEQ ID NO: 110 | TBIfabT129 | GCCCAGCCGGCCATGGCTCAGCCTGTGCTGACTCAGTCGCCCTCCCTGTCTGCG<br>TCTCTGGGCACAACGGCCAGACTCACCTGCACCTGAGCACTGGCTACGTGTT<br>GGCGAGTACCCTTTAGTGTGGCTCCAGCAGGTGCCAGGGAGGCCTCCCAGGTAT<br>CTCCTGAGCTTCACCTCAGATGAAGACAAACACCATGACTCTTGGGGCCCACC<br>CGCTTTTCTGGATCCAAAGACACCTCAGAGAATACCTTTATCCTGAGCATCTCT<br>GGGCTGCAGCCCGAGGACGAGGCCGACTATTACTGTGCTACAGCTCATGGTAGT<br>GATAACAGCCTCCATTATGTCTTCGGCGGAAGGACCCAGCTGACCGTCACAGGT |

TABLE 2-continued

TEGS-specific antibody region nucleic acid sequences

| SEQ ID NO | Clone Number | Nucleic Acid Sequence (VL-linker-VH; linker underlined) |
|---|---|---|
| | | <u>GGTGGTTCCTCTAGATCTTCCTCCTCTGGTGGCGGTGGCTCGGGCGGTGGTGGG</u><br><u>CAGTCGGTGAAGGAGTCCGAGGGAGGTCTCTTCAAGCCAACGGATACCCAGACA</u><br>CTCACCTGCACAGTCTCTGGATTCTCCCTCAGTAGCAATGCAATAAGCTGGGTC<br>CGCCAGGCTCCAGGGAACGGGCTGAAAAGCATCGGATTCATTAATAGTGGTGGT<br>GGCGCATATTACGCGACCTGGGCGAAAAGCCGATCCACCATCACCAGAAACACC<br>AACGAGAACACGGTGACTCTGAAAATGACCAGTCTGACAGCCGCGGATACGGCC<br>ACCTATTTCTGTGCGAGAACACCCCATTATTATGATACTTATGATACCTCATTT<br>AACATATGGGGCCCAGGCACCCTGGTCACCGTCTTCTCAGGGCAACCTAAGGCT<br>CCGTCAGTCACTAGTGGCCCGGGAGGCCA |
| SEQ ID NO: 111 | TBIfabT134 | GGCCCAGCCGGCCATGGCTCAGCCTGTGCTGACTCAGTCGCCCTCTGCATCTGC<br>TGCCCTGGGATCCTCGGCCAAGCTCACCTGCACTCTGAGCAGTGCTCACAAGAC<br>CTACTATATTGAATGGTATCAGCAGCAGCAAGGGGAGGCCCCTCGGTACCTGAT<br>ACAACTTAAGAGTGATGGAAGCTACACCAAGGGGACCGGGGTCCCTGATCGCTT<br>CTCGGGCTCCAGCTCTGGGACTGACCGCTACTTGATCATCTCCAGCGTCCAGGC<br>TGAGGACGAAGCCGACTACTTCTTGTGGTGCAGATTATAGTGGTGGGTTTGTGTT<br>CGGCGGAGGGACCCAGCTGACCGTCACAGGT<u>GGTGGTTCCTCTAGATCTTCCTC</u><br><u>CTCTGGTGGCGGTGGCTCGGGCGGTGGTGGGCAGTCGCTGGAGGAGTCCGGGGG</u><br>AGGTCTCTTCAAGCCAACGGATACCCTGACACTCACCTGCACAGTCTCTGGATT<br>CGCCCTCAATAACTACAACATACACTGGGTCCGCCAGGCTCCAGGGAACGGGCT<br>GGAATGGATCGGAGCCATTGGTAGTAGTGGTAGCGCATACTACGCGAGCTGGGC<br>GAAAAGCCGATCCACCATCACCAGAAACACCAACCTGAACACGGTGACTCTGAA<br>AATGACCAGTCTGACAGCCGCGGACACGGCCACCTATTTCTGTGCGAGAGGTTA<br>TAATTCTGATGATTCTTATCTCTGGGGCCCAGGCACCCTGGTCACCGTCTCCTC<br>AGGGCAACCTAAGGCTCCATCAGTCACTAGTGGCCCGGGAGGCCA |
| SEQ ID NO: 112 | TBIfabP212 | CCGGCCATGGCTGAGCTCGTGCTGACCCAGACTCCACCCTCCCTGTCTGCATCT<br>GTGGGAGGCACAGTCACCATAAACTGTCTGGCGAGTGAGAACGTCTACAGTGCT<br>GTAGCCTGGTATCAACAGAAGCCAGGGAAACCTCCTACACTCCTGATCTCTGGT<br>ACATCCAATTTAGAGGCTGGGGTCCCACCACGGTTCAGTGGCAGTGGATCTGGG<br>ACAGATTACACCCTCACCATCGGCGGCGTGCAGGCTGAAGATGCTGCCACTTAC<br>TTCTGTCAAGGGTATAGCAGTTACCCTTTGACTTTTGGAGCTGGCACCAATGTG<br>GAAATCAAG<u>GTGGTTCCTCTAGATCTTCCTCCTCGGTGGCGGTGGCTCGGGCGG</u><br><u>TGGTGGGCAGTCGGTGGAGGAGTCCAGGGGGAGGCCTGGTCAAGCCTGGGGAT</u><br>ACCCTCACACTCACCTGCACAGTCTCTGGATTCCCCCTCAGCAGCTACGACATG<br>AACTGGGTCCGCCAGGCTCCAGGGAGGGGCTGGAATGGATCGGATGGATTACT<br>TATGATGGTTACAATCACTACGCGAGCTGGGCGAATGGCCGATCCACCATCACC<br>AGAAACACCAACGAGAACGCGGTGACTCTGAAAATGACCAGTCTGACAGCCGCG<br>GACACGGCCACCTATTTCTGTGCGCGAGATTACTATAATGGTGCTTATGTTTAT<br>GCCTTTAACATCTGGGGCCCAGGCACCCTGGTCACCGTCTCCTCAGGGCAACCT<br>AAGGCTCCATCAGTCACTAGTGGCCCGGGAGGCCA |

TABLE 3

PCR Primer Sequences

| SEQ ID NO | SEQ NAME | NUCLEIC ACID SEQUENCE |
|---|---|---|
| SEQ ID NO: 113 | SKVHF01 | GGTGGTTCCTCTAGATCTTCCTCCTCTGGTGGCGGTGGCTCGGG<br>CGGTGGTGGGCAGTCGGTGGAGGAGTCCRGG |
| SEQ ID NO: 114 | SKVHF02 | GGTGGTTCCTCTAGATCTTCCTCCTCTGGTGGCGGTGGCTCGGG<br>CGGTGGTGGGCAGTCGGTGAAGGAGTCCGAG |
| SEQ ID NO: 115 | SKVHF03 | GGTGGTTCCTCTAGATCTTCCTCCTCTGGTGGCGGTGGCTCGGG<br>CGGTGGTGGGCAGTCGYTGGAGGAGTCCGGG |
| SEQ ID NO: 116 | SKVHF04 | GGTGGTTCCTCTAGATCTTCCTCCTCTGGTGGCGGTGGCTCGGG<br>CGGTGGTGGGCAGSAGCAGCTGGWGGAGTCC |
| SEQ ID NO: 117 | SKCHR01 | TGGTGTTGGCCTCCCGGGCCACTAGTGACTGAYGGAGCCTTAGG<br>TTGC |
| SEQ ID NO: 118 | SKOVERPA<br>DR1 | TGGTGTTGGCCTCCCGGGCCACTA |
| SEQ ID NO: 119 | SKVLKF01 | GGGCCCAGCCGGCCATGGCTGAGCTCGTGMTGACCCAGACTCCA |
| SEQ ID NO: 120 | SKVLKF02 | GGGCCCAGCCGGCCATGGCTGAGCTCGATMTGACCCAGACTCCA |
| SEQ ID NO: 121 | SKVLKF03 | GGGCCCAGCCGGCCATGGCTGAGCTCGTGATGACCCAGACTGAA |

TABLE 3-continued

PCR Primer Sequences

| SEQ ID NO | SEQ NAME | NUCLEIC ACID SEQUENCE |
|---|---|---|
| SEQ ID NO: 122 | SKVLLF01 | GGGCCCAGCCGGCCATGGCTGAGCTCGTGCTGACTCAGTCGCCCTC |
| SEQ ID NO: 123 | SKVLLF02 | GGGCCCAGCCGGCCATGGCTCAGCCTGTGCTGACTCAGTCG |
| SEQ ID NO: 124 | SKOVERPADF1 | TACTCAGGGCCCAGCCGGCCATGGCTGA |
| SEQ ID NO: 125 | SKVLKR01 | GGAAGATCTAGAGGAACCACCAGGATCTCCAGCTCGGTCCC |
| SEQ ID NO: 126 | SKVLKR02 | GGAAGATCTAGAGGAACCACCTTGATTTCCACATTGGTGCC |
| SEQ ID NO: 127 | SKVLKR03 | GGAAGATCTAGAGGAACCACCTTGACSACCACCTCGGTCCC |
| SEQ ID NO: 128 | SKVLLR01 | GGAAGATCTAGAGGAACCACCACCTGTGACGGTCAGCTGGGTCC |
| SEQ ID NO: 129 | SKpf41F01-2 | TAAGCAGAATTCGGCCCAGCCGGCCGCGGTGGGAACACTAGGA |
| SEQ ID NO: 130 | SKpf41F02-3 | AGCAGAATTCTGGCCCAGCCGGCCGCGGTGGGAACACTAG |
| SEQ ID NO: 131 | SKpf41F03-4 | AGCAGAATTCTAGGCCCAGCCGGCCGCGGTGGGAACACTA |
| SEQ ID NO: 132 | SKpf41R01-2 | CTCTAGATCTGGCCTCCCGGGCCTTTTTATATACCACAGCCAGTTTG |
| SEQ ID NO: 133 | SKpf41R01-3 | CTCTAGATCTAGGCCTCCCGGGCCTTTTTATATACCACAG |
| SEQ ID NO: 134 | SKpf41R01-4 | CTCTAGATCTATGGCCTCCCGGGCCTTTTTATATACCACA |
| SEQ ID NO: 135 | SKRTlucF01 | AACATAAAGAAAGGCCCGGC |
| SEQ ID NO: 136 | SKRTlucR01 | GCCTTATGCAGTTGCTCTCCA |

SEQ ID NOs 113-128 are used for amplification of rabbit VL and VH cDNA for production of the phagemid inserts.

SEQ ID NOs 129-134 are used for amplification of gp41, ligation into the pFUSE hIgG1-2 vector, and excision to generate sfiI restriction sites in multiple frames.

SEQ ID NOs 135-136 are used for amplification of firefly luciferase reverse transcripts produced in the Reverse Transcriptase assay.

In one embodiment, a gene encoding an anti-virus particle product antibody is chemically synthesized. Nucleotide sequences encoding the amino acid sequences shown in Table 1 are selected, broken into multiple oligonucleotides, chemically synthesized, and successively ligated together, to produce a gene encoding an anti-virus particle product antibody.

Once an antibody or ABP sequence is known, particularly the CDRs, any suitable method of making an ABP therefrom can be employed, including both cell-based and cell-free methods. Various methods of cell-free antibody synthesis are found in Carlson, E et al., *Biotechnology Advances*, 2012, 30: 1185-94. In cell-based methods, an anti-virus particle product monoclonal antibody or ABP gene is inserted into an expression vector for construction of a recombinant expression vector. An expression vector generally has a promoter region upstream of a translation start codon (ATG), as well as a polyA signal region downstream of a translation stop codon (TAA, TGA, or TAG). A recombinant expression vector is introduced into a host cell, and the transformed host cells are cultured to express the anti-virus particle product monoclonal antibody. *Escherichia coli*, yeast, or other animal cells can be used as host cells.

An immunoassay using an anti-virus particle product monoclonal antibody (or fragment thereof) can be used to detect the presence of HIV. In one embodiment, the immunoassay procedure involves allowing an anti-virus particle product monoclonal antibody to react with a sample including an antigen, and allowing any resulting antigen-antibody complex to further react with an antibody having a detectable label. In a further embodiment, detection or quantification of the antibody may be performed by a method such as enzyme-linked immunosorbent assay (ELISA), fluorescent immunoassay, radioimmunoassay (RIA), luminescent immunoassay, enzyme antibody technique, fluorescence antibody technique, immunonephelometry, latex agglutination reaction, latex turbidimetry method, hemagglutination, particle agglutination, Western blotting method, competition method, or sandwich method. In a further embodiment, the sandwich method uses a solid-phased antibody or a labeled antibody as the anti-virus particle product monoclonal antibody.

In some embodiments, the monoclonal antibody is sensitized/immobilized to a solid phase carrier, such as polystyrene, styrene-butadiene copolymer, (meth)acrylic acid ester polymer, latex, gelatin, a liposome, a microcapsule, erythrocyte, silica, alumina, carbon black, a metallic compound, metal, ceramic, or a magnetic body. Sensitization methods include physical adsorption method, chemical bond method, or a combined physical adsorption and chemical bond method. In an embodiment, measurement is performed using an optical method, such that the sample reacts with an antibody (sensitized to a solid phase carrier or unsensitized), and a transmitted or scattering light is measured by an end point method or a rate method. In another embodiment, measurement is performed by visual observation, such that the sample reacts with an antibody that has been sensitized to a solid phase carrier in a vessel (for example, a plate or microtiter plate), and the agglutinated reaction product is visually observed. A microplate reader is further used in some embodiments to observe the agglutinated reaction product.

In a like manner, TEGS can be used in any suitable immunoassay format, such as those described above, to detect and/or quantify HIV antibodies or ABPs in a sample. TEGS can be immobilized on an immunoassay support in, for example, a standard sandwhich format, or used in solution in, for example, a standard competition assay.

FIG. 1 provides an illustrated flowchart that summarizes a method for producing TEGS, according to an embodiment. First, the HIV virus is isolated from multiple sources of acute infection virus (i.e., from antibody low/negative subjects) by using specialized coated beads (102). Next, the virus is propagated in a purified and homogenous cell substrate (104). In an embodiment, the virus is propagated in serum-free medium. The number of passages of virus is minimized, and the capacity of the cell substrate to produce type 1 interferons (e.g., interferon-alpha), type 2 interferons (e.g., interferon-gamma), and beta-chemokines (e.g., RANTES, MIP1 alpha, and MIP1 beta) is reduced. The cytokines can inhibit virus replication and add complexity to the TEGS composition. Next, the fluid containing the virus is concentrated by using molecular weight cutoff (MWCO) filters (106). Use of serum-free medium is required in an embodiment to use the MWCO filters, to prevent clogging the filter pores. Thus, ultracentrifugation, which potentially disrupts any non-covalently attached envelope proteins, is not required. Next, the fluid containing virus is treated with agents to inactivate virus (108). These agents include a cyclodextrin and Benzonase. In an embodiment, the fluid containing the virus is additionally exposed to heat (e.g., 56° C. or less). The fluid containing the virus is then processed to remove any inactivating agents (110). In one embodiment, a smaller MWCO filter (such as a 10 KDa filter) is used for this step to prevent the loss of free gp41. Finally, the inactivated virus composition is reconstituted in final buffer (112). In some embodiments, the final buffer is dPBS with no calcium or magnesium ions. Additives (such as azide or PEG) are used in some embodiments to stabilize proteins and prevent microbial contamination. In other embodiments, other additives such as CpG-rich DNA are used to boost localized immune response to TEGS.

Pharmaceutical Compositions of the Invention

Methods for treatment of diseases are also encompassed by the present invention. Said methods of the invention include administering a therapeutically effective amount of anti-virus particle product antibody (for example, a TEGS-specific antibody) for preventing or treating HIV infection. These antibodies can be formulated in pharmaceutical compositions. These compositions can comprise, in addition to one or more of the anti-virus particle product antibody, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Other routes of administration of the pharmaceutical composition are in accord with known methods, e.g. orally, through injection by intraperitoneal, intracerebral (intraparenchymal), intracerebroventricular, intramuscular, intraocular, intraarterial, intraportal, intralesional routes, intramedullary, intrathecal, intraventricular, transdermal, or intraperitoneal; as well as intranasal, enteral, topical, sublingual, urethral, vaginal, or rectal means, by sustained release systems or by implantation devices. Administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

The pharmaceutical compositions of the present invention are preferably made under GMP conditions. It is also preferred that the compositions are packaged in a suitable sterile container, typically in a unit dosage form. The composition can be administered for therapeutic or prophylactic reasons. For example, therapeutic TEGS-specific antibodies can be administered as a substitute for an anti-retroviral drug. Therapeutic antibodies can also be administered in addition to an anti-retroviral drug, and/or added to a combination of antiretroviral drugs in Highly Active Anti-Retroviral Therapy (HAART). In an embodiment, this combination of antibody and antiretroviral drug is administered to a patient who is failing antiretroviral therapy. In another embodiment, the composition is administered prophylactically for protection of a fetus from an infected mother.

An effective amount of a pharmaceutical composition to be employed therapeutically will depend on the therapeutic context and objectives. One of skill in the art will appreciate that appropriate dosage levels for treatment will vary depending on the indication for which the therapeutic antibody is being used, the route of administration, and the size and condition of the patient. A typical dosage may range from about 0.1 mg/kg to up to about 100 mg/kg or more. Therapeutic antibodies may be preferably injected or administered intravenously. In some embodiments, the antibodies are lyophilized.

In some embodiments, therapeutic antibodies are administered at a dosage of from about 1 ng of antibody per kg of subject's weight per dose, to about 10 mg/kg/dose, or preferably from about 500 ng/kg/dose to about 5 mg/kg/dose. In other embodiments, a dosage for subcutaneous or intravenous administration of a dose of 0.5, 1, 3, 5, 6, 7, 8, 9, 10, 11, 12, 15, or 20 milligrams of therapeutic antibody is administered per kilogram body mass of the subject (mg/kg) (Flego et al, *BMC Medicine* 2013, 11:4). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The term "therapeutically effective amount" refers to the amount of an agent determined to produce a therapeutic response in a mammal. Such therapeutically effective amounts are readily ascertained by one of ordinary skill in the art.

The term "modulator," as used herein, is a compound that changes or alters the activity or function of a molecule. For example, a modulator can cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described in, e.g., U.S. Pat. No. 6,660,843 (corresponding to PCT Application No. WO 01/83525).

The terms "patient" and "subject" are used interchangeably and include human and non-human animal subjects as well as those with formally diagnosed disorders, those without formally recognized disorders, those receiving medical attention, those at risk of developing the disorders, etc. In some embodiments, the patient is a human subject with a homozygous deletion of 32 base pairs in the CCR5 gene, which encodes a major HIV-1 coreceptor (Buseyne F et al., *J Infect Dis* 1998, 178: 1019-1023). In an embodiment, the patient is a human subject who is failing antiretroviral therapy.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

In an embodiment, an anti-virus particle product monoclonal antibody is formulated into a pharmaceutical composition and administered to a human patient. In a further embodiment, the dosage for the treatment is dependent on the degree of symptoms, age, and body weight of the patient, as well as the administration method. The antibody weight for the pharmaceutical composition ranges from 10 ng to 100 mg/kg of body weight, in an embodiment.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Manufacture of the Virus Particle Product

Those of ordinary skill in the art can appreciate that there are many processes employed in the production of the non-infectious virus particle product that retains trimeric envelope glycoprotein subunits (TEGS) in their natural state. While TEGS is the virus particle product in the following examples, other virus particle products may also be produced and used. In a preferred embodiment, infectious virus stocks were prepared from plasma in mitogen-stimulated PBMC or CD4+ blood cells (Vyas G N. Human peripheral blood mononuclear cell substrate for propagating wild type HIV-1, *Dev Biol (Basel)* 2001 106:345-356), purified and concentrated, and then inactivated by treatment to deplete membrane cholesterol, capsid proteins, and RNA (FIG. 1).

Example 2: Production of High-Titer HIV-1 Stocks

The production of the viral particle product requires appreciable amounts of infectious virus. In a preferred embodiment, high-titer stocks of HIV were produced using HIV isolated from HIV-infected individuals who were in the earliest stage of infection prior to antibody detection. Such viruses have been called 'Fiebig I/II' isolates or 'founder' viruses (Fiebig E W, et al., *AIDS* 2003, 17:1871-1879; Keele B F et al. *Proc Nat'l Acad Sci* 2008, 105: 7552-7557). The expansion of virus was performed using primary blood cells that can be obtained from blood banks while preserving the anonymity of the blood donors. Primary blood cells were used to expand the virus in its most natural form, as opposed to the use of cell lines that produce variants of the original virus.

Peripheral blood mononuclear cells (PBMCs) were isolated by routine Ficoll density gradient separation procedures (Vyas G N et al., *Blologlcals,* 2012 40: 15-20). To further purify blood cells for use in the expansion of virus, CD4+ cells were isolated from the PBMC by positive selection using immunomagnetic beads or other cell sorting methods. The PBMC or PBMC subpopulation was stimulated with PHA (1-3 micrograms per ml) for 2-4 days in medium A or B; medium A is the traditional growth medium that is comprised of RPMI 1640, 10% heat-inactivated fetal calf serum, 2 mM L-glutamine, 100 U/ml penicillin, 100 μg/ml streptomycin, and 10 ng/ml recombinant human IL-2; medium B is a preferred growth medium that is comprised of F12/DMEM, 1× insulin, transferrin, selenium (ITS), and 10 ng/ml recombinant human IL-2. The use of medium B has advantages including that viral particle products can be produced in the absence of serum. The mitogen-stimulated primary cells were acutely infected for 2 hr (37° C. with periodic mixing) with infectious virus (e.g., 10e4 TCID50).

Five days later, the virus-infected cells were collected, washed, and mixed (1:10) with fresh mitogen-stimulated cells to allow for virus expansion. These cells (10e9/device) were then placed into a gas permeable rapid cell expansion device (e.g., G-Rex bioreactor, Wilson Wolf, New Brighton, Minn.). The cell culture fluids were collected and exchanged with fresh complete medium every 3 days for a period of 9-21 days. Peak virus concentrations (~1 ug/ml p24) were observed at days 6-12 in many cases. HIV-1 levels were measured by p24 ELISA or assays for reverse transcriptase activity.

Figure 1A:
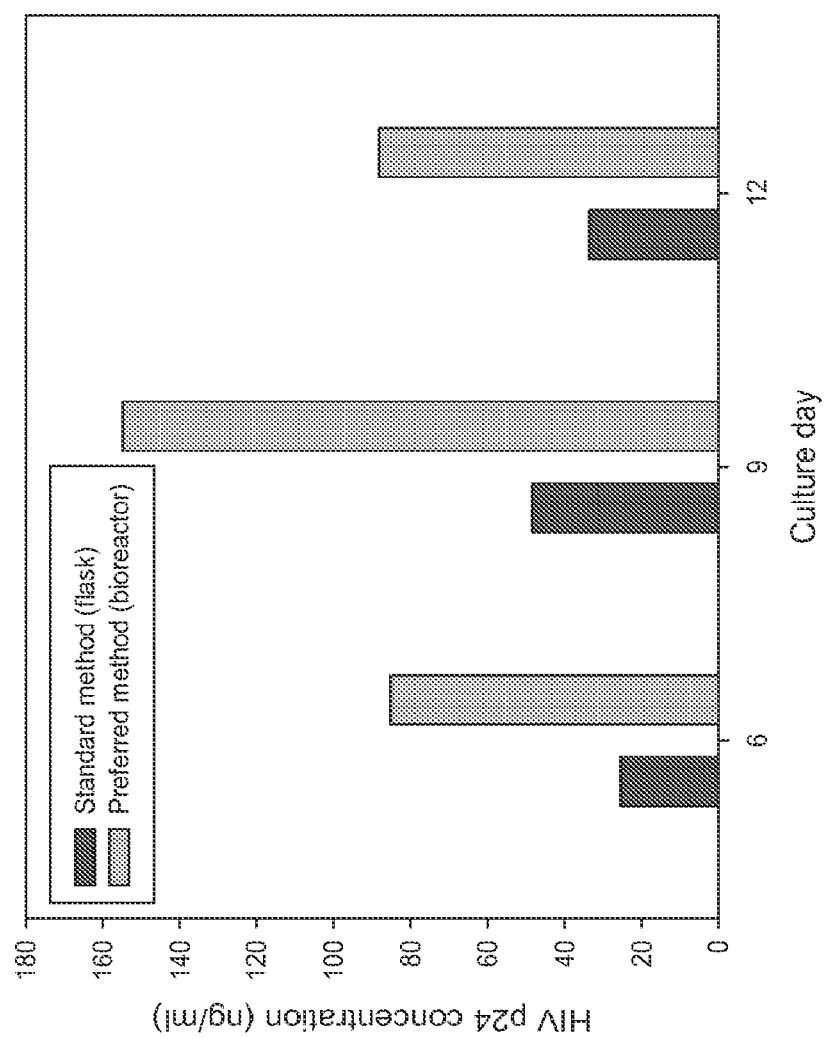
FIG. 1A illustrates a method for producing virus stocks for use in preparing a virus particle product, in accordance with an embodiment of the invention.

In FIG. 1A, it is demonstrated that the preferred procedures allow for substantial gains in the amount of virus produced in cell culture. In this case, the use of a bioreactor for the culture of virus-infected cells was found to be superior to the use of a conventional flask.

In another method of producing high-titer HIV-1 stocks, peripheral blood mononuclear cells (PBMCs) were isolated by routine Ficoll density gradient separation procedures (Vyas G N et al., *Biologicals*, 2012 40: 15-20). To further purify blood cells for use in the expansion of virus, CD4+ cells were isolated from the PBMC by positive selection using immunomagnetic beads or other cell sorting methods. The PBMC or PBMC subpopulation was stimulated with PHA (1-3 micrograms per ml) for 2-4 days in medium A or B; medium A is the traditional growth medium that is comprised of RPMI 1640, 10% heat-inactivated fetal calf serum, 2 mM L-glutamine, 100 U/ml penicillin, 100 μg/ml streptomycin, and 10 ng/ml recombinant human IL-2; medium B is a preferred growth medium that is comprised of F12/DMEM, 1× insulin, transferrin, selenium (ITS), and 10 ng/ml recombinant human IL-2. The use of medium B has advantages including that viral particle products can be produced in the absence of serum. The mitogen-stimulated primary cells were acutely infected for 2 hr (37° C. with periodic mixing) with infectious virus (e.g., 10e4 TCID50). Next, the virus-infected cells were collected and expanded as described above.

Example 3: Measuring Viruses and Virus Particle Products

The assay most widely used in research laboratories for measuring HIV levels is an ELISA that detects the p24 capsid protein. The p24 protein is the most abundantly produced virus protein in infected cells and is the most abundant protein in the virus. Thus, the p24 ELISA is a useful assay for detecting the presence of HIV. However, because the majority of p24 is not incorporated into the virus and because p24 is present in defective viruses, the p24 ELISA does not reliably measure infectious viruses. An alternative assay measures levels of the virus reverse transcriptase protein. The present application embodies a preferred method for measuring virus reverse transcriptase: a one-step quantitative non-radioactive RT-PCR method. The method involved pelleting virus from an aliquot of the sample to be tested, lysis of the pelleted virions, the addition of a reaction mixture, incubations of varying lengths of time at various temperatures, and the acquisition and analysis of the data. This method is applied to the measurement of HIV, other viruses, and virus-like constructs.

Figure 2:
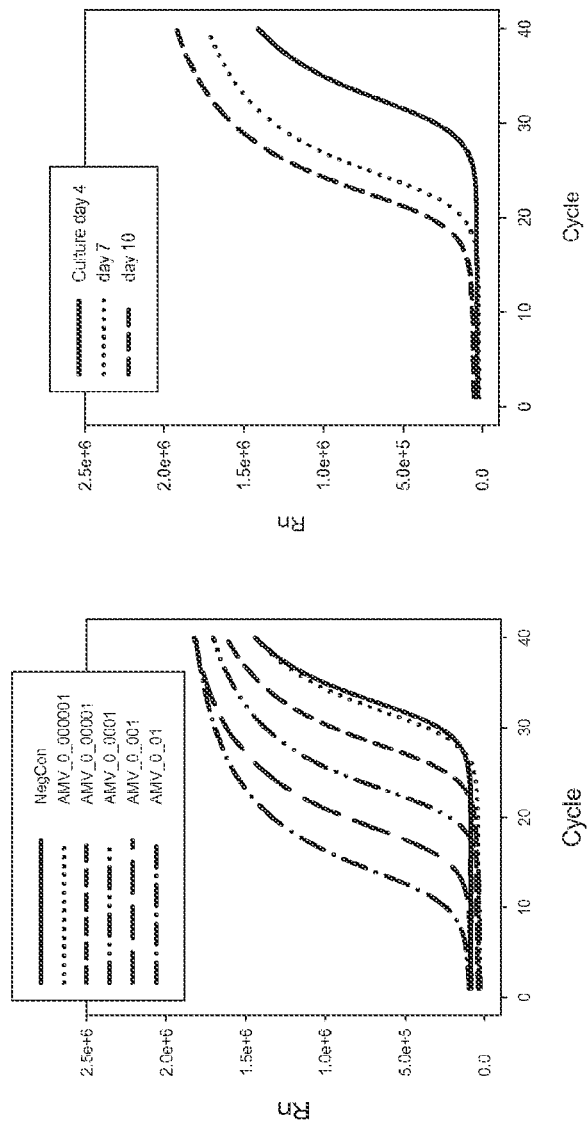
FIG. 2 illustrates results of an RT-PCR assay for validation and optimization for measuring virus, in accordance with an embodiment of the invention.

In the case of FIG. 2, it is demonstrated that a quantitative RT-PCR assay has been validated and optimized for the measurement of virus. The left panel shows the performance of serial dilutions (10-fold) of a purified virus reverse transcriptase enzyme. The right panel shows the assay applied to the measurement of HIV at days 4, 7, and 10 of cell culture.

Example 4: Refinement of the Virus Particle Product

The preferred method for the production of a virus particle product from an infectious virus stock employs gentle virus inactivation procedures collectively termed "cholesterol extraction with nucleic acid depletion" or "CENAD". Briefly, fluids containing infectious virions were concentrated using centrifugal filtration devices (e.g., 100 kDa molecular weight cut off, MWCO) and/or ultracentrifugation. The retentate or pellet was treated with beta-cyclodextrin to remove membrane-bound cholesterol, permeabilize the virions, and to expel capsid proteins, reverse transcriptase and viral RNA (Graham D R et al., *J Virol* 2003, 77: 8237-8248). The resulting viral particle product was further washed and concentrated using centrifugal filtration devices (e.g., 100 kDa MWCO, Millipore). This method for producing the virus particle product is a modified (streamlined and optimized) version of the one reported by Vyas et al (Vyas G N et al., *Blologlcals* 2012, 40: 15-20).

Example 5: Coupling Multiple Virus Particle Products

The virus particle products derived from distinct infectious viruses can vary in protein sequence and structure. Therefore, collections of pooled virus particle products can be more diverse in protein composition than individual virus particle products (Vyas G N. *Dev Biol* (*Basel*) 2001, 106: 345-356; Vyas G N et al., *Biologicals* 2012, 40: 15-20). The simplest procedure for creating diverse virus particle products is to combine equal or non-equal amounts of individual virus particle products in a single vessel. The surface of a microsphere is coated with a variety of virus particle products. This is achieved by co-incubating virus particle products with DC-SIGN-expressing lipoparticles in PBS (pH7, 30 min, 4° C.), followed by washing and concentrating steps using 100 kDa MWCO filters. Alternatively, specialized microparticles such as Virobeads (AdemTech) can be employed to capture virus particle products. We have termed microparticles that are coated with pooled virus particle products "iTEGS". In one example, iTEGS is used as an antigen that presents multiple virus particle products in a concentrated format. A product that displays multiple virus particle products is highly useful for vaccines that present multiple antigens from one or several different types of viruses.

Figure 3:
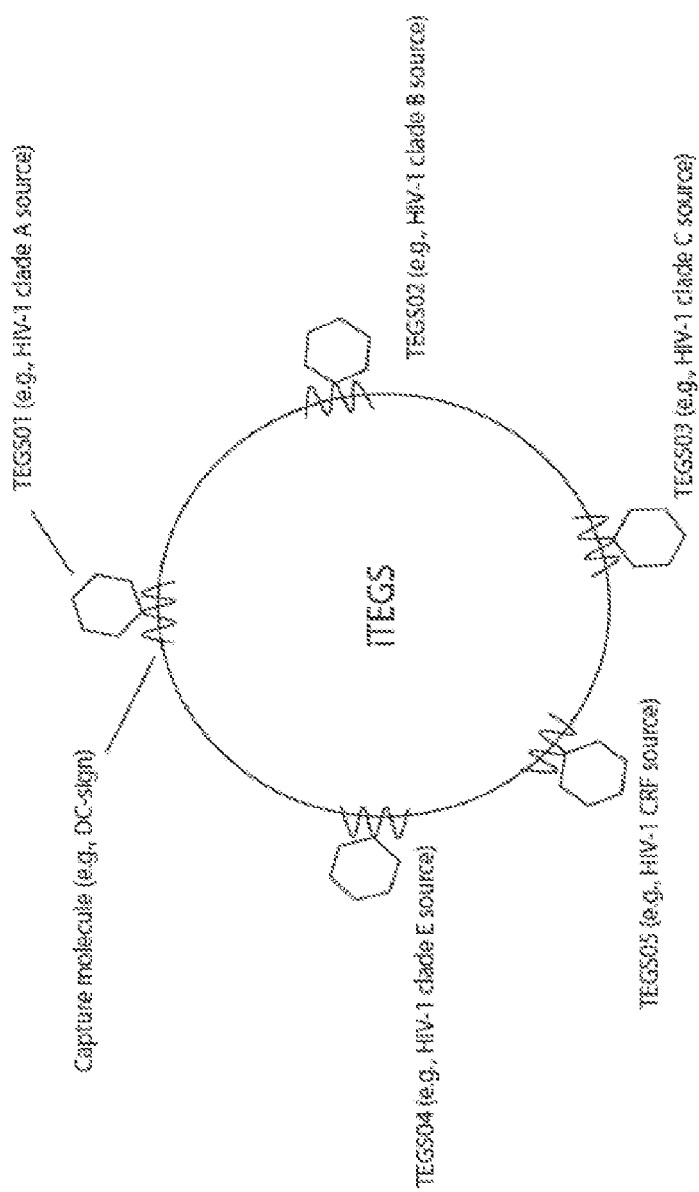
FIG. 3 illustrates a diagram of a particle that features multiple virus particle products, in accordance with an embodiment of the invention.

In the case of FIG. 3, a diagram of one type of iTEGS is presented. In this case, viral particle products are produced from multiple clades of HIV-1. Then the viral particle products are pooled and captured with a microparticle (e.g., DC-SIGN-expressing lipoparticles or Virobeads)

Example 6: Metrics of ABPs

TEGS is useful for the capture, analysis, and/or measurement of ABPs. An example is the use of the virus particle product as a means to capture anti-virus antibodies on a solid platform. The method involved coating a surface, such as high-binding plastic, with the virus particle product, followed by the input of a source that potentially contained anti-viral antibodies. After an incubation period of 1-2 hours, the surface was washed, and then bathed in a detection antibody that broadly bound antibodies from the species used to generate the anti-viral antibody. Emphasized is that the virus particle product, where displaying natural envelope proteins, binds to antibodies that would otherwise remain unbound by viral proteins that have been subjected to procedures that disrupt the natural envelope structure. Thus the present virus particle product has advantages over commonly used virus lysates that are prepared using procedures that disrupt the natural structure of envelope proteins. The use of the virus particle product can be applied to a wide variety of immunodetection platforms including ELISA, ELISpot assays, bead-based assays, flow cytometry, mass spectrometry, microscopy-based assays, and Western and other blot-based assays.

Figure 4:
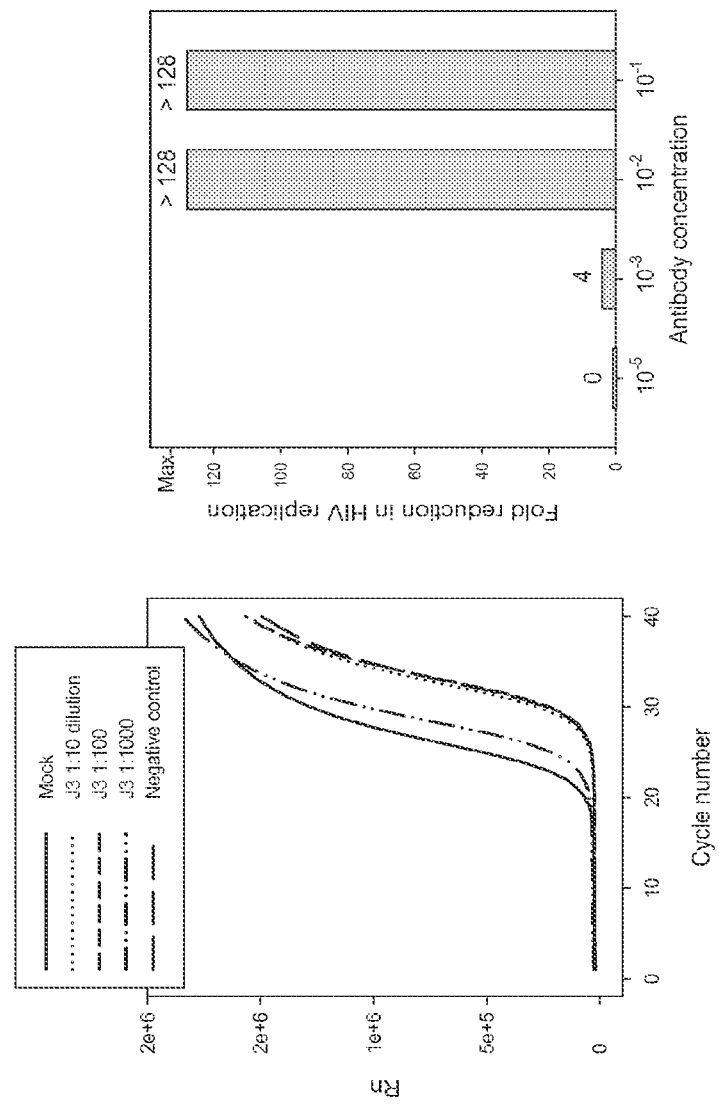
FIG. 4 illustrate (left) RT-PCR data and (right) a bar graph that demonstrate that a virus particle product can be sued to capture, detect, and measure anti-virus particle product ABPs, in accordance with an embodiment of the invention.

In the case of FIG. 4, it is demonstrated that the virus particle product can be used for the capture, detection and measurement of anti-virus particle product ABPs. The left panel shows raw RT-PCR data from an experiment where a virus-particle-product-specific antibody (J3) (McCoy et al., *J Exp Med* 2012: 209(6) 1091-103) was incubated with a virus particle product and then evaluated for infectivity in cell culture. The right panel is a bar graph that shows the data in terms of the fold-reduction in HIV replication.

Example 7: TEGS Production

In a separate experiment, a TEGS composition was generated. HIV-1 was isolated from a 10-year old plasma specimen (stored at −80° C.) obtained from an individual at the time of acute HIV infection, when the nucleic acid amplification test for HIV was positive and the antibody test was negative. Specialized beads (Virobeads; Accurate Chemical & Scientific Corp., Westbury, N.Y.) were used to capture the virus from plasma. This method allows for successful isolation of infectious HIV where other procedures fail, perhaps due to the separation of infectious virus from inhibitory factors commonly found in plasma by using other procedures. Using the specialized beads also acts to concentrate the virus.

The virobead-captured HIV was then propagated in vitro using primary blood cells that were obtained from blood banks while preserving the anonymity of the blood donors. Primary blood cells were used to expand the virus in its most natural form, as opposed to the use of cell lines that could produce variants of the original virus. The HIV was used for in vitro infection of primary CD4+ cells that were isolated from a leukoreduction chamber (LRC) obtained from a healthy blood bank donor. In some cases, a PCR test for CCR5 genotyping was performed and used to screen blood from a healthy donor. R5-TEGS was produced in CCR5 positive cells. Briefly, peripheral blood mononuclear cells (PBMCs) were isolated from the total blood in the LRC using a routine ficoll gradient separation procedure. From the PBMCs, CD4+ cells were isolated using immunomagnetic beads (Miltenyi Biotec, Auburn, Calif.; Stemcell Technologies, Vancouver BC, Canada). The CD4+ cells were mitogen stimulated in vitro with PHA (2 µl/mL phytohemagglutinin, Sigma-Aldrich, St. Louis, Mo.) and then acutely infected with the virobead-captured HIV. The acutely HIV-infected CD4+ cells were cultured in serum-free medium: F12/DMEM (Thermo Fisher Scientific, Life Technologies), 1×ITS (Thermo Fisher Scientific, Life Technologies), 3 µl/mL human IL-2 (Thermo Fisher Scientific, Invitrogen), and 1× pen/strep (UCSF Cell Culture Facility). The cells were cultured in the serum-free medium and cell culture supernatants were collected at routine intervals for up to 14 days. In some cases, freshly stimulated CD4+ was added to increase HIV yields. A portion (half) of the cell culture supernatant was collected and replaced with fresh serum-free medium every 2-3 days. HIV levels in the cell culture supernatants were measured using a p24 ELISA assay and a reverse transcriptase (RT) assay.

PCR amplicons were cloned into a pcr2.1-TOPO vector (Invitrogen) that was used to transform competent cells. Colonies from the transformed *E. coli* preparations were selected and cultured. Plasmids from the cultures were isolated (minipreps; Qiagen) and sequenced (ElimBio, Hayward, Calif.). The resulting sequences were compiled and analyzed using tools in the LANL online database.

HIV virions in the cell culture supernatants were concentrated using molecular weight cutoff (MWCO) filtration. The supernatants containing an appreciable amount of HIV were centrifuged (e.g., 2000×g for 15 minutes) and filtered through 0.2µ filters to remove large particulate matter. The supernatants were then concentrated using 100 kDa molecular weight cutoff filters (MWCO; e.g., Amicon filters; Millipore Corp., Billerica, Mass.).

Concentrated HIV virions were treated with agents to render them non-infectious. The HIV virions were treated with beta-cyclodextrin (BCD, Trappsol, CTD Inc., High Spring, Fla.) to remove cholesterol from virion membranes. As a third orthogonal inactivation procedure, fluids can be briefly heated (e.g. up to 56° C. for 5 min). The benefit of this method for inactivating viruses is that the inactivation procedures are not known to modify the native envelope structure of the virus. Also, BCD can act to release virus proteins that are not attached to the surface of the virus. Notably, BCD can be increasingly effective in the reduced presence of serum. The inactivated virus material was washed with PBS, using MWCO filters. This procedures removed BCD and washed away smaller proteins and debris. Notably, this procedure involving MWCO filters was facilitated by the production of serum-free fluids. The retentate was resuspended in a buffer that varied with the intended use of the resulting TEGS composition. Additives were sometimes used to stabilize the proteins (e.g., PEG) and prevent microbial contamination (e.g., azide). Other additives (e.g. CpG-rich DNA) could be used to boost the localized immune response to the TEGS composition. The resulting material was then analyzed for its HIV Env composition using ELISA and Western blot procedures.

Example 8: TEGS Elicit Production of TEGS-Specific Antibodies in Immunized Animals New Zealand white rabbits were immunized with the TEGS generated in Example 7 (Pacific Immunology, San Diego, Calif.). The immunization protocol included 4 injections and 4 production bleeds, with injections taking place at weeks 0, 3, 6, and 10, and bleeds taking place at weeks 7, 9, 11, and 13. At week 14, the rabbit was euthanized, followed by an exsanguinations bleed and a harvesting of the bone marrow and spleen.

Figure 5:
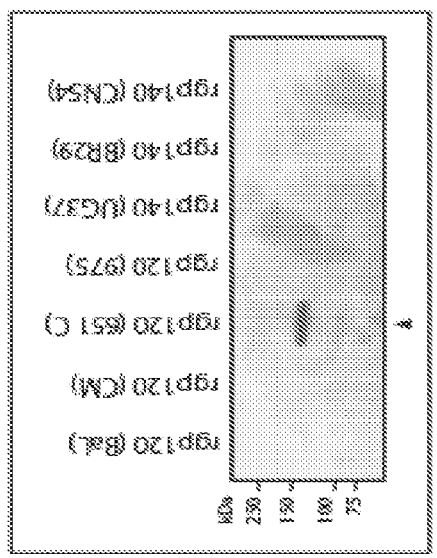
FIG. 5 shows SDS-PAGE gels demonstrating that rabbits immunized with TEGS produce TEGS-specific antibodies, in accordance with an embodiment of the invention.
Figure 5:
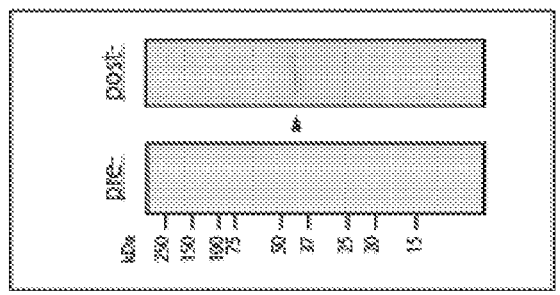
Figure 5:
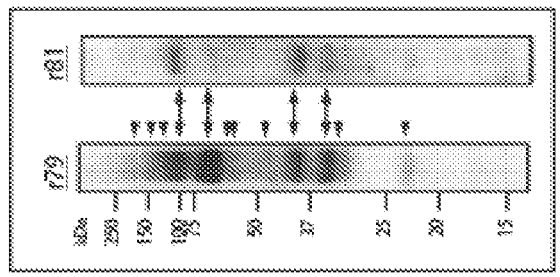

FIG. 5 illustrates SDS-PAGE gels showing that rabbits immunized with TEGS produce TEGS-specific antibodies. The LEFT panel shows the immunoreactivity of the final bleed sera from two rabbits (#79 and #81) against TEGS separated by SDS-PAGE under denaturing and reducing conditions. Arrows denote bands of appreciable intensity above background. The MIDDLE panel shows the immunoreactivity of pooled sera from the pre- and post-immunization (final) bleeds of rabbits #79 and #81 against recombinant gp41 protein separated by SDS-PAGE under denaturing and reducing conditions. The RIGHT panel shows the immunoreactivity of pooled post-immune sera from rabbits #57 and #58 against various recombinant gp120 (lanes 1-4) and gp140 proteins (lanes 5-7) separated by SDS-PAGE under denaturing and reducing conditions. Together, the data in FIG. 5 demonstrate that rabbits immunized with TEGS produce antibodies against TEGS and recombinant gp41 and gp120 proteins. Thus, it can be concluded that TEGS prepared from an acute HIV infection isolate elicit a pronounced anti-HIV antibody response.

Figure 6:
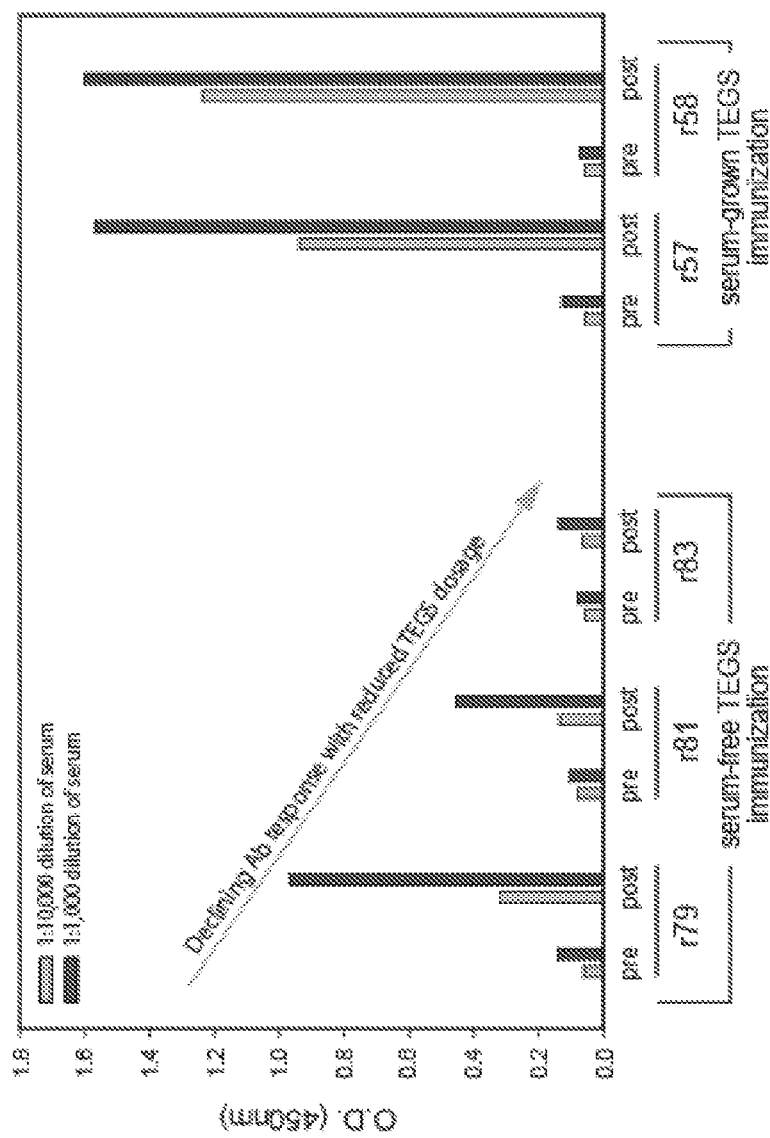
FIG. 6 is a graph demonstrating that the antibody response elicited by immunizing rabbits with TEGS is dose dependent, in accordance with an embodiment of the invention.

FIG. 6 is a graph demonstrating that the antibody response elicited by immunizing rabbits with TEGS is dose dependent, and serum dependent. A microtiter plate was coated with 100 ul of a virus particle product (1:5 dilution of TBI01280 stock in PBS). Pre- and post-immune sera from rabbits immunized with serum-free TEGS or serum-grown TEGS were diluted 1:10000 (grey bars) or 1:1000 (black bars) in PBS and added to the coated plates. Shown are the resulting O.D.s (450 nm). Respectively, rabbits #79, #81, and #83 received TEGS doses of 300×, 30×, and 3× volumetric equivalents based on the volume of virus particle product concentrated using MWCO filters. The TEGS in these cases were grown in serum-free medium (medium B). Rabbits #57 and #58 were immunized with equivalent TEGS doses, the TEGS in these cases grown in serum-grown medium (medium A). A strong dose-response relationship is observed. Based on the frequencies of virus-particle-specific hybridoma fluids, a similar dose-response relationship was observed in mice immunized with TEGS (see Example 10). These data are consistent with the elevated frequency of bands and the heightened band intensities seen with rabbit #79 as compared to #81 in FIG. 5 (LEFT). Altogether, these data help establish a TEGS optimal immunizing dose.

Figure 7:
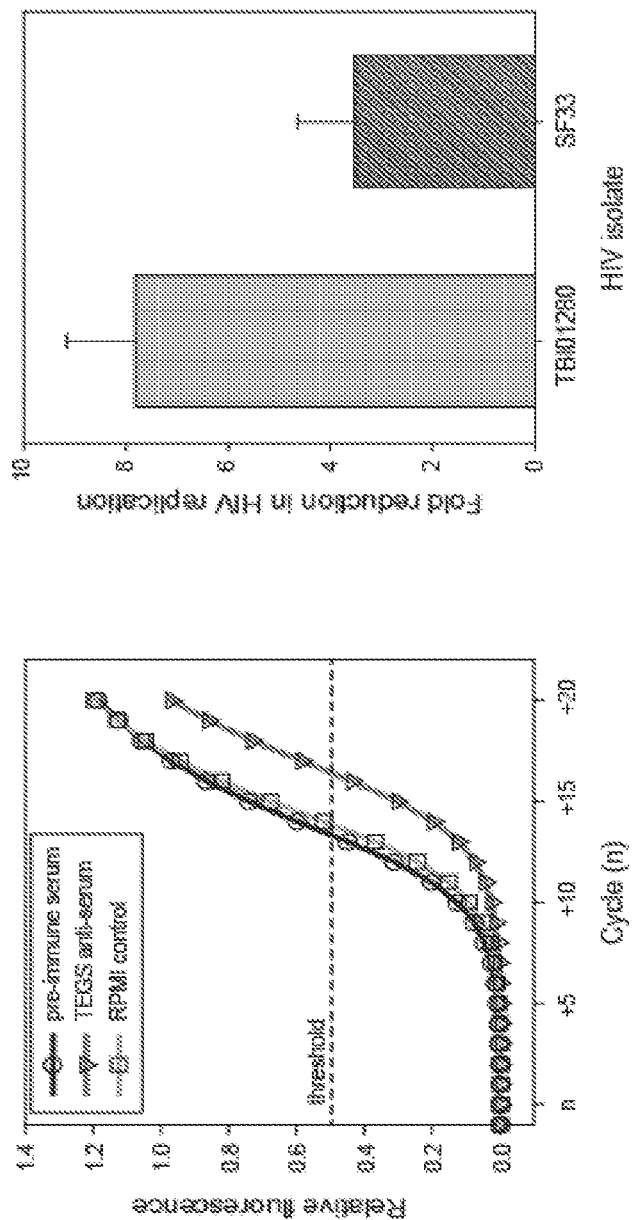
FIG. 7 illustrates (left) a representative amplification profile, and (right) neutralization results, that illustrate that TEGS anti-serum neutralizes HIV-1, in accordance with an embodiment of the invention.

FIG. 7 illustrates that the TEGS anti-serum inhibits HIV infection (i.e., neutralizes HIV). The pre-immune serum and the final bleed serum from rabbit #79 were tested in a neutralization assay. Briefly, the sera were pre-adsorbed with human PBMC to remove antibodies capable of binding human cells. Next, the sera were added to aliquots (1000 TCID$_{50}$) of two distinct HIV-1 isolates (TBI01280 (R5) and HIV-1 SF33 (X4)), resulting in the dilution of the serum. RPMI was used as a control. After a 1-hour incubation period (37° C.), the entire 200 μl serum/virus mixture was added to 1×10$^6$ PHA-stimulated human CD4 cells. Following a 2 hour incubation (37° C. with periodic mixing), the cells were washed with RPMI and plated in duplicate in a 96-well plate (BD Falcon; 1×10$^5$ cells per well) in complete growth medium. The medium was changed at 3-day intervals and aliquots of the supernatants were stored. HIV levels in the supernatants were measured by an RT-PCR assay designed to measure reverse transcriptase (RT) levels. FIG. 7 shows a representative amplification profile (LEFT) and neutralization results (RIGHT), which reveal that the TEGS antiserum from rabbit #79 markedly reduces the replication of two distinct HIV-1 isolates in vitro, presumably by binding virus envelope proteins. Notably, anti-sera from rabbits immunized with serum-grown TEGS (i.e., using medium A), did not neutralize HIV-1 in repeated experiments. Therefore, serum-free TEGS (i.e., using medium B) is distinguished by the specificities and/or titers of the antibodies elicited in immunized rabbits.

Figure 8:
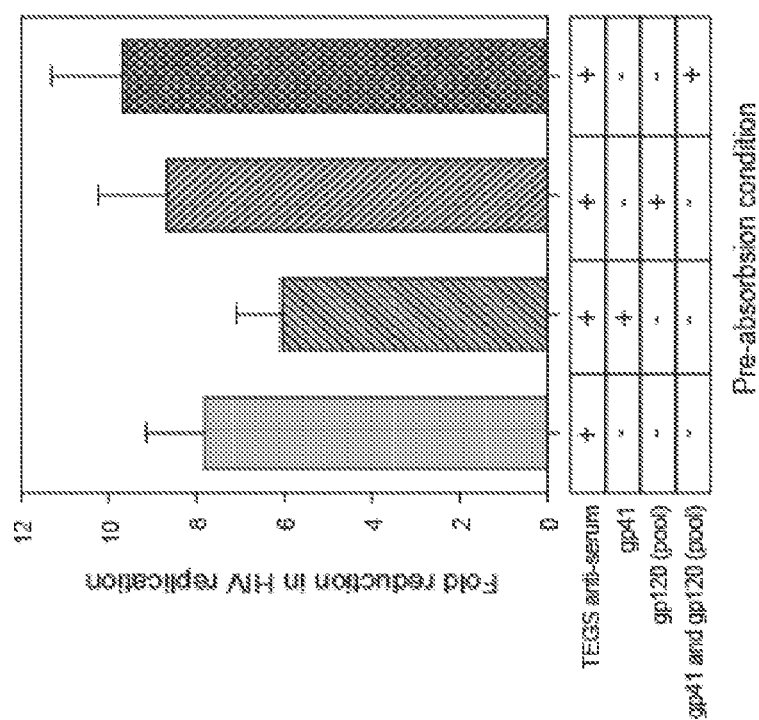
FIG. 8 is a chart demonstrating that select recombinant HIV-1 envelope proteins do not block neutralizing activity of TEGS antiserum from a rabbit, in accordance with an embodiment of the invention.

FIG. 8 is a chart showing that select recombinant HIV-1 envelope proteins do not block the neutralizing activity of the TEGS antiserum from rabbit #79. Briefly, the specificity of the neutralizing anti-serum was evaluated by pre-abosrbing the anti-serum with recombinant gp41 and gp120 proteins (1 μl/ml; NIH AIDS Reagents Program) prior to performing neutralization assays with TBI01280. FIG. 8 shows that the reductions in HIV-1 replication result from treatment of the virus particle product with TEGS antiserum alone, TEGS antiserum pre-absorbed with recombinant gp41, TEGS antiserum pre-absorbed with a pool of recombinant gp120 proteins, and TEGS antiserum pre-absorbed with recombinant gp41 and pooled gp120 proteins. The pre-absorption procedure did not lower the antiviral activity of the TEGS antiserum. Thus, it can be concluded that the neutralizing activity of the TEGS antiserum is attributable to the recognition of an epitope that is not present in recombinant gp41 and gp120 monomeric proteins. These results provide evidence in support of the premise that TEGS can elicit antibodies against a discontinuous determinant(s) present in the quaternary structure of the native HIV-1 envelope.

Figure 9:
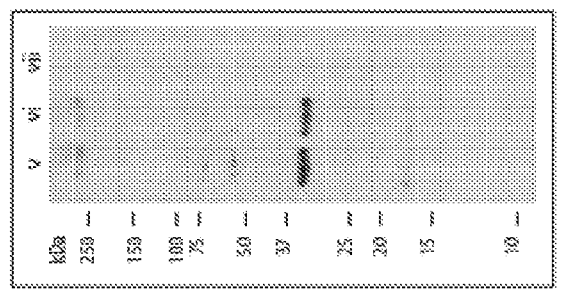
FIG. 9 shows (left) a gel, and (right) Western blot results, which illustrate refinement of a virus particle product, in accordance with an embodiment of the invention.
Figure 9:
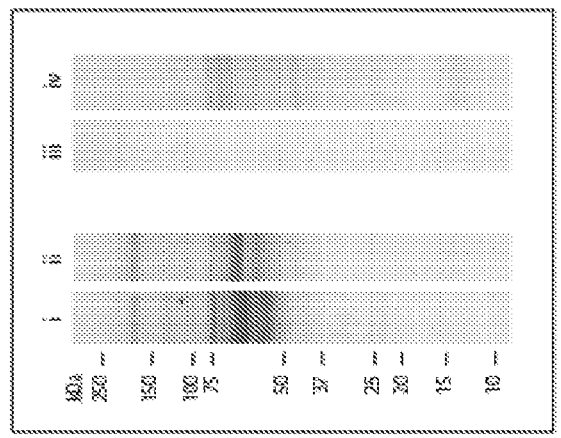
Figure 10:
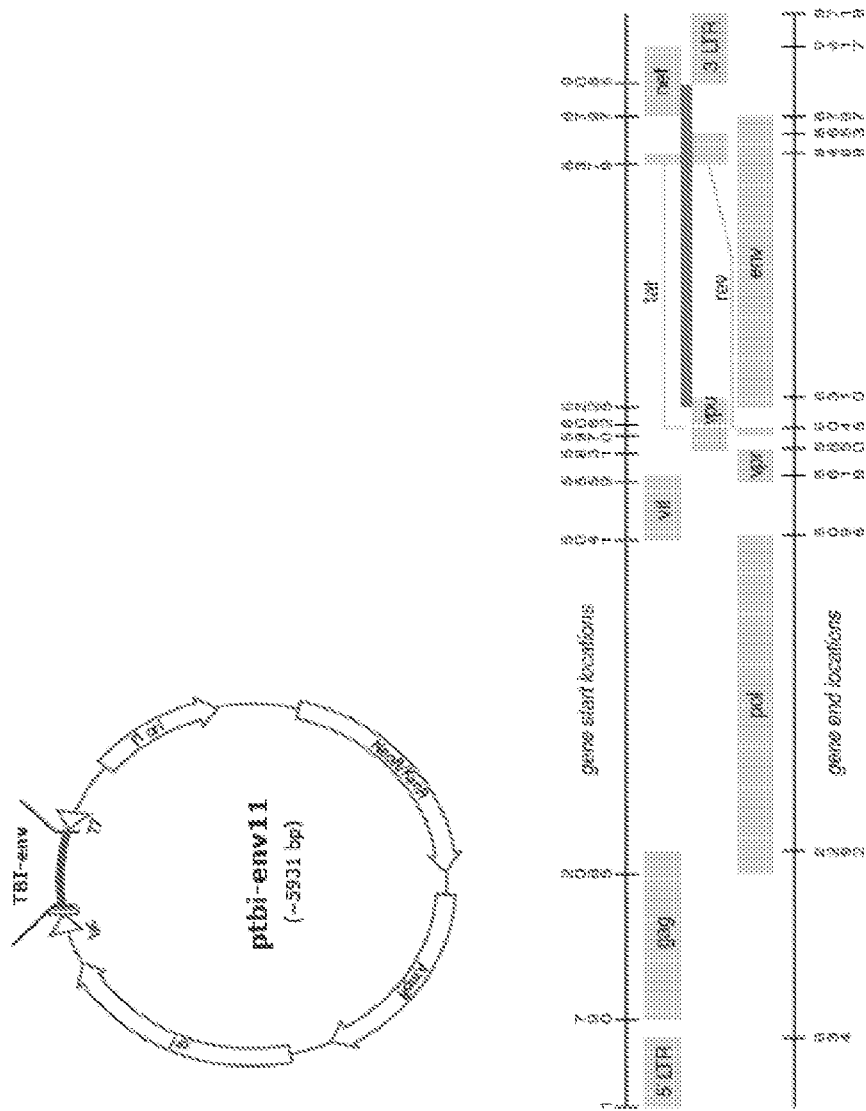
FIG. 10 shows a plasmid in which an envelope gene from a virus particle product was cloned and sequenced, in accordance with an embodiment of the invention.
Figure 11:
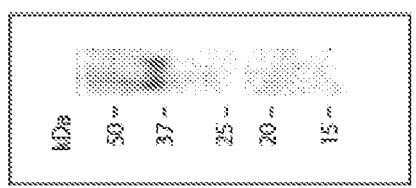
FIG. 11 illustrates results of (left) an ELISA and (right) a Western blot, showing that supernatants from mouse hybridoma cells produce virus particle produce-specific antibodies, in accordance with an embodiment of the invention.
Figure 11:
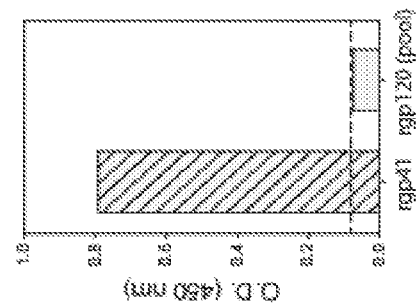
Figure 12:
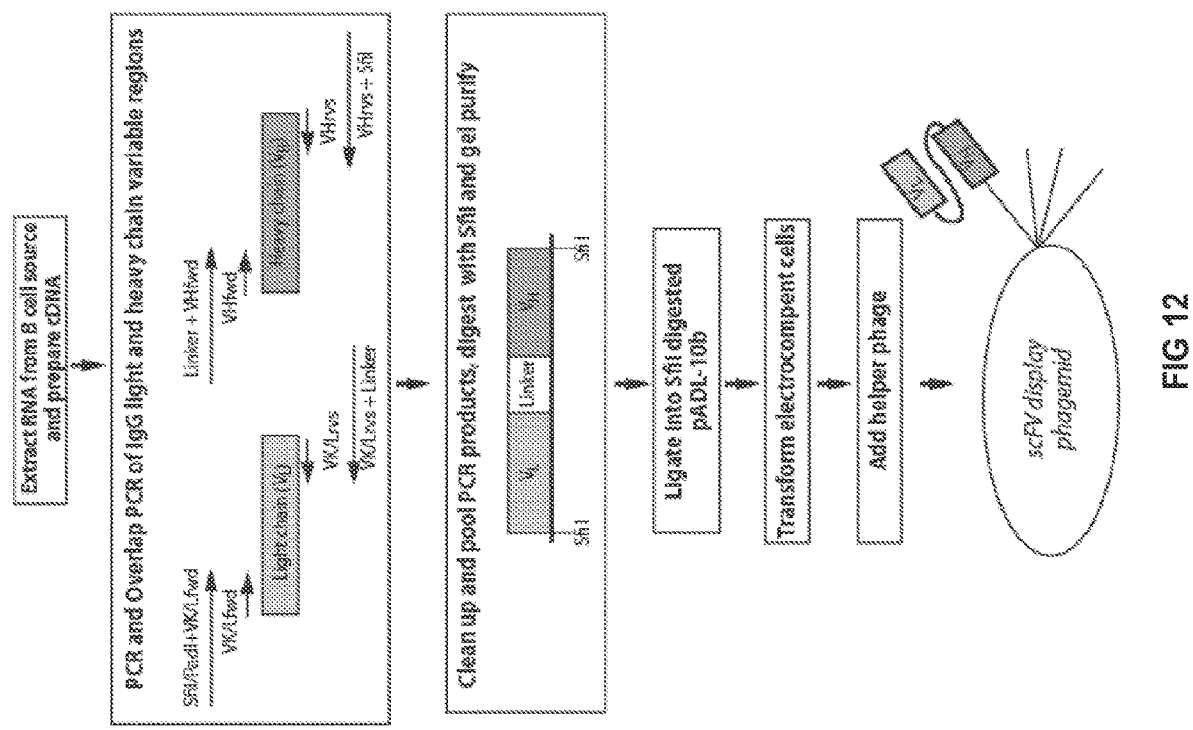
FIG. 12 illustrates an antibody-phage display approach used with splenocytes and bone marrow derived from rabbits immunized with TEGS, in accordance with an embodiment of the invention.

FIG. 9 shows a substantial improvement of the virus particle product. Various samples (i-vii) of medium compositions and virus particle products were mixed with lithium dodecyl sulfate buffer (Invitrogen) and reducing agent (Invitrogen), heated (70° C., 10 min), loaded into the lanes of a 12% Bis-Tris gel (Invitrogen), and electrophoresed (200V, 40 min) in MES buffer (Invitrogen). The LEFT panel shows an image of a gel stained with G-250 coomassic (BioRad). The samples shown are: i) scrum containing medium only, ii) scrum-grown TEGS, iii) serum-free medium, iv) serum-free TEGS. The results in the left panel demonstrate the superiority of TEGS produced using serum-free medium, such as medium B in Example 2. The serum-free medium has markedly reduced levels of more than 8 different proteins. In comparison to a composition similar to mHIVenv, serum-free TEGS have greatly reduced levels of proteins in the 175 kDa and 60 kDa range and the overall composition is distinguished. The RIGHT panel shows the Western blot results of the immunoreactivity of a high positive control (BioRad; pooled sera from HIV-infected individuals). The samples shown are: v) concentrated serum-free TBI01280, vi) serum-free TEGS, and vii) serum-free medium. The results in the right panel demonstrate that HIV proteins are retained through the various procedures (i.e., FIG. 1 elements 106 thru 112) involved in producing TEGS.

Example 9: Cloning of Envelope Genes from the Virus Particle Product

It will be apparent to those skilled in the art that the HIV envelope gene can be cloned and expressed in prokaryotic and eukaryotic cells and even cell-free systems. The expression of HIV envelope proteins or peptides can facilitate a wide variety of downstream applications related to the production and/or characterization of anti-envelope antibodies.

In the case of FIG. 10, it is demonstrated that an envelope gene from a virus particle product has been cloned into a plasmid and sequenced, as shown below. HIV-1 was isolated from the plasma of a healthy blood bank donor who tested negative for anti-HIV antibodies. After propagation of the virus in primary human mononuclear blood cells, RNA was extracted from the virus particle product and amplified by RT-PCR using consensus primers for HIV-1 clade B isolates. The PCR amplicons were cloned into a pcr2.1-TOPO vector (Invitrogen) that was then used to transform competent cells (Invitrogen). Colonies from the transformed *E. coli* preparations were selected and cultured. Plasmids from the cultures were isolated (minipreps; Qiagen) and sequenced (ElimBio). The resulting sequences were compiled and analyzed using tools in the LANL online database (http://www.hiv.lanl.gov/).

The sequence encoding gp41 (SEQ ID NO: 137) in the pcr2.1-TOPO vector was amplified and ligated into an expression vector, in-frame, between an TL-2 secretion peptide sequence and a sequence encoding a human IgG-Fc tag. After routine preparation of a plasmid stock, gp41 expression vector was transfected into 293 cells. Dot blot analysis of the cell lysate and cell culture supernatant confirmed the expression and secretion of gp41 (data not shown). The resulting secreted protein, derived from the virus particle product, can be useful for analysis of ABPs elicited by immunization with the virus particle product or otherwise. SEQ ID NO: 137:

ATGGGGCACCATGCTCCTTGGGATGTTGATGATCTGTAGTGCTGCAGATA

AATTGTGGGTCACAGTCTACTATGGGGTACCTGTGTGGAAAGAAGCAACC

ACCACTCTATTTTGTGCATCAGATGCTAAAGCATATGATACAGAGGTACA

TAATGTTTGGGCCACGCATGCCTGTGTACCCACAGACCCCAACCCACAAG

AAGTAGTATTGGAAAATGTGACAGAAAATTTTAACATGTGGAAAAATGAC

ATGGTAGAACAAATGCATGAGGATATAATCAGTTTATGGGATCAAAGCCT

AAAGCCATGTGTAAAATTAACCCCACTCTGTGTCACTTTAAATTGCAATG

ATGTCAATAATAATAGTACTATCAACAATGGAACTACTAATGCCACTAGT

CATAGTGGGGGAAAAATAGAGAGAGGAGAAATAAAAAATTGCTCTTTCAA

TGTCACCACAAACATAAAAAATAAGCTGCAGAAAGAATATGCACTGTTTT

ATAAGCTTGATCTAGTACCAACAGATGATAATAATTCTAGATATAGGTTG

ATACATTGTAATACCTTAGTCATTACACAAGCCTGTCCAAAGGTATCCTT

TGAGCCAATTCCCATACATTATTGTGCCCCGGCTGGTTTTGCGATTCTAA

AGTGCAAAGATAGGAATTTCACAGGAAAAGGACAATGTAAAAATGTCAGC

ACAGTACAATGTACACATGGCATTAGGCCAGTAGTGTCAACTCAACTGCT

GTTAAATGGCAGTCTAGCAGAAGATGGGGTAGTAATTAGATCTGCCAATA

TCACAGACAATACTAAAACCATAATAGTACAGTTGAAGGAAGCTGTAGAA

ATTAATTGTACAAGACCCAATAACAATACAAGGAAAAGTATAACTATAGG

ACCAGGGAGAGCATTTTGGACAACAGGAGGAATAATAGGAGATATAAGAC

AAGCACATTGTAACCTTAGTAGCACAAAATGGAATAACACTTTAAGACAG

ATAGCTACAAAATTAAGAGAACAATTTGGTAACAAAACAATAGTTTTTAA

TCAATCCTCAGGAGGGGACCAAGAAATTGTGATGCACACTTTTAATTGTG

GAGGGGAATTTTTCTACTGTAGTACAACACAACTGTTTAATAGTACTTGG

ATTGCAAATAAGACTGGGAATGATACTGGAGGATCAAATGGAACTATTAC

ACTTCCATGCAGAATAAAACAAATTGTAAACATGTGGCAGGAAGTAGGAA

AAGCAATGTATGCCCCTCCCATCAAAGGACAAATTAGATGTTCATCAAAC

ATTACAGGACTGCTATTATTAAGAGATGGTGGTAAGAATAACGGGACAGG

AAACATGACAGAAATCTTCAGACCTGGAGGAGGAGATATGAGGGACAATT

GGAGAAGTGAATTATATAAATATAAAGTAGTAAAAATTGAACCATTAGGA

GTAGCACCCACCAAGGCAAAGAGAAGAGTGGTGCAGAGAGAAAAAAGAGC

GGTGGGAACACTAGGAGCCTTGTTCCTTGGGTTCTTGGGAACAGCAGGAA

-continued

GCACTATGGGCGCAGCATCACTAACGCTGACGGTACAGGCCAGACTATTA

TTGCCTGGTATAGTGCAACAGCAAAACAATTTGCTGAGAGCTATTGAGGC

GCAACAGCATTTGTTGCAACTCACAGTCTGGGGCATCAAGCAGCTCCAGG

CAAGAGTCCTGGCTATGGAAAGATACCTACAGGATCAACAGCTCCTAGGG

ATTTGGGGTTGCGCTGGAAAACTCATTTGCACCACAGCTGTGCCTTGGAA

TACTAGTTGGAGTAATAAATCTCTGGATCAGATTTGGAATAACATGACCT

GGATGCAATGGGAAAGAGAAATTGACAATTACACACACACAATATACAGC

TTAATTGAAGAATCGCAGAACCAACAAGAAAAAAATGAACAAGAATTATT

GGAACTAGACAAGTGGGCAAGTTTGTGGAATTGGTTTGACATAACAAACT

GGCTGTGGTATATAAAAATATTCATAATGGTAGTAGGAGGCTTAGTAGGT

TTAAGAATAGTTTTTGCTGTACTTTCTATAGTGAATAGAGTTAGGCAGGG

ATACTCACCATTATCGTTGCAGACCCGATTCCCAGTCCAGAGGGGACCCG

ACAGGCCCGAAGGAATCGAAGAAGAAGGTGGAGAGAGAGACAGAGACAGA

TCCGGTCGATTAGTGACCGGATTCTTACCTCTTATCTGGGACGACCTGCG

GAGCCTGTGCCTCTTCAGCTACCGCCGCTTGAGAGACTTACTCTTGATTG

CAGCGAGGATTGTGGAACTTCTGGGACGCAGGGGGTGGGAACTCCTCAAA

TATTGGTGGAATCTCCTAAAATATTGGAGTCAGGAACTAAAGAATAGTGC

TGTCAGCTTGTACAACGCCACAGCTATAGCAGTAGCTGAGGGAACAGATA

GGGTTATAGAAATAGTAAGAAGAACCTTTAGAGCTATTATCCACATACCT

AGAAGAATAAGACAGGGCTTGGAAAGGGCTTTGCTATAAGATGGGTGGCA

AGTGGTCAAAAAGTAGTGTGGTTGGATGGCCTGAGATAAGAGAAAGAATG

AGACGAACCGAGCCACGAACCGAGCCAGCAGCAGAGGGGGTGGGAGCAGC

ATCTCGAGACCTAGAAAAACATGGAGCAATCACAAGTAGCAATACAGCAG

CTACTAATGCTGCTTGTGCCTGGCTAGAAGCACAAGAAGAAGAGGAAGTG

GGTTTTCCAGTCAGACCTCAGGTACCTTTAAGACCAATGACCT

Example 10: Production of Cell Lines Producing TEGS-Specific Antibodies

FIG. 11 shows that the supernatants from mouse hybridoma cells produce virus-particle-product-specific antibodies. Mice were repeatedly injected with TEGS at biweekly intervals. With splenocytes from the mice, hybridomas were constructed. The supernatants from the hybridoma cultures were screened in ELISA assays for immunoreactivity to TEGS and to recombinant HIV proteins. The ELISA and Western blot data show that the hybridoma fluid is reactive with recombinant gp41, but not pooled recombinant gp120 proteins. While pre-immune serum from the mouse was not available for testing, normal mouse serum generally lacks immunoreactivity with recombinant HIV proteins. Thus, the anti-gp41 response likely resulted from immunization with TEGS. Therefore, the anti-gp41 immunoreactivity is likely TEGS-specific. It will be apparent to one skilled in the art that mouse B-cell hybridomas comprise immortalized cell lines that produce monoclonal antibodies.

Example 11: Cloning of TEGS-Specific ABPs from Rabbits Immunized with TEGS

FIG. 12 illustrates an antibody-phage display approach that was used with splenocytes and bone marrow derived from rabbits immunized with TEGS. Cells binding TEGS were selected, and total RNA was extracted. The RNA was converted to cDNA, and the antibody-encoding DNA was PCR-amplified using custom sequence-specific oligonucleotides (SSOs). The DNA was cloned into a phagemid vector (PADL-10b; Ab Design Labs; San Diego, Calif.) to create a library, the phagemid library was transfected into bacteria, the resulting bacteriophages were isolated, antigen-specific bacteriophages were captured (i.e., panning with TEGS), and the candidate antibody genes were subcloned into custom expression vectors. Unique SSOs were designed and validated. The resulting phagemids expressed novel single-chain variable fragment (scFV) proteins based on the unique combination of SSOs and the linker sequence used. Panning was performed using TEGS. For subcloning of the scFVs, a plasmid containing an IL-2 secretion signal and human Fc gene was used (Invivogen; San Diego, Calif.). The multiple cloning site (MCS) of the plasmid was uniquely modified to enable the subcloning of antibody sequences from the phagemids. Specifically, new restriction sites were introduced and a portion of the MCS was deleted.

Phagemids captured by panning with TEGS were used to infect *E. coli*. Phagemid DNA from the *E. coli* cultures was sequenced. The DNA sequences were analyzed using web-based tools at the international imMunoGeneTics information system (IMGT). These analyses were used in the identification of the rabbit variable chain genes and constructing alignments of the complementarity determining regions or CDRs. Amino acid sequences and nucleic acid sequences of antibody regions are provided in Tables 1 and 2, respectively.

Example 12: Production and Screening of TEGS-Specific ABPs

Figure 13:
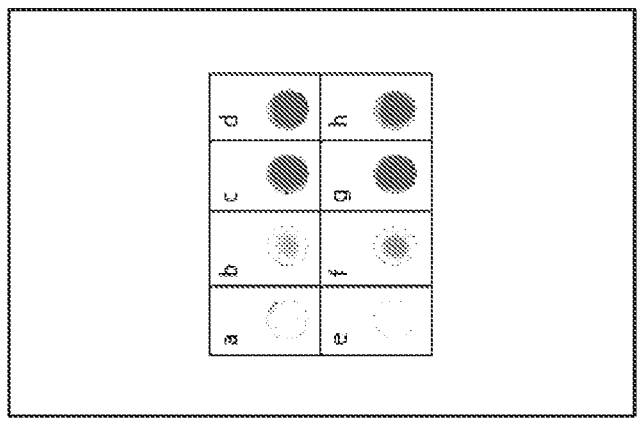
FIG. 13 illustrates (left) a TEGS-specific ABP and (right) Western blot results, showing that the TEGS-specific ABP was produced and validated, in accordance with an embodiment of the invention.
Figure 13:
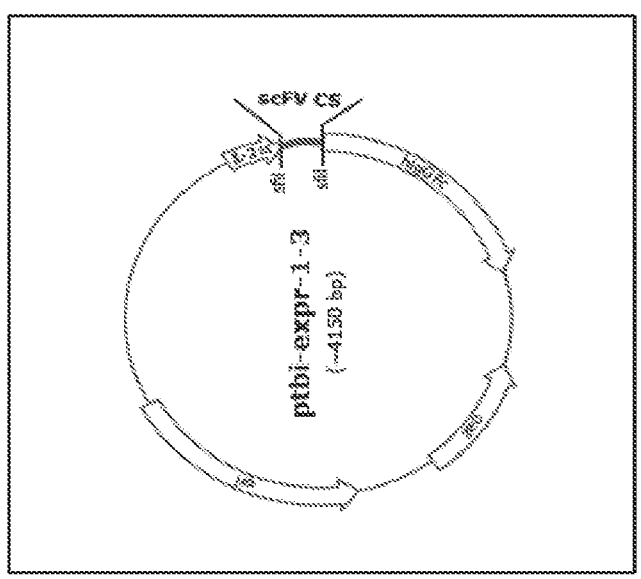
Figure 14:
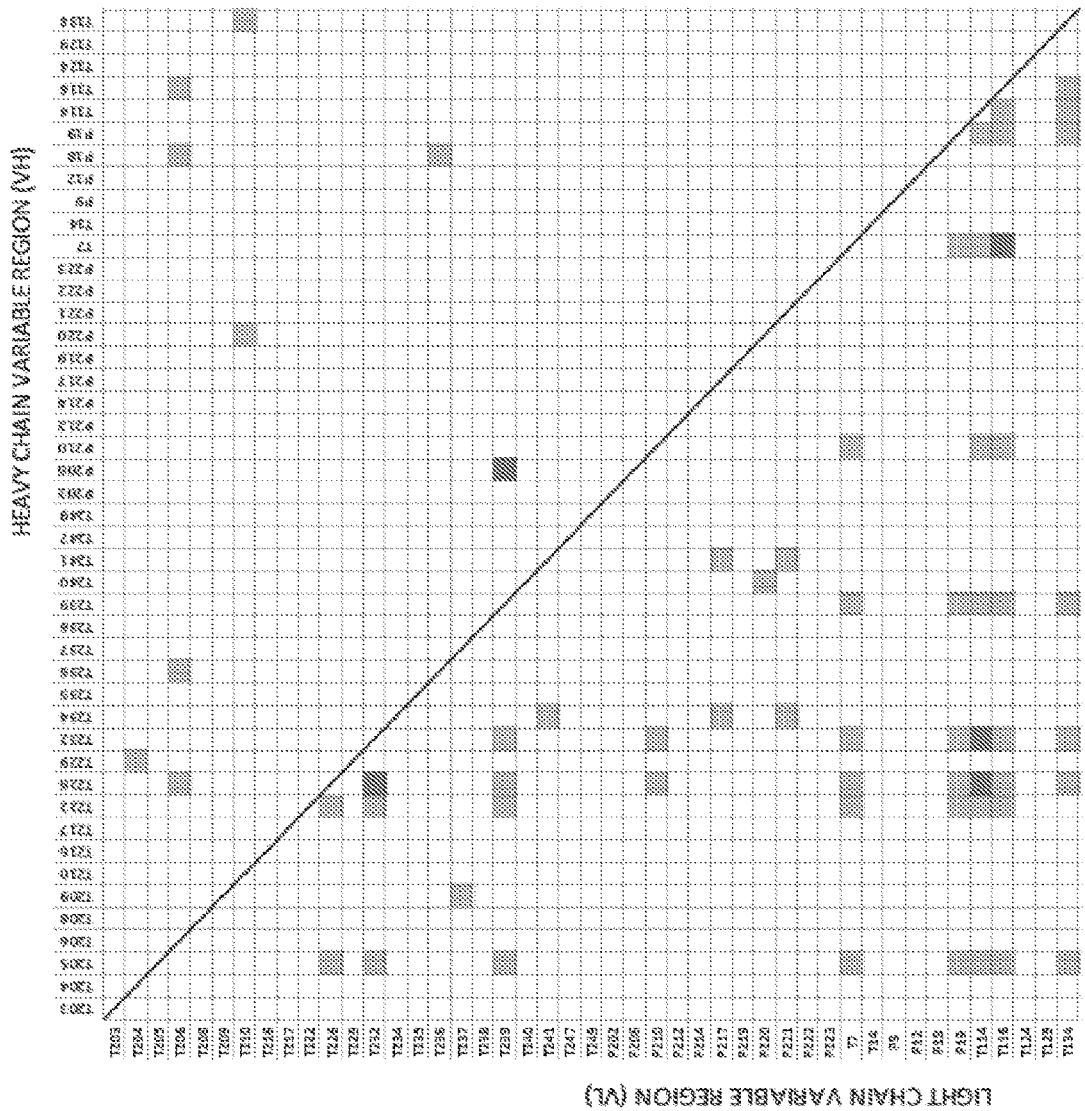
FIG. 14 shows a compilation of a similarity matrix between heavy chain variable region amino acid sequences, and a similarity matrix between light chain variable region amino acid sequences, in accordance with an embodiment of the invention.

FIG. 13 illustrates a TEGS-specific ABP that was produced and validated. (LEFT) Briefly, the multiple cloning site (MCS) of an expression vector encoding an IL-2 secretion peptide and a human IgG Fc chain (Invivogen, San Diego, Calif.) was modified to enable the in-frame and directional ligation of the scFV constructs; unique SfiI sites were added and part of the MCS was deleted. The scFV insert (TBIfabT7; SEQ ID No: 151) from a phagemid captured with immobilized TEGS was excised with SfiI and then subcloned into an expression vector in-frame between sequences encoding an TIL-2 secretion peptide and a human IgG Fc protein. Following the transfection of 293 cells, the cell culture supernatants were collected and analyzed for immunoreactivity in dot blot assays. (RIGHT) Shown are the results from a blot that was spotted with a) dPBS, e) FBS, and the concentrated supernatants from cultures of human primary mononuclear cells infected with HIV-1 virus particle products b) TBI01280-SF2, c) 1292-GNV, d) 1362-GNV, and TEGS-prepared from those isolates respectively (f-h). The supernatant from 293 cells transfected with the TBIfabT7 expression vector was used as a primary antibody, followed by the use of an anti-human IgG-HRP secondary antibody. The results show that TBIfabT7 is immunoreactive with each of the acute HIV infection virus isolates and, to a similar degree, with each of the TEGS compositions. TBIfabT7 is not immunoreactive with the multitude of proteins present in fetal bovine serum. In addition to demonstrating the physical production of a TEGS-specific ABP, these results establish the utility of TEGS for three distinct applications: immunization, phagemid capture, and ABP screening.

Example 13: Analytics of TEGS-Specific ABPs

The preceding Examples demonstrate the ability to produce virus particle product proteins and virus particle specific ABPs. This combined ability enables the exquisite analysis of the relationships among simple to complex TEGS epitopes and TEGS-specific ABPs. One analytic goal is to identify a highly conserved TEGS epitope(s) that is targeted by a broadly neutralizing TEGS-specific ABP(s). One skilled in the art will appreciate that a variety of analytic and experimental approaches can be used to map TEGS-specific ABPs to distinct TEGS epitopes.

In the case of FIG. 14, an analytic approach to determining the relatedness among TEGS-specific and recombinant HIV protein-specific ABPs is demonstrated. Briefly, a similarity matrix between all of the heavy chain variable region amino acid sequences in Table 2 was computed using the BioEdit software package. A separate similarity matrix was computed for the light chain variable region amino acid sequences. Then, the two matrices were compiled in a spreadsheet. Shown are the two similarity matrices separated by a dark diagonal line. Shaded boxes indicate amino acid sequences having a high degree of homology (e.g. >90%). The results reveal the presence of highly homologous amino acid sequences; the majority are among light chains. One skilled in the art will appreciate that similar analyses can be performed on the complementarity determining regions and other subsets of antibody sequences. When combined with protein or peptide binding data, the approach demonstrated can provide insight for the fine specifities of ABPs.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A composition comprising polyclonal antibodies, wherein the polyclonal antibodies selectively bind to an epitope on HIV-1 trimeric envelope glycoprotein subunits (TEGS) of infectious HIV-1 virus particles that infect human peripheral blood mononuclear cells (PBMCs) and do not infect non-PBMC, and
   wherein the polyclonal antibodies neutralize infectious HIV-1 particles thereby reducing infection of human PBMCs; and
   wherein the polyclonal antibodies are produced by immunization of a mammal with the TEGS,
   wherein the TEGS are prepared by a process comprising:
     obtaining infectious HIV-1 virus particles from human PBMCs cultures grown in serum-free media;
     contacting the infectious HIV-1 virus particles with agents that selectively remove from the particles, viral RNA and viral capsid protein while retaining viral envelope protein in a non-denatured conformation, wherein the agents do not chemically fix or cross-link the envelope protein; and
     isolating protein from the contacted infectious HIV-1 virus particles wherein the isolated protein comprises non-infectious complexes comprising a trimeric envelope glycoprotein subunit, the subunit comprising HIV-1 envelope comprising gp120 bound to membrane-anchored gp41, wherein gp120 and gp41 are not chemically fixed or cross-linked and substantially free of HIV-1 capsid protein, reverse transcriptase and RNA.

2. The composition of claim 1, wherein the infectious HIV-1 virus particles are Fiebig I/II isolates or founder virus.

3. The composition of claim 1, wherein the agents comprise cyclodextrin and protease-free Benzonase.

4. The composition of claim 1, wherein the polyclonal antibodies neutralize infectious HIV-1 particles from at least one HIV-1 R5 strain and at least one HIV-1 X4 strain.

5. An immunotherapeutic method comprising administering to a subject a therapeutic amount of the composition of claim 1.

6. A method for generating polyclonal antibodies that selectively bind to an epitope on HIV-1 trimeric envelope glycoprotein subunits (TEGS) of infectious HIV-1 virus particles that infect human peripheral blood mononuclear cells (PBMCs) and do not infect non-PBMC, the method comprising:
   immunizing a mammal with a composition comprising the TEGS, wherein the composition is prepared by a process comprising:
     obtaining infectious HIV-1 virus particles from human PBMCs cultures grown in serum-free media;
     contacting the infectious HIV-1 virus particles with agents that selectively remove from the particles, viral RNA and viral capsid protein while retaining viral envelope protein in a non-denatured conformation, wherein the agents do not chemically fix or cross-link the envelope protein; and
     isolating protein from the contacted infectious HIV-1 virus particles wherein the isolated protein comprises non-infectious complexes comprising a trimeric envelope glycoprotein subunit, the subunit comprising HIV-1 envelope comprising gp120 bound to membrane-anchored gp41, wherein gp120 and gp41 are not chemically fixed or cross-linked and substantially free of HIV-1 capsid protein, reverse transcriptase and RNA,
   wherein the polyclonal antibodies neutralize infectious HIV-1 particles thereby reducing infection of human PBMCs.

7. The method of claim 6, wherein the infectious HIV-1 virus particles are Fiebig I/II isolates.

8. The method of claim 6, wherein the infectious HIV-1 virus particles are Fiebig I/II founder virus.

9. The method of claim 6, wherein the agents comprise cyclodextrin and protease-free Benzonase.

10. The method of claim 6, wherein the polyclonal antibodies neutralize infectious HIV-1 particles from at least one HIV-1 R5 strain.

11. The method of claim 6, wherein the polyclonal antibodies neutralize infectious HIV-1 particles from at least one HIV-1 X4 strain.

* * * * *

UNITED STATES PATENT AND TRADEMARK OFFICE
CERTIFICATE OF CORRECTION

| | | |
|---|---|---|
| PATENT NO. | : 11,267,872 B2 | Page 1 of 1 |
| APPLICATION NO. | : 16/385455 | |
| DATED | : March 8, 2022 | |
| INVENTOR(S) | : M. Scott Killian et al. | |

It is certified that error appears in the above-identified patent and that said Letters Patent is hereby corrected as shown below:

In the Specification

In Column 11, Line 29, please replace "camclid" with --- camelid ---; and

In Column 56, Line 26, please replace "scrum-grown" with --- serum-grown ---.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*